US012759972B2

(12) United States Patent
Shin et al.

(10) Patent No.: US 12,759,972 B2
(45) Date of Patent: Oct. 13, 2026

(54) ORGANIC COMPOUND, AND ORGANIC LIGHT EMITTING DIODE AND ORGANIC LIGHT EMITTING DEVICE INCLUDING THE SAME

(71) Applicants: LG Display Co., Ltd, Seoul (KR); LG CHEM, LTD., Seoul (KR)

(72) Inventors: Ji-Cheol Shin, Paju-si (KR); Shin-Han Kim, Paju-si (KR); Jeong-Dae Seo, Paju-si (KR); Joo-Yong Yoon, Seoul (KR); Jun Yun, Seoul (KR); Dong-Heon Kim, Seoul (KR); Yong-Han Lee, Seoul (KR); Sung-Jae Lee, Seoul (KR)

(73) Assignees: LG Display Co., Ltd., Seoul (KR); LG CHEM, LTD., Seoul (KR)

( * ) Notice: Subject to any disclaimer, the term of this patent is extended or adjusted under 35 U.S.C. 154(b) by 1062 days.

(21) Appl. No.: 17/553,380

(22) Filed: Dec. 16, 2021

(65) Prior Publication Data

US 2022/0194883 A1 Jun. 23, 2022

(30) Foreign Application Priority Data

Dec. 21, 2020 (KR) ........................ 10-2020-0179674

(51) Int. Cl.
*C07C 255/51* (2006.01)
*C07C 22/08* (2006.01)
(Continued)

(52) U.S. Cl.
CPC ............ *C07C 255/51* (2013.01); *C07C 22/08* (2013.01); *C07C 25/22* (2013.01); *H10K 85/615* (2023.02); *H10K 50/11* (2023.02); *H10K 50/17* (2023.02)

(58) Field of Classification Search
CPC ..... C07C 25/22; C07C 22/08; C07C 2603/10; C07C 255/54; C07C 255/51;
(Continued)

(56) References Cited

U.S. PATENT DOCUMENTS 10,658,593 B2 5/2020 Kim et al.
12,382,826 B2 * 8/2025 Shin .................. H10K 85/6572
(Continued)

FOREIGN PATENT DOCUMENTS

CN 107017349 A 8/2017
CN 107814753 A 3/2018
(Continued)

OTHER PUBLICATIONS

Endo, Y., Hasegawa, M., Matsui, T., Yagi, H., Hino, S., & Mazaki, Y. (2014). Synthesis and electronic structure of dicyanofulvene-fused electron accepting molecule based on a 1, 5-dihydro-s-indacene framework. Organic letters, 16(21), 5608-5611. (Year: 2014).*
(Continued)

*Primary Examiner* — Dawn L Garrett
(74) *Attorney, Agent, or Firm* — Morgan, Lewis & Bockius LLP

(57) ABSTRACT

The present disclosure relates to an organic compound being represented by Formula 1, an organic light emitting diode including the organic compound and an organic light emitting device including the organic light emitting diode. The organic compound is included in an organic layer of the organic light emitting diode.

[Formula 1]

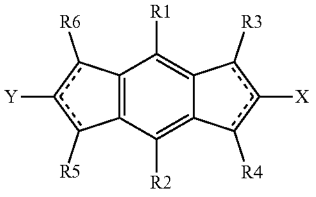

12 Claims, 4 Drawing Sheets

(51) Int. Cl.

| | |
|---|---|
| ***C07C 25/22*** | (2006.01) |
| ***H10K 50/11*** | (2023.01) |
| ***H10K 50/17*** | (2023.01) |
| ***H10K 85/60*** | (2023.01) |

(58) Field of Classification Search

CPC . C07C 255/47; C07C 2603/12; C07C 255/50; H10K 85/615; H10K 50/11; H10K 50/131; H10K 50/17; H10K 50/10; H10K 50/15; C09K 11/06; C09K 2211/1011

See application file for complete search history.

(56) References Cited

U.S. PATENT DOCUMENTS

| | | | | |
|---|---|---|---|---|
| 2012/0298968 | A1* | 11/2012 | Kim | H10K 50/17 257/40 |
| 2016/0149151 | A1* | 5/2016 | Kam | H10K 59/80518 257/40 |
| 2018/0062083 | A1 | 3/2018 | Kim et al. | |
| 2019/0207123 | A1 | 7/2019 | Yoon et al. | |
| 2020/0144552 | A1 | 5/2020 | Kim et al. | |
| 2020/0199090 | A1 | 6/2020 | Jang et al. | |
| 2020/0303651 | A1 | 9/2020 | Kim et al. | |
| 2021/0202845 | A1 | 7/2021 | Shin et al. | |
| 2021/0202847 | A1 | 7/2021 | Shin et al. | |
| 2021/0202857 | A1 | 7/2021 | Shin et al. | |
| 2021/0202858 | A1 | 7/2021 | Shin et al. | |
| 2021/0202859 | A1 | 7/2021 | Shin et al. | |
| 2021/0202860 | A1 | 7/2021 | Shin et al. | |
| 2022/0158110 | A1 | 5/2022 | Jeon et al. | |
| 2025/0318426 | A1* | 10/2025 | Shin | H10K 85/633 |

FOREIGN PATENT DOCUMENTS

| | | | | |
|---|---|---|---|---|
| CN | 110010781 A | | 7/2019 | |
| CN | 110495005 A | | 11/2019 | |
| CN | 111349066 A | | 6/2020 | |
| CN | 113130798 A | | 7/2021 | |
| CN | 113130801 A | | 7/2021 | |
| CN | 113130815 A | | 7/2021 | |
| CN | 113130828 A | | 7/2021 | |
| CN | 113130830 A | | 7/2021 | |
| CN | 113130831 A | | 7/2021 | |
| CN | 114512619 A | | 5/2022 | |
| WO | WO-2018221871 A1 | * | 12/2018 | C07C 211/54 |

OTHER PUBLICATIONS

Office Action dated Sep. 22, 2023 from the China National Intellectual Property Administration 202111435831.8.

* cited by examiner

ORGANIC COMPOUND, AND ORGANIC LIGHT EMITTING DIODE AND ORGANIC LIGHT EMITTING DEVICE INCLUDING THE SAME

CROSS-REFERENCE TO RELATED APPLICATIONS

The present application claims the benefit of Korean Patent Application No. 10-2020-0179674 filed in the Republic of Korea on Dec. 21, 2020, which is hereby incorporated by reference in its entirety.

BACKGROUND

Technical Field

The present disclosure relates to an organic compound, and more particularly, to an organic compound having improved hole injection property, hole generation property and/or hole transporting property, and an organic light emitting diode (OLED) and an organic light emitting device including the organic compound.

Discussion of the Related Art

Recently, requirement for flat panel display devices having small occupied area is increased. Among the flat panel display devices, a technology of an organic light emitting display device, which includes an OLED, is rapidly developed.

The OLED emits light by injecting electrons from a cathode as an electron injection electrode and holes from an anode as a hole injection electrode into an organic emitting layer, combining the electrons with the holes, generating an exciton, and tranferring the exciton from an excited state to a ground state. A flexible transparent substrate, for example, a plastic substrate, can be used as a base substrate where elements are formed. In addition, the OLED can be operated at a voltage (e.g., 10V or below) lower than a voltage required to operate other display devices and has low power consumption. Moreover, the light from the OLED has excellent color purity.

The OLED may include a first electrode as an anode, a second electrode as cathode facing the first electrode and an organic emitting layer between the first and second electrodes.

To improve the emitting efficiency of the OLED, the organic emitting layer may include a hole injection layer (HIL), a hole transporting layer (HTL), an emitting material layer (EML), an electron transporting layer (ETL) and an electron injection layer (EIL) sequentially stacked on the first electrode.

In the OLED, the hole from the first electrode as the anode is transferred into the EML through the HIL and the HTL, and the electron from the second electrode as the cathode is transferred into the EML through the EIL and the ETL. The hole and the electron are combined in the EML to form the exciton, and the exciton is tranferred from an excited state to a ground state to emit the light.

To provide low driving voltage and sufficient emitting efficiency and lifespan of the OLED, a hole injection material having sufficient hole injection efficiency is required.

SUMMARY

Accordingly, embodiments of the present disclosure are directed to an organic compound, an OLED and an organic light emitting device that substantially obviate one or more of the problems associated with the limitations and disadvantages of the related art.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as in the appended drawings.

To achieve these and other aspects in accordance with the purpose of embodiments of the present disclosure, as embodied and broadly described herein, an aspect of the present disclosure is an organic compound of Formula 1:

[Formula 1]

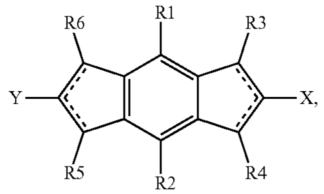

wherein each of R1 and R2 is independently selected from the group consisting of hydrogen, deuterium, halogen and cyano, wherein each of R3 to R6 is independently selected from the group consisting of halogen, cyano, malononitrile, C1 to C10 haloalkyl group and C1 to C10 haloalkoxy group, and at least one of R3 and R4 and at least one of R5 and R6 are malononitrile, wherein each of X and Y is independently phenyl substituted with at least one of C1 to C10 alkyl group, halogen, cyano, malononitrile, C1 to C10 haloalkyl group and C1 to C10 haloalkoxy group, and X and Y have a difference in at least one of a substituent and a position of a substituent.

Another aspect of the present disclosure is an organic light emitting diode comprising a first electrode; a second electrode facing the first electrode; a first emitting material layer positioned between the first and second electrodes; and an organic layer positioned between the first electrode and the first emitting material layer or between the first emitting material layer and the second electrode, wherein the organic layer includes the above organic compound.

Another aspect of the present disclosure is an organic light emitting device comprising a substrate; the above organic light emitting diode positioned on the substrate; and an encapsulation film covering the organic light emitting diode.

It is to be understood that both the foregoing general description and the following detailed description are exemplary and explanatory and are intended to further explain the present disclosure as claimed.

BRIEF DESCRIPTION OF THE DRAWINGS

The accompanying drawings, which are included to provide a further understanding of the present disclosure and are incorporated in and constitute a part of this specification, illustrate embodiments of the present disclosure and together with the description serve to explain principles of the present disclosure.

DETAILED DESCRIPTION

Reference will now be made in detail to some of the examples and preferred embodiments, which are illustrated in the accompanying drawings.

In an OLED and an organic light emitting device of the present disclosure, new organic compound is applied to at least one of a hole injection layer and a p-type charge generation layer. For example, the organic light emitting device may be an organic light emitting display device or an organic lightening device. As an example, an organic light emitting display device, which is a display device including the OLED of the present disclosure, will be mainly described.

Figure 1:
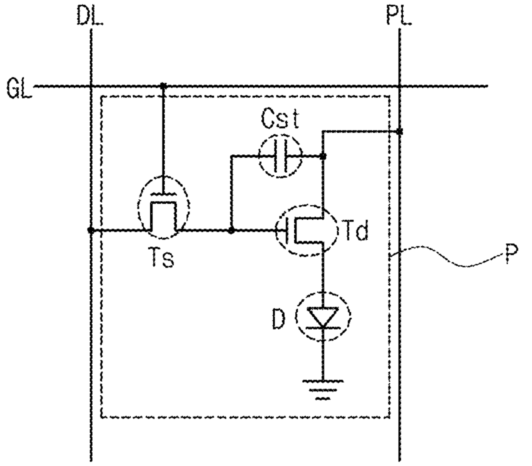
FIG. 1 is a schematic circuit diagram of an organic light emitting display device of the present disclosure.

FIG. 1 is a schematic circuit diagram illustrating an organic light emitting display device of the present disclosure.

As illustrated in FIG. 1, a gate line GL and a data line DL, which cross each other to define a pixel P, and a power line PL are formed in an organic light emitting display device. A switching thin film transistor (TFT) Ts, a driving TFT Td, a storage capacitor Cst and an OLED D are formed in the pixel P. The pixel P may include a red pixel, a green pixel and a blue pixel. In addition, the pixel P may further include a white pixel.

The switching thin film transistor Ts is connected to the gate line GL and the data line DL, and the driving thin film transistor Td and the storage capacitor Cst are connected between the switching thin film transistor Ts and the power line PL. The OLED D is connected to the driving thin film transistor Td. When the switching thin film transistor Ts is turned on by the gate signal applied through the gate line GL, the data signal applied through the data line DL is applied to a gate electrode of the driving thin film transistor Td and one electrode of the storage capacitor Cst through the switching thin film transistor Ts.

The driving thin film transistor Td is turned on by the data signal applied into the gate electrode so that a current proportional to the data signal is supplied from the power line PL to the OLED D through the driving thin film transistor Tr. The OLED D emits light having a luminance proportional to the current flowing through the driving thin film transistor Td. In this case, the storage capacitor Cst is charge with a voltage proportional to the data signal so that the voltage of the gate electrode in the driving thin film transistor Td is kept constant during one frame. Therefore, the organic light emitting display device can display a desired image.

Figure 2:
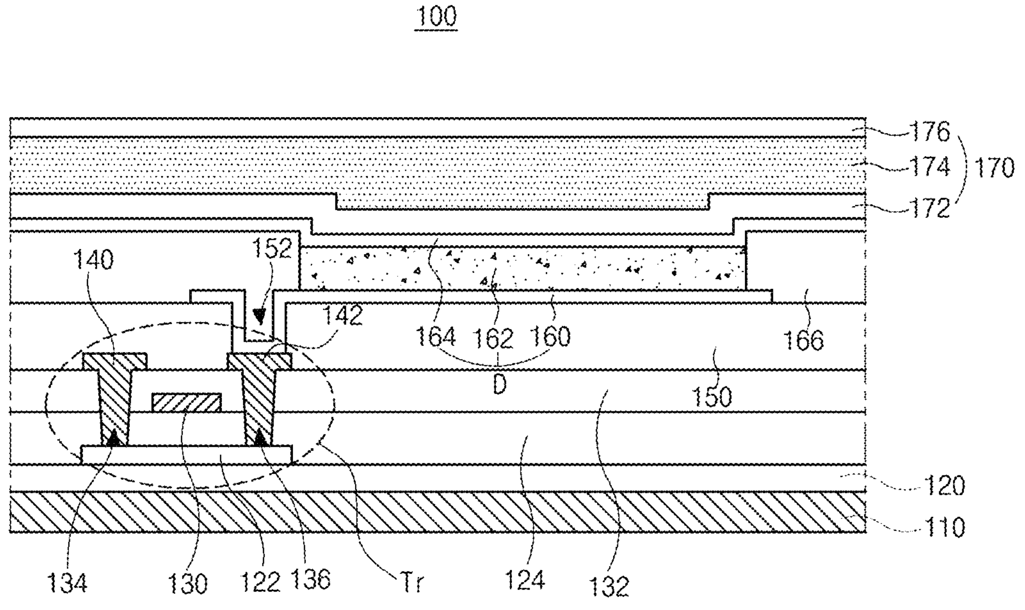
FIG. 2 is a schematic cross-sectional view of an organic light emitting device according to a first embodiment of the present disclosure.

FIG. 2 is a schematic cross-sectional view illustrating an organic light emitting display device according to a first embodiment of the present disclosure.

As illustrated in FIG. 2, the organic light emitting display device 100 includes a substrate 110, a TFT Tr and an OLED D disposed on a planarization layer 150 and connected to the TFT Tr. For example, the organic light emitting display device 100 may include a red pixel, a green pixel and a blue pixel, and the OLED D may be formed in each of the red, green and blue pixels. Namely, the OLEDs D emitting red light, green light and blue light may be provided in the red, green and blue pixels, respectively.

The substrate 110 may be a glass substrate or a flexible substrate. For example, the flexible substrate may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 120 is formed on the substrate, and the TFT Tr is formed on the buffer layer 120. The buffer layer 120 may be omitted.

A semiconductor layer 122 is formed on the buffer layer 120. The semiconductor layer 122 may include an oxide semiconductor material or polycrystalline silicon.

When the semiconductor layer 122 includes the oxide semiconductor material, a light-shielding pattern (not shown) may be formed under the semiconductor layer 122. The light to the semiconductor layer 122 is shielded or blocked by the light-shielding pattern such that thermal degradation of the semiconductor layer 122 can be prevented. On the other hand, when the semiconductor layer 122 includes polycrystalline silicon, impurities may be doped into both sides of the semiconductor layer 122.

A gate insulating layer 124 is formed on the semiconductor layer 122. The gate insulating layer 124 may be formed of an inorganic insulating material such as silicon oxide or silicon nitride.

A gate electrode 130, which is formed of a conductive material, e.g., metal, is formed on the gate insulating layer 124 to correspond to a center of the semiconductor layer 122.

In FIG. 2, the gate insulating layer 124 is formed on an entire surface of the substrate 110. Alternatively, the gate insulating layer 124 may be patterned to have the same shape as the gate electrode 130.

An interlayer insulating layer 132, which is formed of an insulating material, is formed on the gate electrode 130. The interlayer insulating layer 132 may be formed of an inorganic insulating material, e.g., silicon oxide or silicon nitride, or an organic insulating material, e.g., benzocyclobutene or photo-acryl.

The interlayer insulating layer 132 includes first and second contact holes 134 and 136 exposing both ends of the semiconductor layer 122. The first and second contact holes 134 and 136 are positioned at both sides of the gate electrode 130 to be spaced apart from the gate electrode 130.

The first and second contact holes 134 and 136 are formed through the gate insulating layer 124. Alternatively, when the gate insulating layer 124 is patterned to have the same shape as the gate electrode 130, the first and second contact holes 134 and 136 is formed only through the interlayer insulating layer 132.

A source electrode 140 and a drain electrode 142, which are formed of a conductive material, e.g., metal, are formed on the interlayer insulating layer 132.

The source electrode 140 and the drain electrode 142 are spaced apart from each other with respect to the gate electrode 130 and respectively contact both ends of the semiconductor layer 122 through the first and second contact holes 134 and 136.

The semiconductor layer 122, the gate electrode 130, the source electrode 140 and the drain electrode 142 constitute the TFT Tr. The TFT Tr serves as a driving element. Namely, the TFT Tr may correspond to the driving TFT Td (of FIG. 1).

In the TFT Tr, the gate electrode 130, the source electrode 140, and the drain electrode 142 are positioned over the semiconductor layer 122. Namely, the TFT Tr has a coplanar structure.

Alternatively, in the TFT Tr, the gate electrode may be positioned under the semiconductor layer, and the source and drain electrodes may be positioned over the semiconductor layer such that the TFT Tr may have an inverted staggered structure. In this instance, the semiconductor layer may include amorphous silicon.

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 150, which includes a drain contact hole 152 exposing the drain electrode 142 of the TFT Tr, is formed to cover the TFT Tr.

A first electrode 160, which is connected to the drain electrode 142 of the TFT Tr through the drain contact hole 152, is separately formed in each pixel and on the planarization layer 150. The first electrode 160 may be an anode and may be formed of a conductive material, e.g., a transparent conductive oxide (TCO), having a relatively high work function. For example, the first electrode 160 may be formed of indium-tin-oxide (ITO), indium-zinc-oxide (IZO), indium-tin-zinc-oxide (ITZO), tin oxide (SnO), zinc oxide (ZnO), indium-copper-oxide (ICO) or aluminum-zinc-oxide (Al:ZnO, AZO).

When the organic light emitting display device 100 is operated in a bottom-emission type, the first electrode 160 may have a single-layered structure of the transparent conductive oxide. When the organic light emitting display device 100 is operated in a top-emission type, a reflection electrode or a reflection layer may be formed under the first electrode 160. For example, the reflection electrode or the reflection layer may be formed of silver (Ag) or aluminum-palladium-copper (APC) alloy. In this instance, the first electrode 160 may have a triple-layered structure of ITO/Ag/ITO or ITO/APC/ITO.

A bank layer 166 is formed on the planarization layer 150 to cover an edge of the first electrode 160. Namely, the bank layer 166 is positioned at a boundary of the pixel and exposes a center of the first electrode 160 in the pixel.

An organic emitting layer 162 is formed on the first electrode 160. The organic emitting layer 162 includes an emitting material layer (EML) and at least one organic layer disposed under and/or on (or over) the EML. For example, the organic layer may be a hole injection layer (HIL) disposed under the EML. In addition, the organic layer may be a p-type charge generation layer (CGL) disposed under and/or over the EML. The organic layer may further include at least one of a hole transporting layer (HTL), an electron blocking layer (EBL), a hole blocking layer (HBL), an electron transporting layer (ETL) and an electron injection layer (EIL). As described below, at least one of the HIL and the p-type CGL as the organic layer includes an indacene derivative having an asymmetric structure, where different substituents are linked (connected or combined) to both sides (ends) of an indacene core substituted with malononitrile, such that the hole is sufficiently or efficiently injected and/or transported into the EML through the organic layer.

The second electrode 164 is formed over the substrate 110 where the organic emitting layer 162 is formed. The second electrode 164 covers an entire surface of the display area and may be formed of a conductive material having a relatively low work function to serve as a cathode. For example, the second electrode 164 may be formed of aluminum (Al), magnesium (Mg), silver (Ag) or their alloy, e.g., Al—Mg alloy (AlMg) or Ag—Mg alloy (MgAg). In the top-emission type organic light emitting display device 100, the second electrode 164 may have a thin profile (small thickness) to provide a light transmittance property (or a semi-transmittance property).

Namely, one of the first and second electrodes 160 and 164 is a transparent (or semi-transparent) electrode, and the other one of the first and second electrodes 160 and 164 is a reflection electrode.

The first electrode 160, the organic emitting layer 162 and the second electrode 164 constitute the OLED D.

An encapsulation film 170 is formed on the second electrode 164 to prevent penetration of moisture into the OLED D. The encapsulation film 170 includes a first inorganic insulating layer 172, an organic insulating layer 174 and a second inorganic insulating layer 176 sequentially stacked, but it is not limited thereto. The encapsulation film 170 may be omitted.

The organic light emitting display device 100 may further include a color filter layer (not shown). The color filter layer may include a red color filter, a green color filter and a blue color filter respectively corresponding to the red pixel, the green pixel and the blue pixel. The color purity of the organic light emitting display device 100 may be improved by the color filter layer.

The organic light emitting display device 100 may further include a polarization plate (not shown) for reducing an ambient light reflection. For example, the polarization plate may be a circular polarization plate. In the bottom-emission type organic light emitting display device 100, the polarization plate may be disposed under the substrate 110. In the top-emission type organic light emitting display device 100, the polarization plate may be disposed on or over the encapsulation film 170.

In addition, in the top-emission type organic light emitting display device 100, a cover window (not shown) may be attached to the encapsulation film 170 or the polarization plate. In this instance, the substrate 110 and the cover window have a flexible property such that a flexible organic light emitting display device may be provided.

Figure 3:
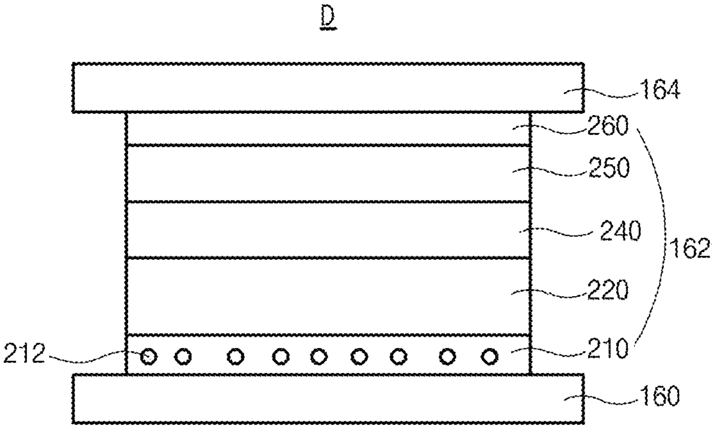
FIG. 3 is a schematic cross-sectional view of an OLED according to a second embodiment of the present disclosure.

FIG. 3 is a schematic cross-sectional view illustrating an OLED according to a second embodiment.

As shown in FIG. 3, the OLED D includes the first and second electrodes 160 and 164 facing each other and the organic emitting layer 162 between the first and second electrodes 160 and 164. The organic emitting layer 162 includes an EML 240 between the first and second electrodes 160 and 164 and an HIL 210 between the first electrode 160 and the EML 240.

The first electrode 160 is an anode, and the second electrode 164 is a cathode. One of the first and second electrodes 160 and 164 is a transparent electrode (or a semi-transparent electrode) electrode, and the other one of the first and second electrodes 160 and 164 is a reflection electrode.

The organic layer 162 may further include an EIL 260 between the second electrode 164 and the EML 240.

In addition, the organic layer 162 may further include at least one of an HTL 220 between the HIL 210 and the EML 240 and an ETL 250 between the EML 240 and the EIL 260.

Although not shown, the organic layer 162 may further include at least one of an EBL between the HTL 220 and the EML 240 and an HBL between the ETL 250 and the EML 240.

For example, the HTL 220 may include at least one compound selected from the group consisting of N,N'-diphenyl-N,N'-bis(3-methylphenyl)-1,1'-biphenyl-4,4'-diamine (TPD), N,N'-diphenyl-N,N'-bis(1-naphthyl)-1,1'-biphenyl-4,4"-diamine (NPD), 4,4'-bis(N-carbazolyl)-1,1'-biphenyl (CBP), poly[N,N'-bis(4-butylphenyl)-N,N'-bis(phenyl)-benzidine] (poly-TPD), poly[(9,9-dioctylfluorenyl-2,7-diyl)-co-(4,4'-(N-(4-sec-butylphenyl)diphenylamine))] (TFB), di-[4-(N,N-di-p-tolyl-amino)-phenyl]cyclohexane (TAPC), 3,5-di(9H-carbazol-9-yl)-N,N-diphenylaniline (DCDPA), N-(biphenyl-4-yl)-9,9-dimethyl-N-(4-(9-phenyl-9H-carbazol-3-yl)phenyl)-9H-fluoren-2-amine, and N-(biphenyl-4-yl)-N-(4-(9-phenyl-9H-carbazol-3-yl)phenyl)biphenyl-4-amine, but it is not limited thereto. For example, the HTL 220 may include NPD and may have a thickness of 500 to 1500 Å, preferably 800 to 1200 Å.

The EBL may include at least one compound selected from the group consisting of tris(4-carbazoyl-9-yl-phenyl)amine (TCTA), tris[4-(diethylamino)phenyl]amine, N-(biphenyl-4-yl)-9,9-dimethyl-N-(4-(9-phenyl-9H-carbazol-3-yl)phenyl)-9H-fluoren-2-amine, TAPC, 4,4',4"-tris(3-methylphenylamino)triphenylamine (MTDATA), 1,3-bis(carbazol-9-yl)benzene (mCP), 3,3'-bis(N-carbazolyl)-1,1'-biphenyl (mCBP), copper phthalocyanine (CuPc), N,N'-bis[4-[bis(3-methylphenyl)amino]phenyl]-N,N'-diphenyl-[1,1'-biphenyl]-4,4'-diamine (DNTPD), 1,3,5-tris[4-(diphenylamino)phenyl]benzene (TDAPB), DCDPA, and 2,8-bis(9-phenyl-9H-carbazol-3-yl)dibenzo[b,d]thiophene), but it is not limited thereto.

The HBL may include at least one compound selected from the group consisting of tris-(8-hydroxyquinolinato)aluminum ($Alq_3$), 2-biphenyl-4-yl-5-(4-t-butylphenyl)-1,3,4-oxadiazole (PBD), spiro-PBD, lithium quinolate (Liq), 2,2',2'-(1,3,5-benzinetriyl)-tris(1-phenyl-1-H benzimidazole) (TPBi), bis(2-methyl-8-quinolinolato-N1,O8)-(1,1'-biphenyl-4-phenolato)aluminum (BAlq), 4,7-diphenyl-1,10-phenanthroline (Bphen), 2,9-bis(naphthalene-2-yl)-4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPyPB), 2,4,6-tris(3'-(pyridin-3-yl)biphenyl-3-yl)1,3,5-triazine (TmPPPyTz), Poly[9,9-bis(3'-((N,N-dimethyl)-N-ethylammonium)-propyl)-2,7-fluorenel-alt-2,7-(9,9-dioctylfluorene)] (PFNBr), tris(phenylquinoxaline) (TPQ), and diphenyl-4-triphenylsilyl-phenylphosphine oxide (TSPO1), but it is not limited thereto.

The ETL 250 may include at least one compound selected from the group consisting of 1,3,5-tri(m-pyridin-3-ylphenyl)benzene (TmPyPB), 2,2',2'-(1,3,5-benzinetriyl)-tris(1-phenyl-1-H benzimidazole)(TPBi), tris(8-hydroxy-quinolinato)aluminum ($Alq_3$), 2-(4-biphenyl)-5-(4-tert-butylphenyl)-1,3,4-oxadiazole (PBD), 3-(4-biphenyl)-4-phenyl-5-tert-butylphenyl-1,2,4-triazole (TAZ), 2-biphenyl-4-yl-4,6-bis-(4'-pyridin-2-yl-biphenyl-4-yl)-[1,3,5]triazine (DPT), and bis(2-methyl-8-quinolinolate)-4-(phenylphenolato)aluminum (BAlq), but it is not limited thereto. For example, the ETL 250 may include an azine-based compound, e.g., TmPyPB, or an imidazole-based compound, e.g., TPBi, and may have a thickness of 50 to 350 Å, preferably 100 to 300 Å.

The EIL 260 may include at least one of an alkali metal, an alkali metal halide compound, such as LiF, CsF, NaF, or $BaF_2$, and an organo-metallic compound, such as Liq, lithium benzoate, or sodium stearate, but it is not limited thereto. For example, the EIL 260 may have a thickness of 1 to 50 Å, preferably 5 to 20 Å.

For example, the EML 240 of the red pixel may include a host and a dopant. In the EML 240 of the red pixel, the host may be 4,4'-bis(carbazol-9-yl)biphenyl (CBP), and the dopant may be selected from the group consisting of bis(1-phenylisoquinoline)acetylacetonate iridium (PIQIr(acac)), bis(1-phenylquinoline)acetylacetonate iridium (PQIr(acac)), tris(1-phenylquinoline)iridium (PQIr), and octaethylporphyrin platinum (PtOEP). The EML 240 in the red pixel may provide the light having a wavelength range (e.g., an emission wavelength range) of about 600 to 650 nm.

The EML 240 of the green pixel may include a host and a dopant. In the EML 240 of the green pixel, the host may be CBP, and the dopant may be tris(2-phenylpyridine)iridium ($Ir(ppy)_3$) or tris(8-hydroxyquinolino)aluminum ($Alq_3$). The EML 240 in the green pixel may provide the light having a wavelength range of about 510 to 570 nm.

The EML 240 of the blue pixel may include a host and a dopant. In the EML 240 of the blue pixel, the host may be an anthracene derivative, and the dopant may be a pyrene derivative. For example, the host may be 9,10-di(naphtha-2-yl)anthracene, and the dopant may be 1,6-bis(diphenylamino)pyrene. In the EML 240 of the blue pixel, the dopant may have a weight % of 0.1 to 20, preferably 1 to 10. The EML 240 in the blue pixel may have a thickness of 50 to 350 Å, preferably 100 to 300 Å and may provide the light having a wavelength range of about 440 to 480 nm.

The HIL 210 includes an organic compound of the present disclosure being an indacene derivative having an asymmetric structure, where different substituents are linked (connected or combined) to both sides (ends) of an indacene core substituted with malononitrile, as a hole injection material 212. The organic compound of the present disclosure is represented by Formula 1-1.

[Formula 1-1]

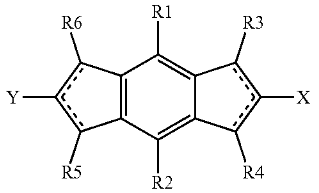

In Formula 1-1, each of R1 and R2 is independently selected from the group consisting of hydrogen (H), deuterium (D), halogen and cyano. Each of R3 to R6 is independently selected from the group consisting of halogen, cyano, malononitrile, C1 to C10 haloalkyl group and C1 to C10 haloalkoxy group, and at least one of R3 and R4 and at least one of R5 and R6 are malononitrile. Each of X and Y is independently phenyl substituted with at least one of C1 to C10 alkyl group, halogen, cyano, malononitrile, C1 to C10 haloalkyl group and C1 to C10 haloalkoxy group, and X and Y have a difference in at least one of a substituent and a position of a substituent.

For example, the C1 to C10 haloalkyl group may be trifluoromethyl, and the C1 to C10 haloalkoxy group may be trifluoromethoxy. In addition, halogen may be one of F, Cl, Br and I.

In Formula 1-1, one of R3 and R4 and one of R5 and R6 may be malononitrile, and the other one of R3 and R4 and the other one of R5 and R6 maybe cyano.

For example, in Formula 1-1, R3 and R6 may be malononitrile. Alternatively, in Formula 1-1, R4 and R6 may be malononitrile. Namely, the organic compound in Formula 1-1 may be represented by Formula 1-2 or 1-3.

[Formula 1-2]

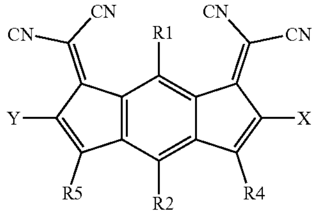

[Formula 1-3]

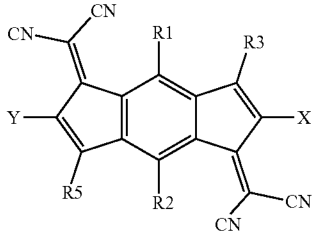

As described above, X and Y have a difference in at least one of the substituent and the position of the substituent. Namely, a phenyl moiety being X and a phenyl moiety being Y may have different substituents and/or may have same substituent or different substituents at different positions.

For example, the organic compound in Formula 1-1 may be represented by Formula 1-4.

[Formula 1-4]

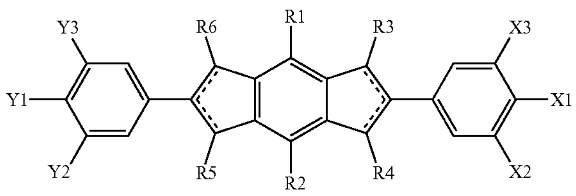

In Formula 1-4, each of X1 to X3 and each of Y1 to Y3 are independently selected from the group consisting of H, C1 to C10 alkyl group, halogen, cyano, malononitrile, C1 to C10 haloalkyl group and C1 to C10 haloalkoxy group and satisfy at least one of i) X1 and Y1 are different and ii) X2 is different from Y2 and Y3 or X3 is different from Y2 and Y3.

The organic compound of the present disclosure may be one of the compounds in Formula 2.

[Formula 2]

1

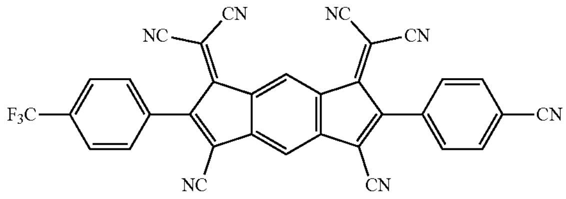

2

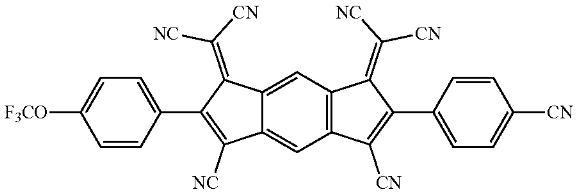

3

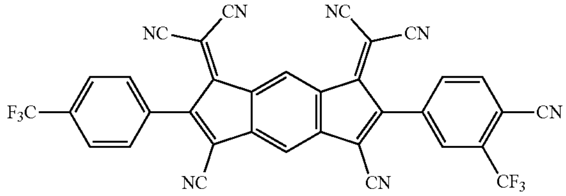

4

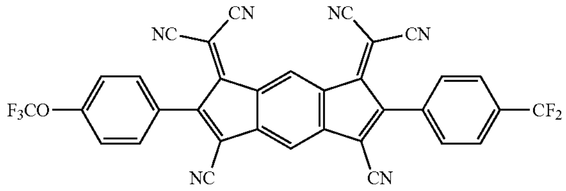

5

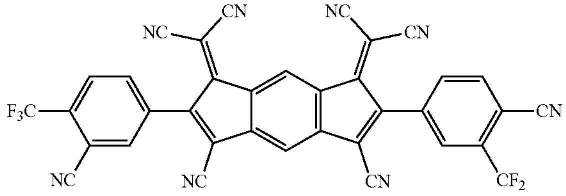

6

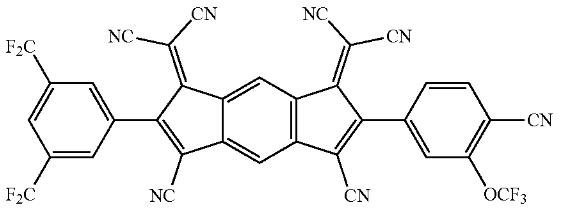

7

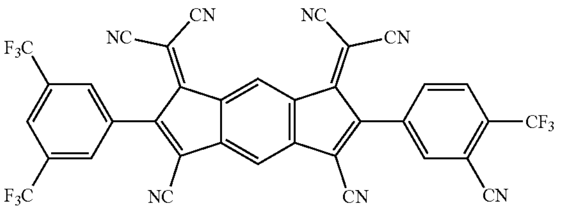

-continued
8
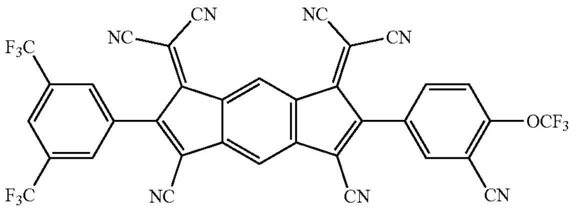
9
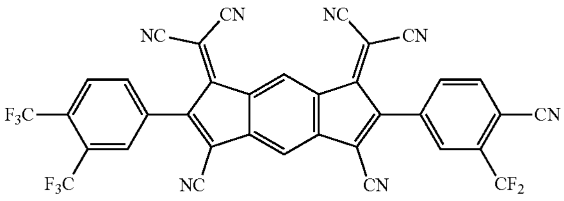
10
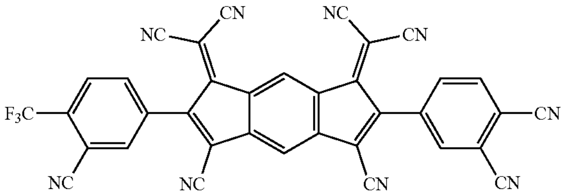
11
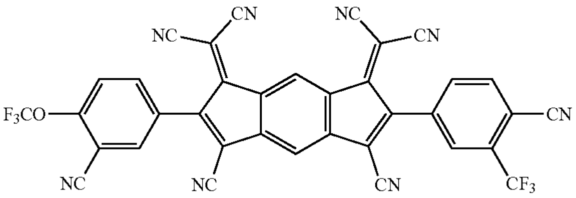
12
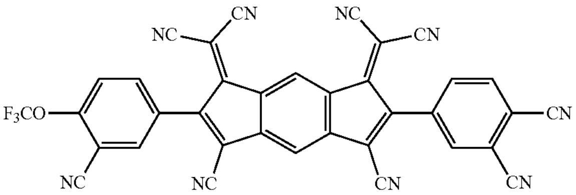
13
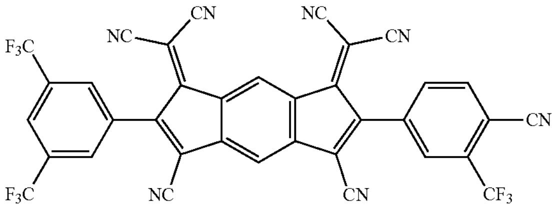
14
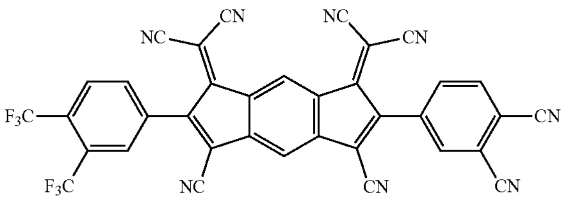
-continued
15
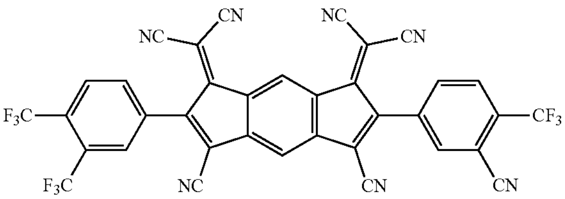
16
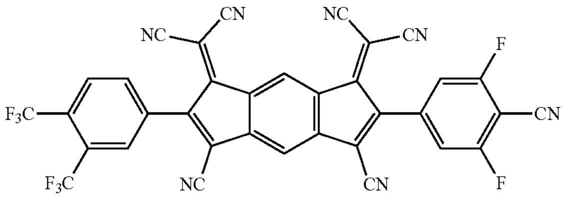
17
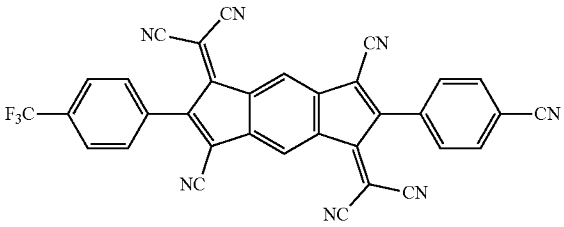
18
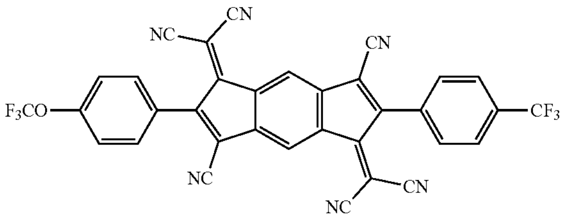
19
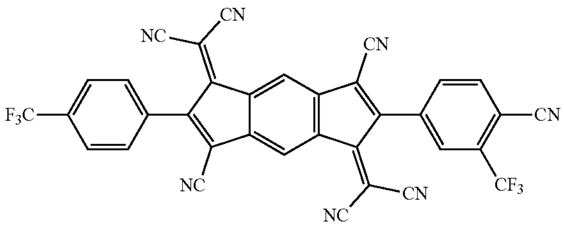
20
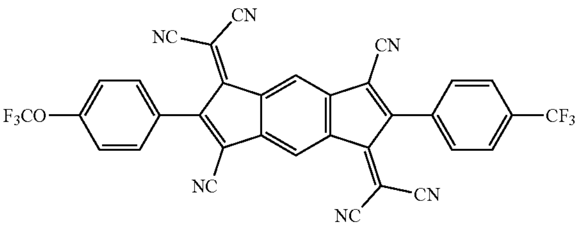

-continued
21
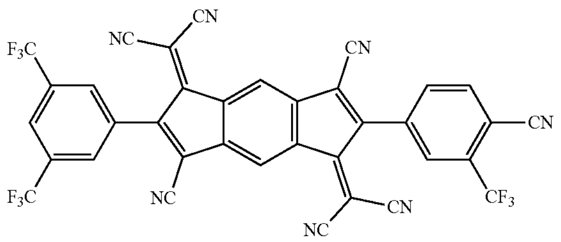
22
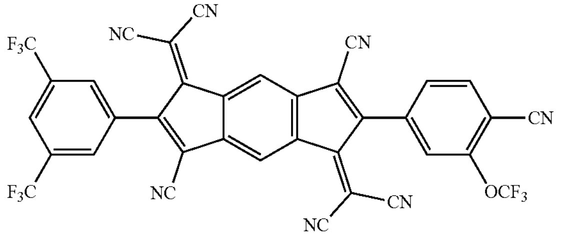
23
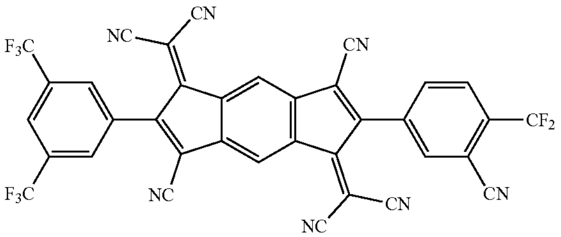
24
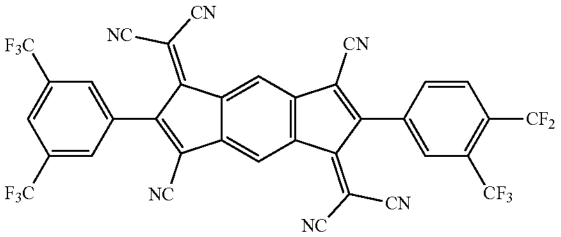
25
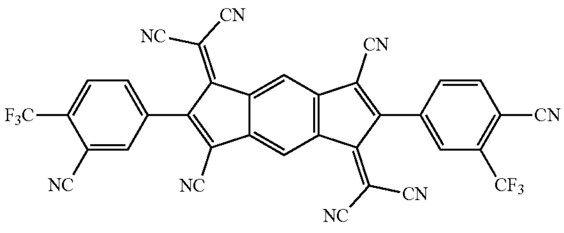
26
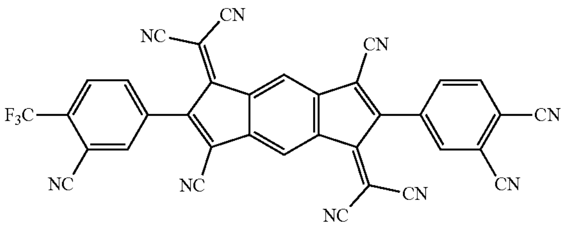
-continued
27
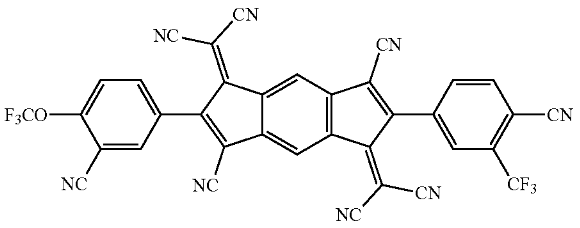
31
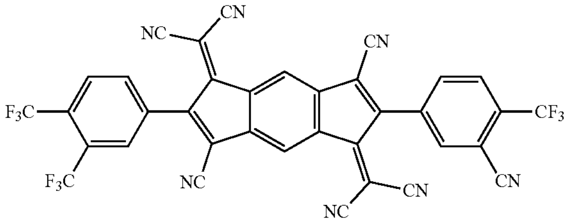
32
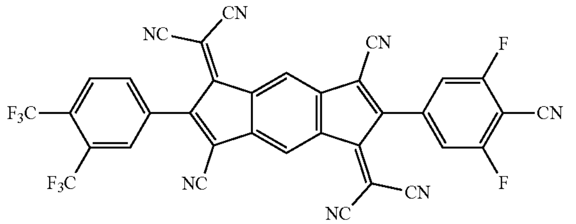
33
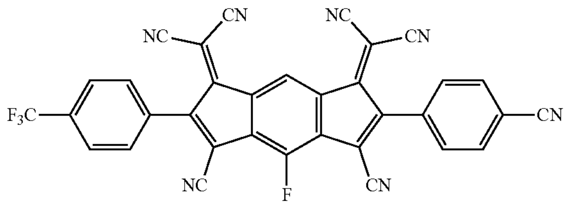
34
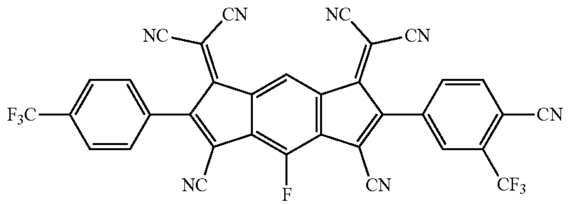
35
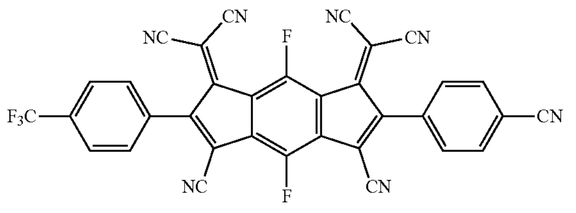

-continued
36
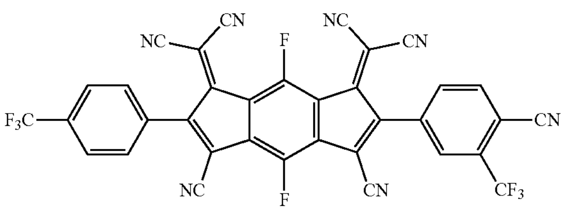
37
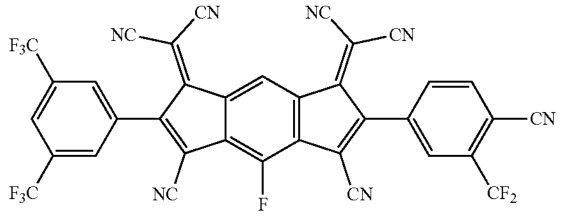
38
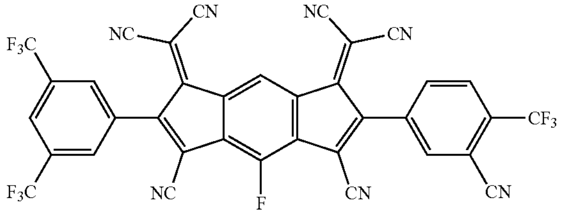
39
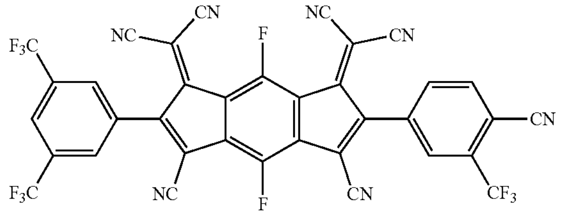
40
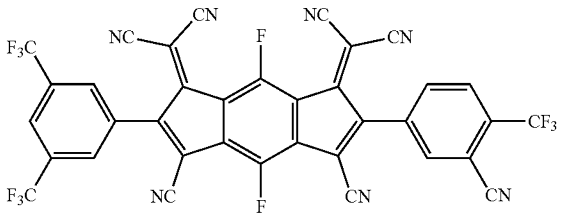
41
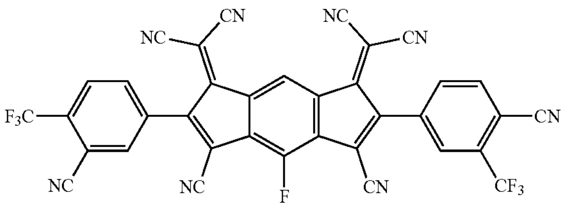
-continued
42
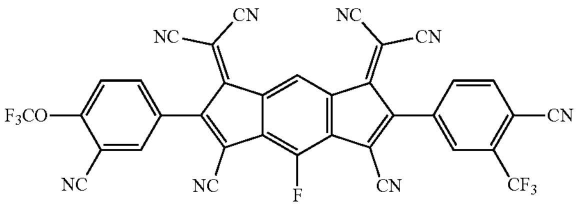
43
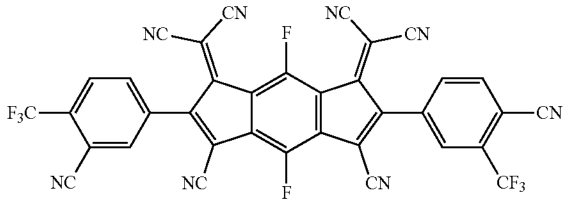
44
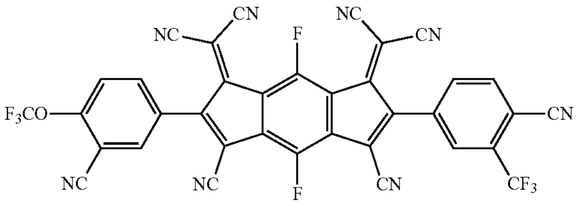
45
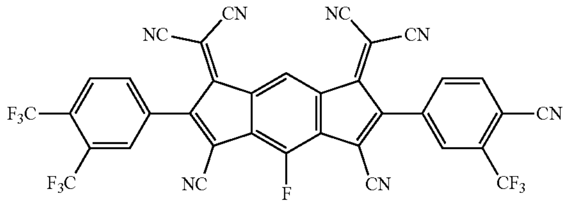
46
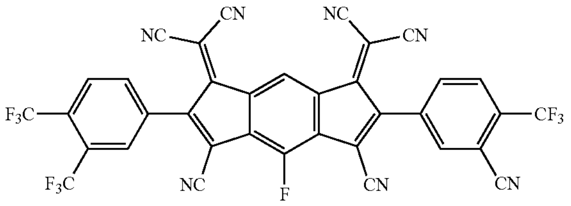
47
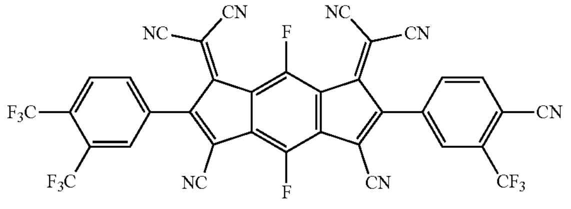
48
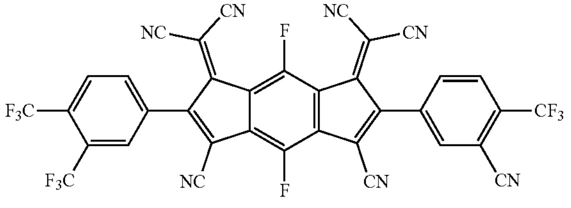

-continued
49
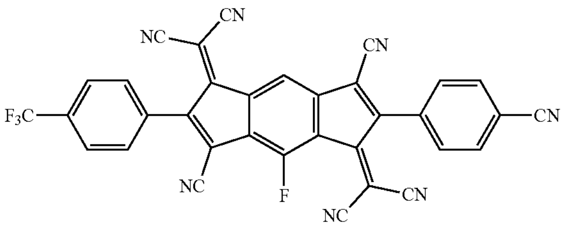
50
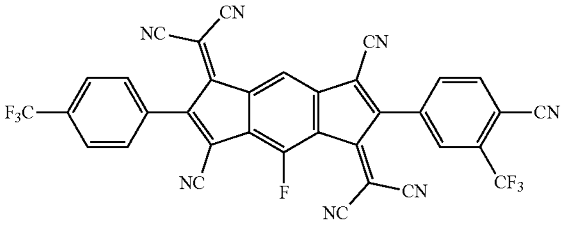
51
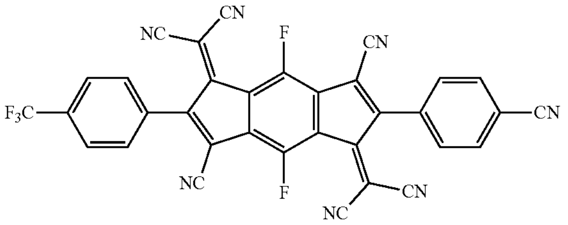
52
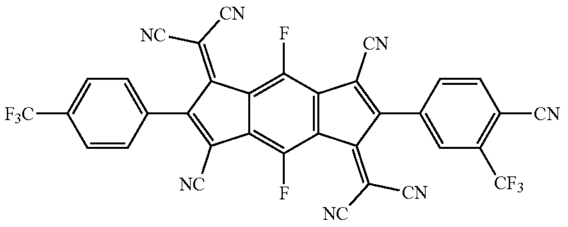
53
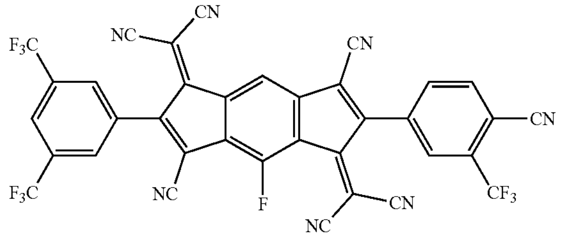
54
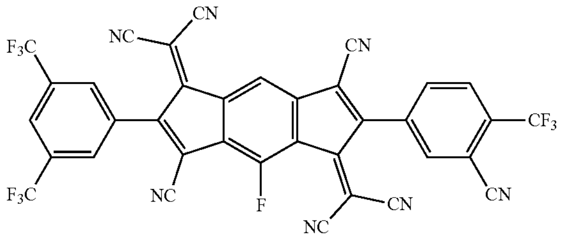
-continued
55
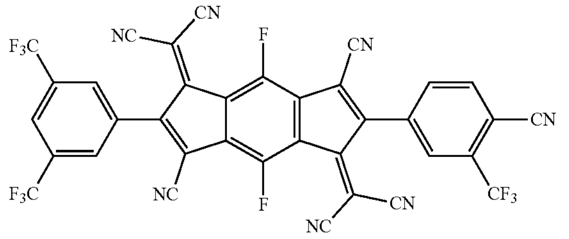
56
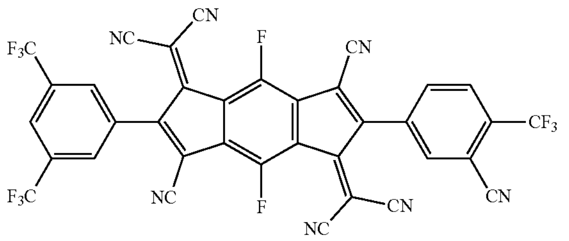
57
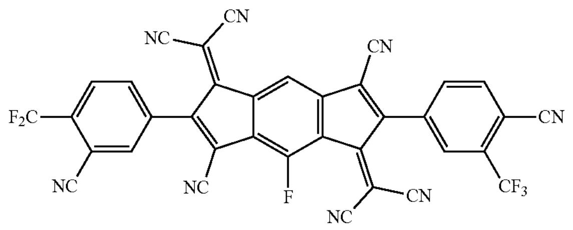
58
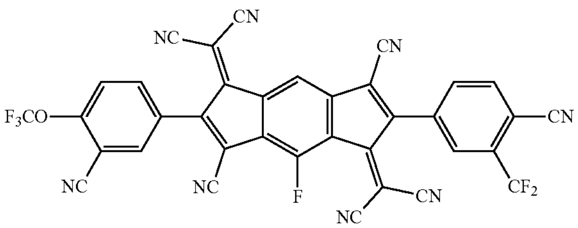
59
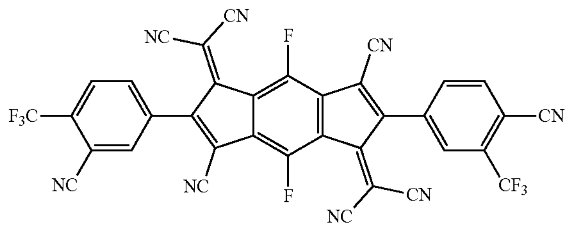
60
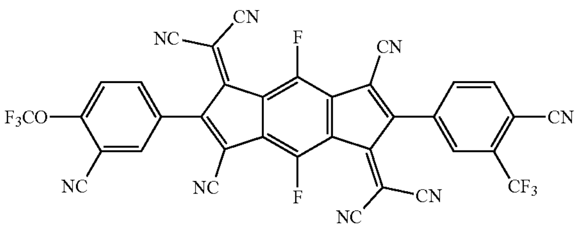

-continued
61
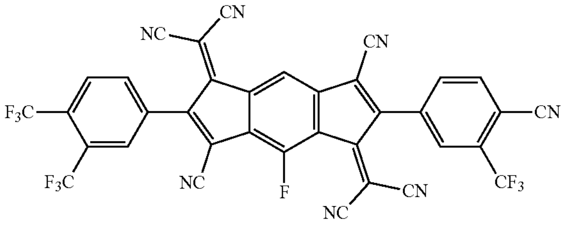
62
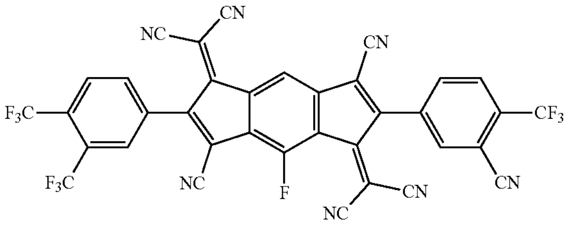
63
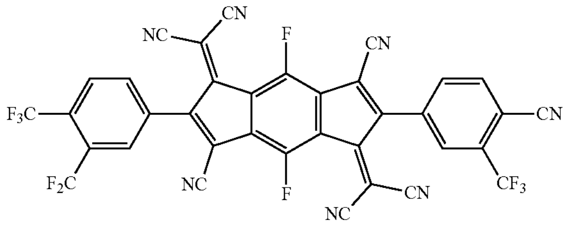
64
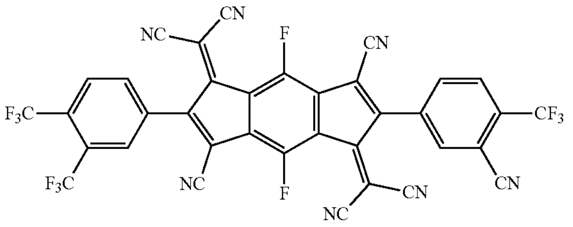
65
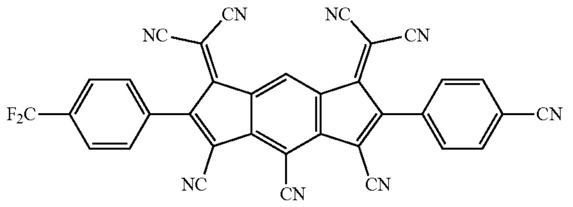
66
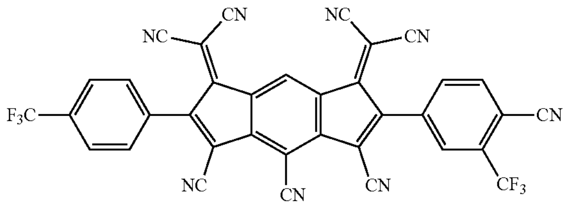
-continued
67
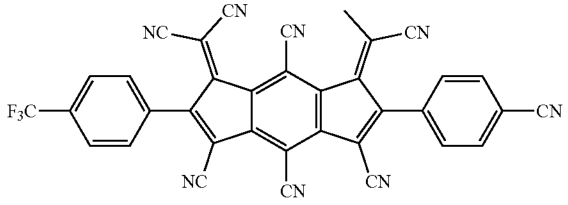
68
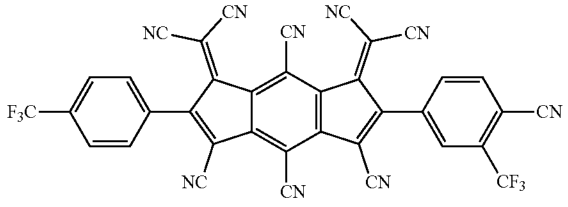
69
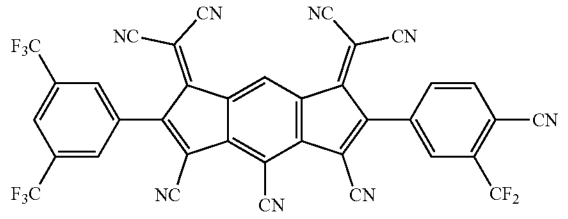
70
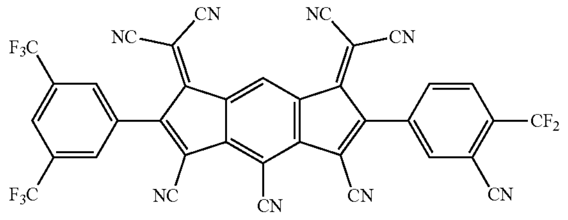
71
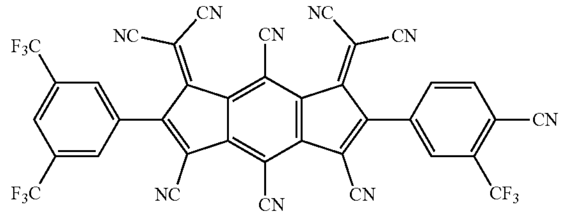
72
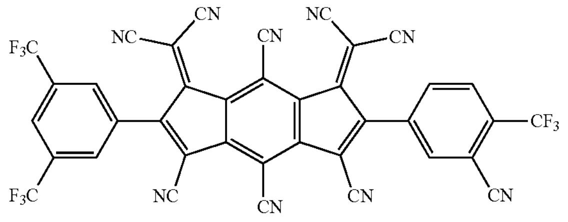

-continued
73
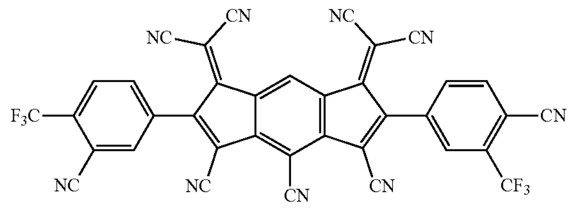
74
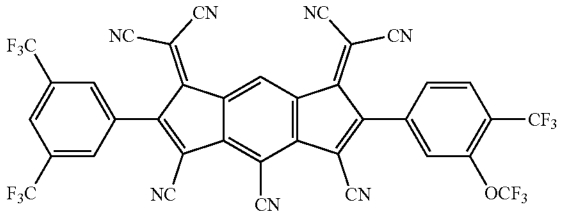
75
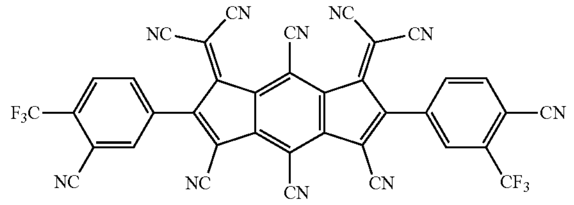
76
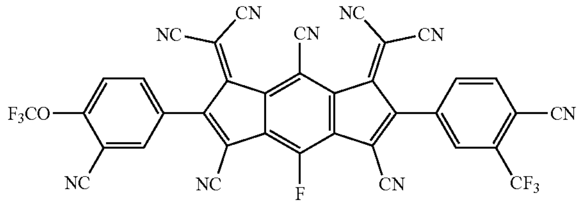
77
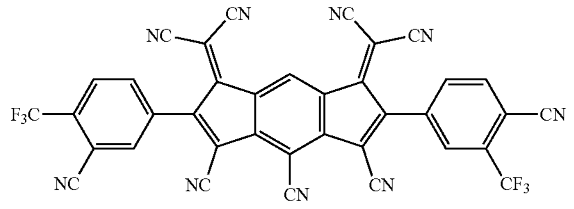
78
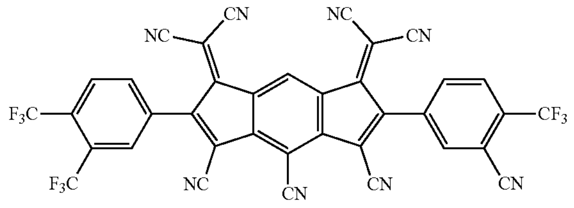
79
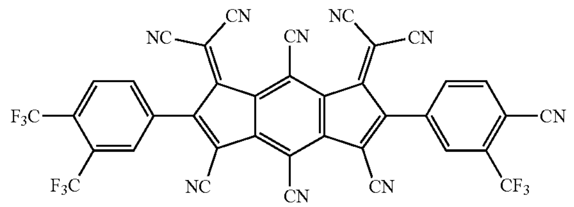
-continued
80
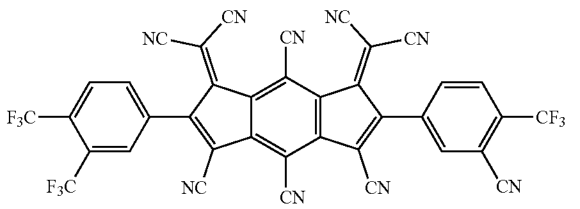
81
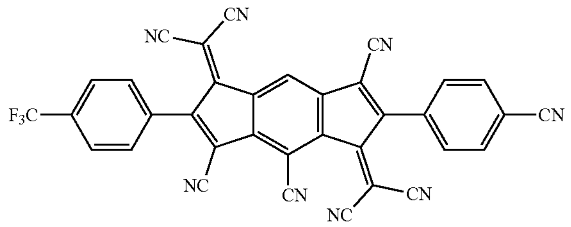
82
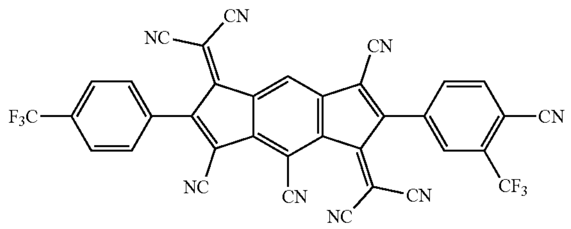
83
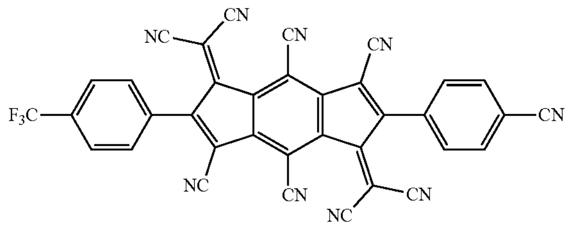
84
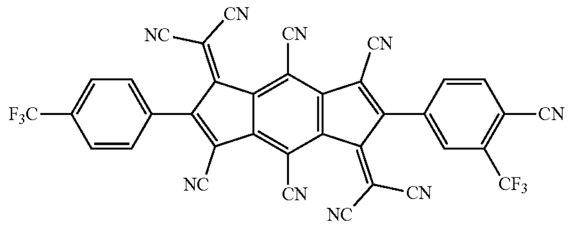
85
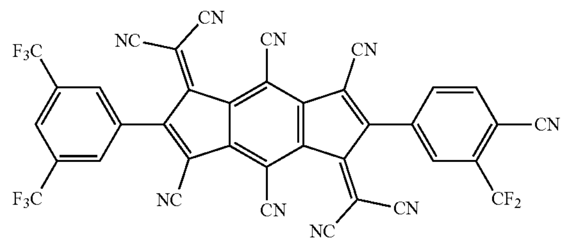

-continued
86
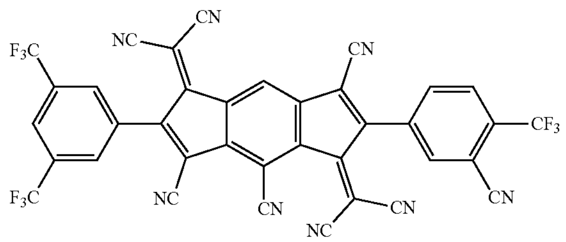
87
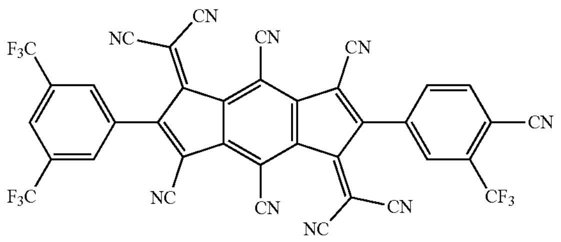
88
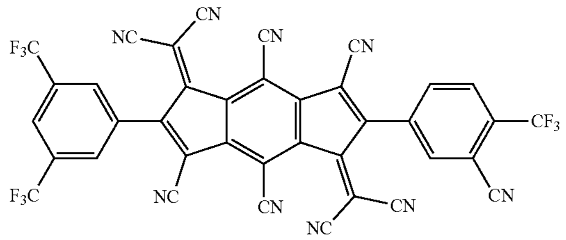
89
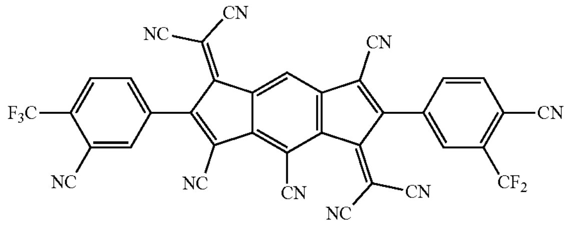
90
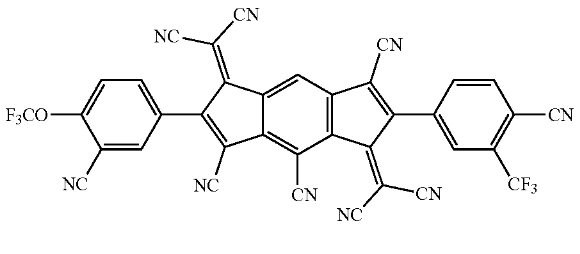
91
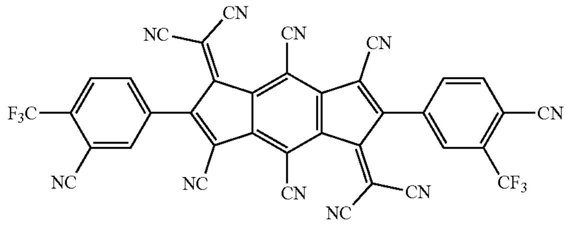
-continued
92
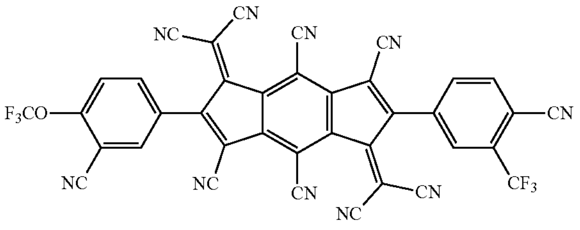
93
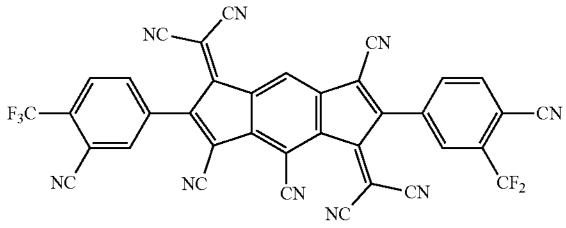
94
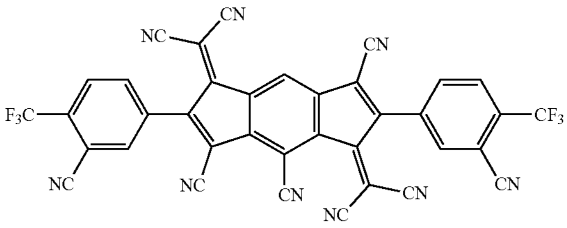
95
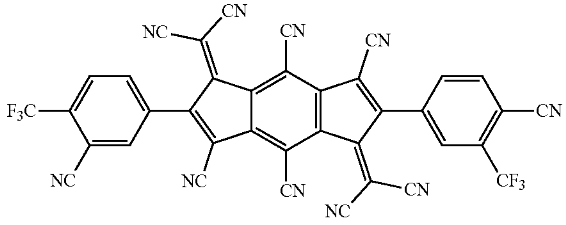
96
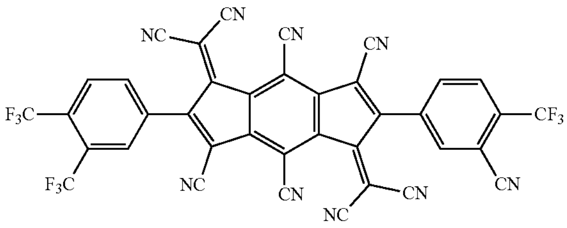
[Synthesis]
1. Synthesis of the Compound 4
(1) Compound 4-A
[Reaction Formula 1-1]
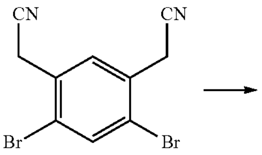

-continued

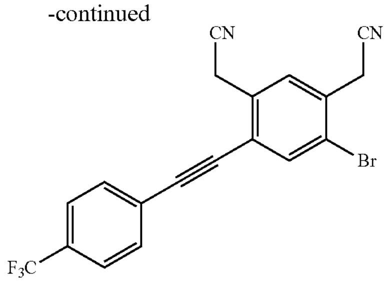

4-A 2,2'-(4,6-dibromo-1,3-phenylene)diacetonitrile (180 g, 573 mmol), toluene (6 L), copperiodide (CuI, 44 mmol), tetrakis(triphenylphosphine)palladium (44 mmol), diisopropylamine (2885 mmol) and 1-ethynyl-4-(trifluoromethyl) benzene (637 mmol) were mixed and heated to 100° C. After the reaction, the solvent (5 L) was distilled off. The mixture was cooled to room temperature and filtered to obtain a solid. After the solid was dissolved in chloroform and extracted with water, magnesium sulfate and acid clay were added and stirred for 1 hour. The mixture was filtered and the solvent was distilled again. The mixture was recrystallized using ethanol to obtain the compound 4-A (104 g). (yield 45%, MS[M+H]+=403)

(2) Compound 4-B

[Reaction Formula 1-2]

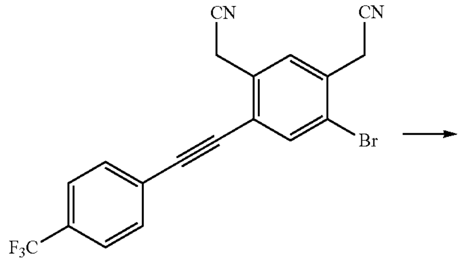

4-A

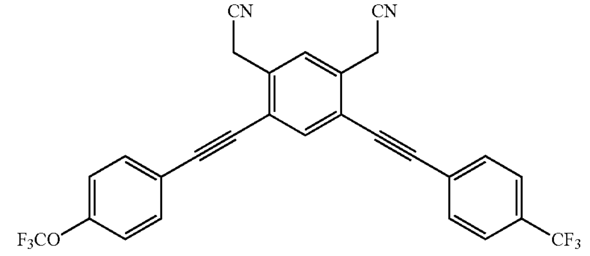

4-B

The compound 4-A (104 g, 258 mmol), toluene (3 L), CuI (21 mmol), tetrakis(triphenylphosphine)palladium (21 mmol), diisopropylamine (1290 mmol) and 1-ethynyl-4-(trifluoromethoxy)benzene (258 mmol) were mixed, heated to 100° C., and stirred for 2 hours. After the reaction, the solvent (2 L) was distilled off. The mixture was cooled to room temperature and filtered to obtain a solid. After the solid was dissolved in chloroform and extracted with water, magnesium sulfate and acid clay were added and stirred for 1 hour. After filtering the mixture, the solvent was distilled again. The mixture was recrystallized using tetrahydrofuran and ethanol to obtain the compound 4-B (39.3 g). (yield 30%, MS[M+H]+=509).

(3) Compound 4-C

[Reaction Formula 1-3]

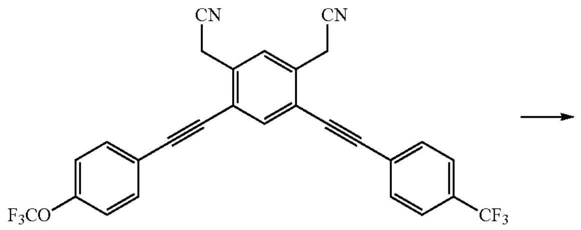

4-B

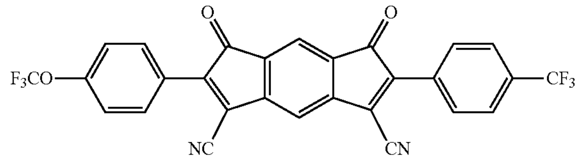

4-C

The compound 4-B (39 g, 77 mmol), 1,4-dioxane (520 mL), diphenyl sulfoxide (462 mmol), cupro bromide (II) (CuBr(II), 15 mmol), palladium acetate (15 mmol) were mixed, heated to 100° C., and stirred for 5 hours. After the reaction, the solvent was distilled off. After dissolving the mixture in chloroform, acid clay was added and stirred for 1 hour. After filtering the mixture, the solvent was distilled again. The mixture was reverse-precipitated using hexane to obtain a solid. The solid was recrystallized using tetrahydrofuran and hexane and filtered to obtain the compound 4-C (7 g). (yield 17%, MS[M+H]+=537)

(4) Compound 4

[Reaction Formula 1-4]

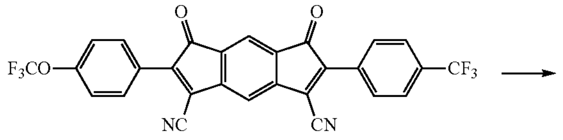

4-C

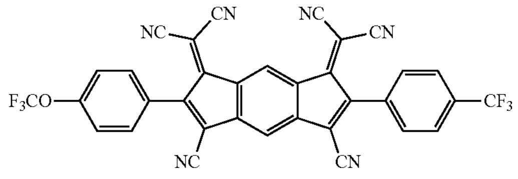

4

The compound 4-C (7 g, 13 mmol), dichloromethane (220 mL), and malononitrile (96 mmol) were added and cooled to 0° C. Titanium chloride (IV) (65 mmol) was slowly added and stirred for 1 hour while maintaining at 0° C. Pyridine (97.5 mmol) dissolved in dichloromethane (75 mL) was slowly added into the mixture at 0° C. and stirred for 1 hour. After the reaction was completed, acetic acid (130 mmol) was added and additionally stirred for 30 minutes. After the reaction solution was extracted with water, the organic layer was reverse-precipitated in hexane to obtain a solid. After filtering the solid through acetonitrile, magnesium sulfate and acid clay were added and stirred for 30 minutes. The solution was filtered, recrystallized using acetonitrile and toluene, and washed with toluene. The solid was recrystallized using acetonitrile and tert-butylmethylether and purified by sublimation to obtain the compound 4 (1.6 g). (yield 20%, MS[M+H]+=633)

2. Synthesis of the Compound 13

(1) Compound 13-A

[Reaction Formula 2-1]

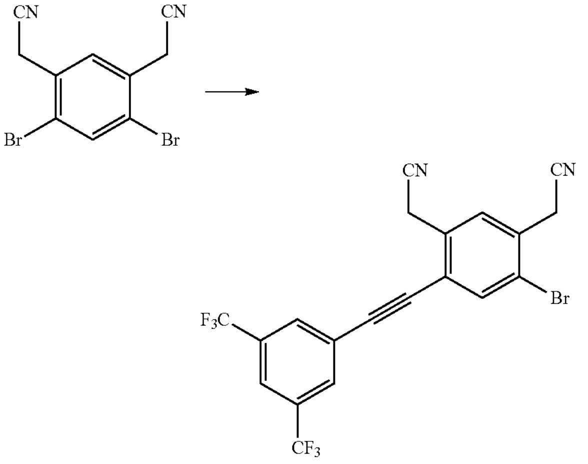

13-A 2,2'-(4,6-dibromo-1,3-phenylene)diacetonitrile (200 g, 637 mmol), toluene (6 L), copperiodide (CuI, 51 mmol), tetrakis(triphenylphosphine)palladium (51 mmol), diisopropylamine (3185 mmol) and 1-ethynyl-3,5-bis(trifluoromethyl)benzene (637 mmol) were mixed and heated to 100° C. After the reaction, the solvent (5 L) was distilled off. The mixture was cooled to room temperature and filtered to obtain a solid. After the solid was dissolved in chloroform and extracted with water, magnesium sulfate and acid clay were added and stirred for 1 hour. The mixture was filtered and the solvent was distilled again. The mixture was recrystallized using ethanol to obtain the compound 13-A (105 g). (yield 35%, MS[M+H]+=471)

(2) Compound 13-B

[Reaction Formula 2-2]

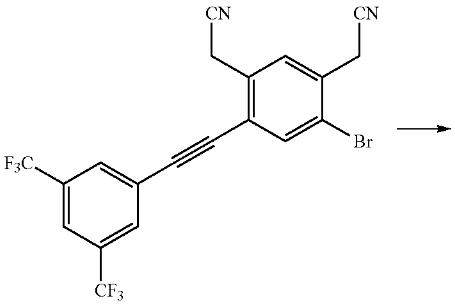

13-A

-continued

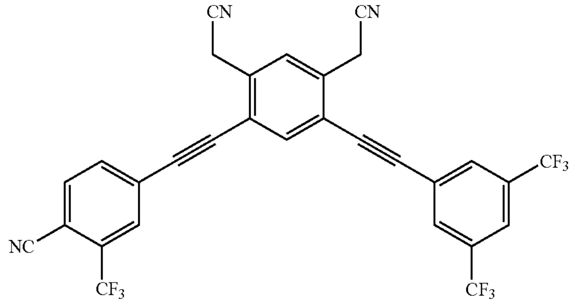

13-B

The compound 13-A (105 g, 223 mmol), toluene (3 L), CuI (18 mmol), tetrakis(triphenylphosphine)palladium (18 mmol), diisopropylamine (1115 mmol) and 4-ethynyl-2-(trifluoromethyl)benzonitrile (223 mmol) were mixed, heated to 100° C., and stirred for 2 hours. After the reaction, the solvent (2 L) was distilled off. The mixture was cooled to room temperature and filtered to obtain a solid. After the solid was dissolved in chloroform and extracted with water, magnesium sulfate and acid clay were added and stirred for 1 hour. After filtering the mixture, the solvent was distilled again. The mixture was recrystallized using tetrahydrofuran and ethanol to obtain the compound 13-B (32.6 g). (yield 25%, MS[M+H]+=586)

(4) Compound 13-C

[Reaction Formula 2-3]

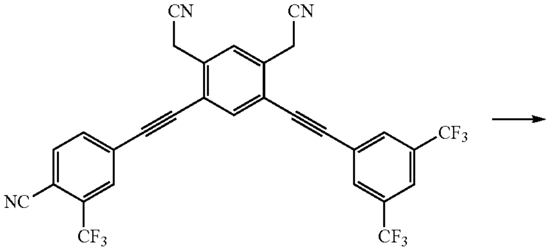

13-B

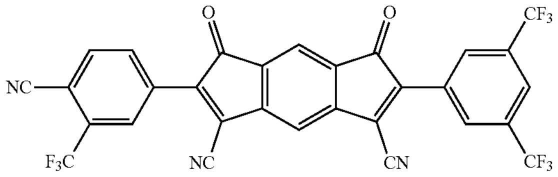

13-C

The compound 13-B (32 g, 55 mmol), 1,4-dioxane (480 mL), diphenyl sulfoxide (330 mmol), CuBr(II) (11 mmol), palladium acetate (11 mmol) were mixed, heated to 100° C., and stirred for 5 hours. After the reaction, the solvent was distilled off. After dissolving the mixture in chloroform, acid clay was added and stirred for 1 hour. After filtering the mixture, the solvent was distilled again. The mixture was reverse-precipitated using hexane to obtain a solid. The solid was recrystallized using tetrahydrofuran and hexane and filtered to obtain the compound 13-C (5 g). (yield 15%, MS[M+H]+=614)

(4) Compound 13

[Reaction Formula 2-4]

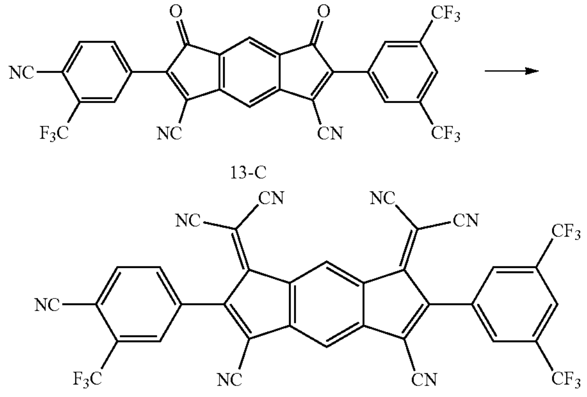

13-C

13

The compound 13-C (5 g, 8.2 mmol), dichloromethane (150 mL), and malononitrile (49.2 mmol) were added and cooled to 0° C. Titanium chloride (IV) (41 mmol) was slowly added and stirred for 1 hour while maintaining at 0° C. Pyridine (61.5 mmol) dissolved in dichloromethane (50 mL) was slowly added into the mixture at 0° C. and stirred for 1 hour. After the reaction was completed, acetic acid (82 mmol) was added and additionally stirred for 30 minutes. After the reaction solution was extracted with water, the organic layer was reverse-precipitated in hexane to obtain a solid. After filtering the solid through acetonitrile, magnesium sulfate and acid clay were added and stirred for 30 minutes. The solution was filtered, recrystallized using acetonitrile and toluene, and washed with toluene. The solid was recrystallized using acetonitrile and tert-butylmethylether and purified by sublimation to obtain the compound 13 (1 g). (yield 18%, MS[M+H]+=710)

3. Synthesis of the Compound 37

(1) Compound 37-A

[Reaction Formula 3-1]

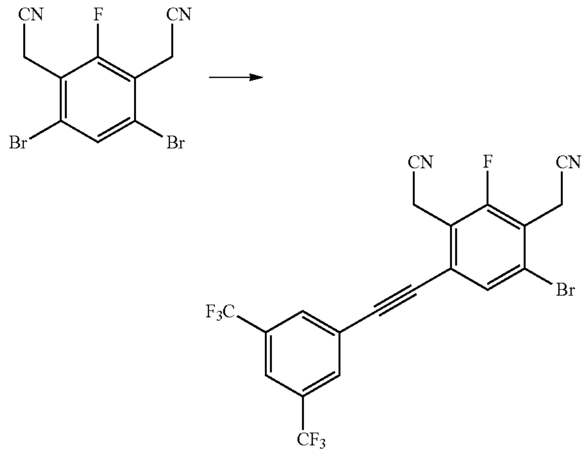

37-A 2,2'-(4,6-dibromo-2-fluoro-1,3-phenylene)diacetonitrile (300 g, 903.7 mmol), toluene (9 L), CuI (72.3 mmol), tetrakis(triphenylphosphine)palladium (72.3 mmol), diisopropylamine (4518 mmol) and 1-ethynyl-3,5-bis(trifluoromethyl)benzene (903.7 mmol) were mixed and heated to 100° C. After the reaction, the solvent (8 L) was distilled off. The mixture was cooled to room temperature and filtered to obtain a solid. After the solid was dissolved in chloroform and extracted with water, magnesium sulfate and acid clay were added and stirred for 1 hour. The mixture was filtered and the solvent was distilled again. The mixture was recrystallized using ethanol to obtain the compound 37-A (137 g). (yield 31%, MS[M+H]+=489)

(2) Compound 37-B

[Reaction Formula 3-2]

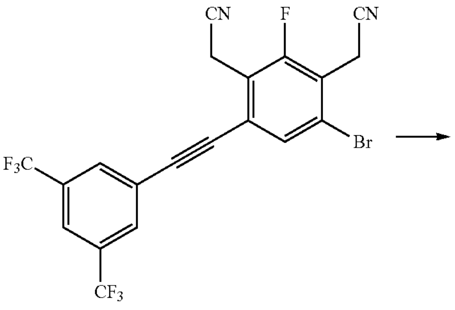

37-A

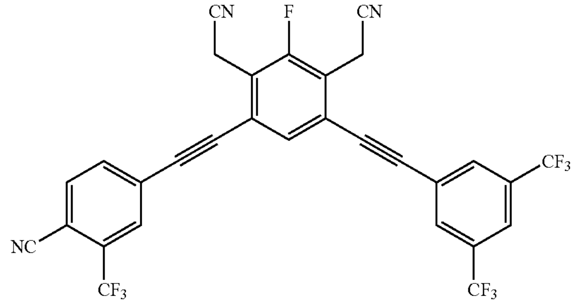

37-B

The compound 37-A (137 g, 280 mmol), toluene (4.1 L), Cut (22 mmol), tetrakis(triphenylphosphine)palladium (22 mmol), diisopropylamine (1400 mmol) and 4-ethynyl-2-(trifluoromethyl)benzonitrile (280 mmol) were mixed, heated to 100° C., and stirred for 2 hours. After the reaction, the solvent (3 L) was distilled off. The mixture was cooled to room temperature and filtered to obtain a solid. After the solid was dissolved in chloroform and extracted with water, magnesium sulfate and acid clay were added and stirred for 1 hour. After filtering the mixture, the solvent was distilled again. The mixture was recrystallized using tetrahydrofuran and ethanol to obtain the compound 37-B (33.8 g). (yield 20%, MS[M+H]+=603)

(3) Compound 37-C

[Reaction Formula 3-3]

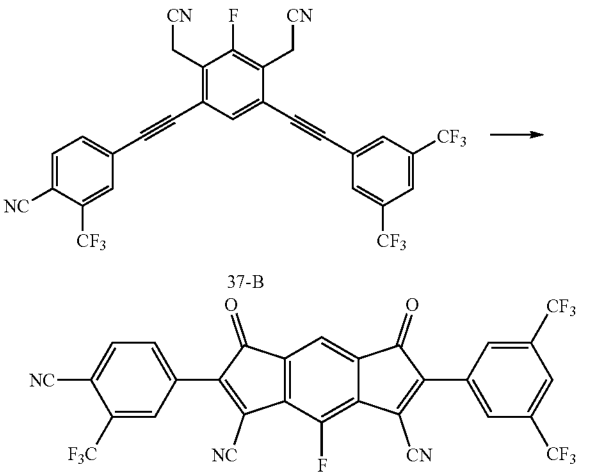

37-B

37-C

The compound 37-B (33 g, 54.7 mmol), 1,4-dioxane (500 mL), diphenyl sulfoxide (328.2 mmol), CuBr(II) (10.9 mmol), palladium acetate (10.9 mmol) were mixed, heated to 100° C., and stirred for 5 hours. After the reaction, the solvent was distilled off. After dissolving the mixture in chloroform, acid clay was added and stirred for 1 hour. After filtering the mixture, the solvent was distilled again. The mixture was reverse-precipitated using hexane to obtain a solid. The solid was recrystallized using tetrahydrofuran and hexane and filtered to obtain the compound 37-C (4.8 g). (yield 14%, MS[M+H]+=632)

(4) Compound 37

[Reaction Formula 3-4]

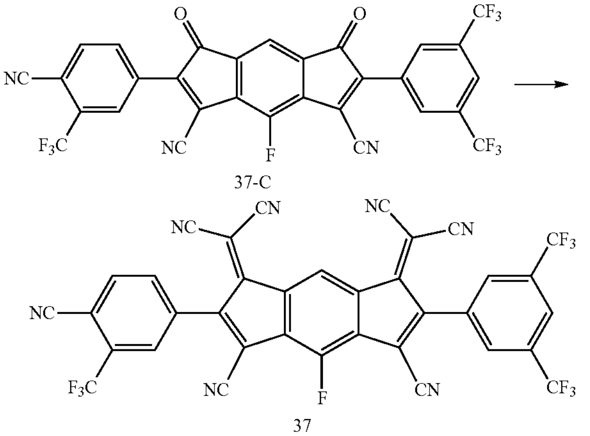

37-C

37

The compound 37-C (4.8 g, 7.6 mmol), dichloromethane (145 mL), and malononitrile (45.6 mmol) were added and cooled to 0° C. Titanium chloride (IV) (38 mmol) was slowly added and stirred for 1 hour while maintaining at 0° C. Pyridine (57 mmol) dissolved in dichloromethane (48 mL) was slowly added into the mixture at 0° C. and stirred for 1 hour. After the reaction was completed, acetic acid (76 mmol) was added and additionally stirred for 30 minutes. After the reaction solution was extracted with water, the organic layer was reverse-precipitated in hexane to obtain a solid. After filtering the solid through acetonitrile, magnesium sulfate and acid clay were added and stirred for 30 minutes. The solution was filtered, recrystallized using acetonitrile and toluene, and washed with toluene. The solid was recrystallized using acetonitrile and tert-butylmethylether and purified by sublimation to obtain the compound 37 (1.1 g). (yield 20%, MS[M+H]+=728)

The HIL 210 may further include an electron injection host material. Namely, the HIL 210 may include only the organic compound of the present disclosure as the hole injection material 212 or may include a mixture of the hole injection material 212 and the hole injection host material.

For example, the hole injection host material may be at least one selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPD), 1,4,5,8,9,11-hexaazatriphenylenehexacarbonitrile (dipyrazino[2,3-f:2'3'-h]quinoxaline-2,3,6,7,10,11-hexacarbonitrile (HAT-CN), 1,3,5-tris[4-(diphenylamino)phenyl]benzene (TDAPB), poly(3,4-ethylenedioxythiphene) polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine, but it is not limited thereto. For example, the hole injection host material may be NPD. In the HIL 210, the hole injection material 212 being the organic compound of the present disclosure may have a weight % of about 1 to 40 wt %, preferably about 5 to 20 wt %.

As described above, in the OLED D of the present disclosure, the HIL 210 includes the hole injection material 210 being the organic compound of the present disclosure. The organic compound of the present disclosure has high dipole moment, e.g., above 0.8 D, preferably 1.5 D to 4 D, such that the organic compound has excellent hole injection property. Accordingly, in the OLED D with the HIL 210 including the organic compound of the present disclosure as the hole injection material 212, the driving voltage is reduced, and the emitting efficiency and the lifespan are improved.

Figure 4:
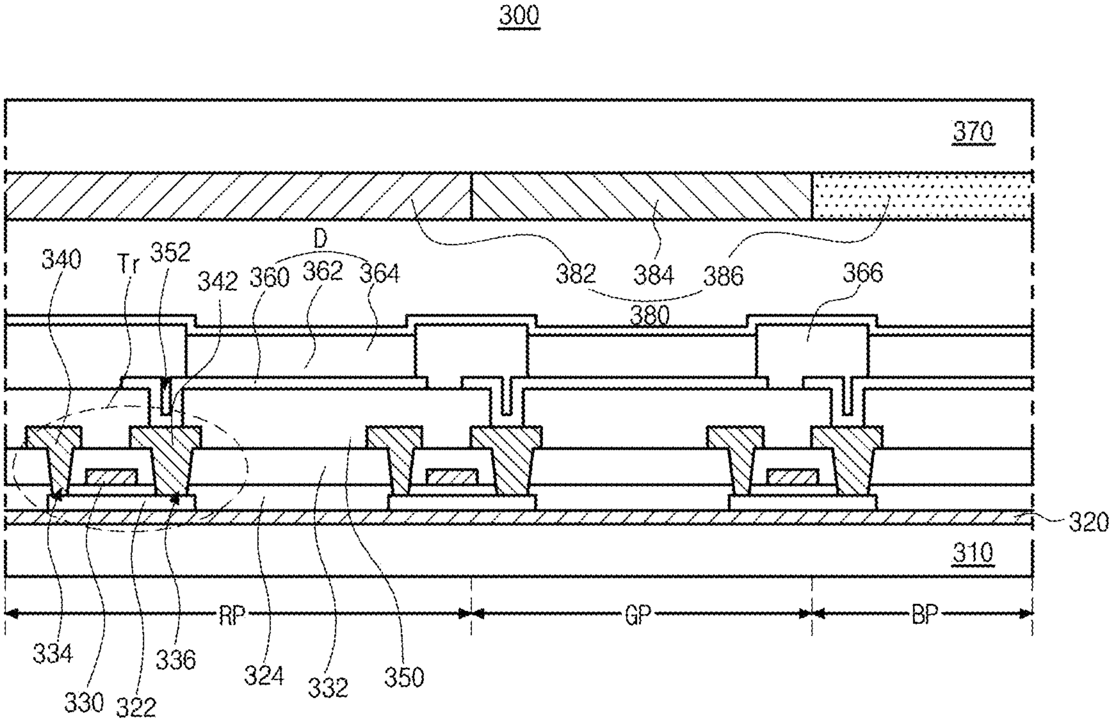
FIG. 4 is a schematic cross-sectional view of an organic light emitting device according to a third embodiment of the present disclosure.
Figure 5:
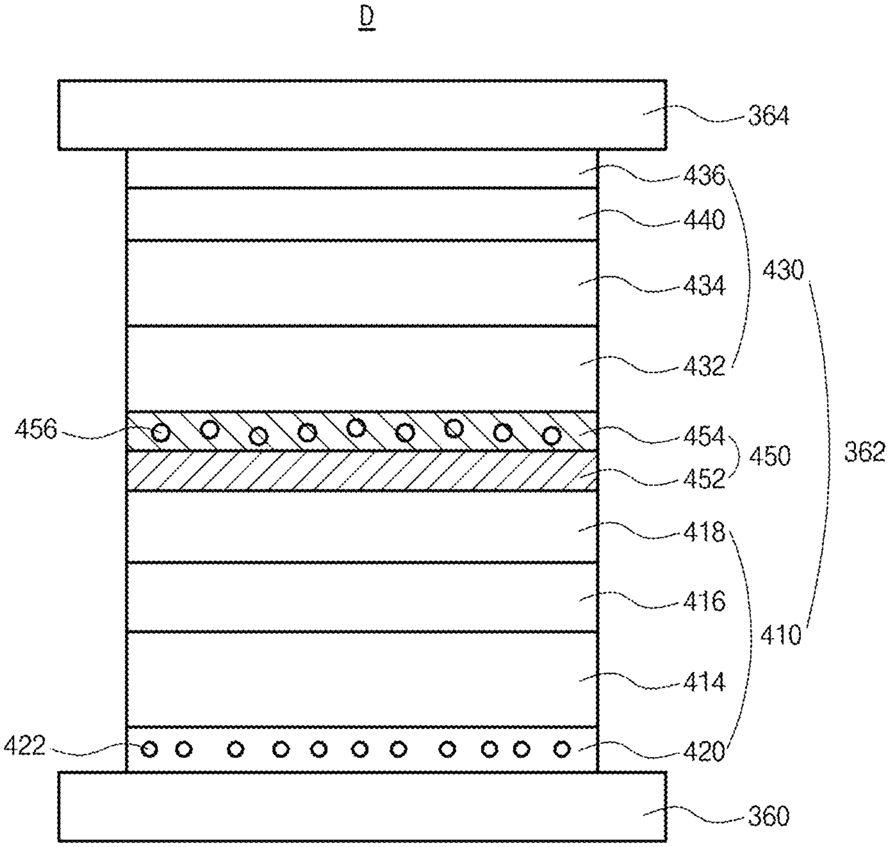
FIG. 5 is a schematic cross-sectional view of an OLED according to a fourth embodiment of the present disclosure.
Figure 6:
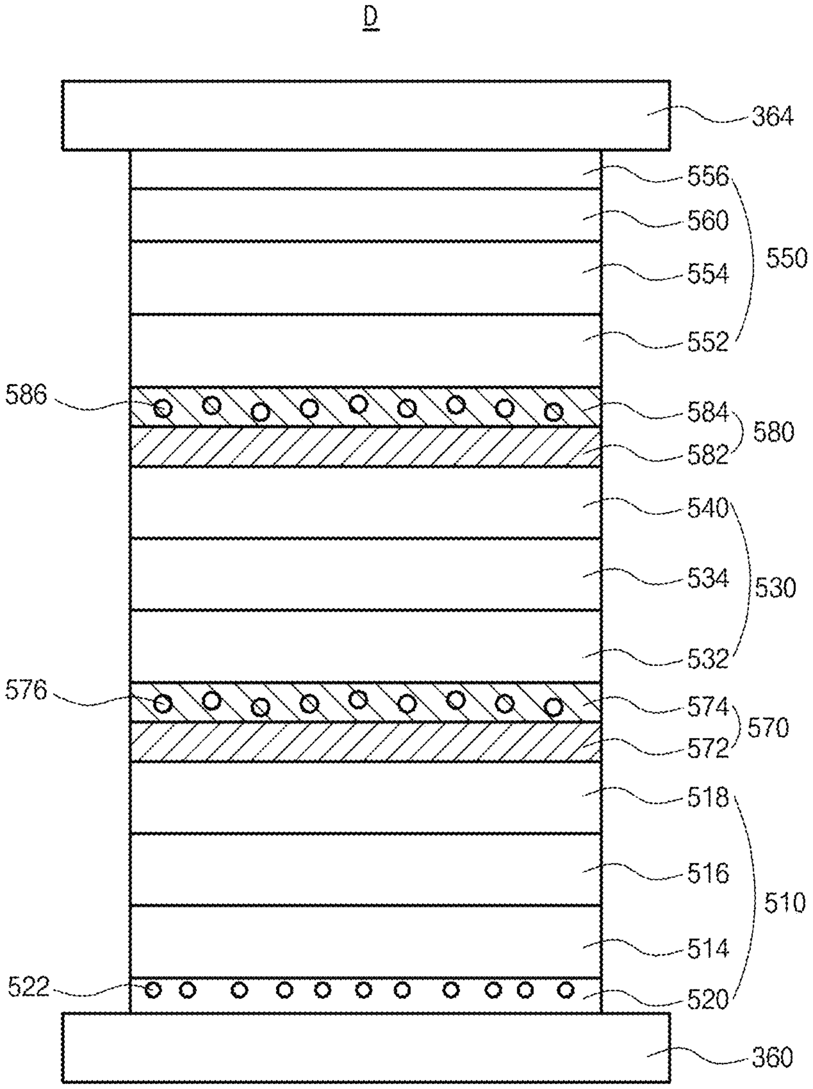
FIG. 6 is a schematic cross-sectional view of an OLED device according to a fifth embodiment of the present disclosure.

FIG. 4 is a schematic cross-sectional view of an organic light emitting device according to a third embodiment of the present disclosure. FIG. 5 is a schematic cross-sectional view of an OLED according to a fourth embodiment of the present disclosure, and FIG. 6 is a schematic cross-sectional view of an OLED device according to a fifth embodiment of the present disclosure.

As shown in FIG. 4, the organic light emitting display device 300 includes a first substrate 310, where a red pixel BP, a green pixel GP and a blue pixel BP are defined, a second substrate 370 facing the first substrate 310, an OLED D, which is positioned between the first and second substrates 310 and 370 and providing white emission, and a color filter layer 380 between the OLED D and the second substrate 370.

Each of the first and second substrates 310 and 370 may be a glass substrate or a flexible substrate. For example, each of the first and second substrates 310 and 370 may be a polyimide (PI) substrate, a polyethersulfone (PES) substrate, a polyethylenenaphthalate (PEN) substrate, a polyethylene terephthalate (PET) substrate or a polycarbonate (PC) substrate.

A buffer layer 320 is formed on the substrate, and the TFT Tr corresponding to each of the red, green and blue pixels RP, GP and BP is formed on the buffer layer 320. The buffer layer 320 may be omitted.

A semiconductor layer 322 is formed on the buffer layer 320. The semiconductor layer 322 may include an oxide semiconductor material or polycrystalline silicon.

A gate insulating layer 324 is formed on the semiconductor layer 322. The gate insulating layer 324 may be formed of an inorganic insulating material such as silicon oxide or silicon nitride.

A gate electrode 330, which is formed of a conductive material, e.g., metal, is formed on the gate insulating layer 324 to correspond to a center of the semiconductor layer 322.

An interlayer insulating layer 332, which is formed of an insulating material, is formed on the gate electrode 330. The interlayer insulating layer 332 may be formed of an inorganic insulating material, e.g., silicon oxide or silicon nitride, or an organic insulating material, e.g., benzocyclobutene or photo-acryl.

The interlayer insulating layer 332 includes first and second contact holes 334 and 336 exposing both ends of the semiconductor layer 322. The first and second contact holes 334 and 336 are positioned at both sides of the gate electrode 330 to be spaced apart from the gate electrode 330.

A source electrode 340 and a drain electrode 342, which are formed of a conductive material, e.g., metal, are formed on the interlayer insulating layer 332.

The source electrode 340 and the drain electrode 342 are spaced apart from each other with respect to the gate electrode 330 and respectively contact both ends of the semiconductor layer 322 through the first and second contact holes 334 and 336.

The semiconductor layer 322, the gate electrode 330, the source electrode 340 and the drain electrode 342 constitute the TFT Tr. The TFT Tr serves as a driving element. Namely, the TFT Tr may correspond to the driving TFT Td (of FIG. 1).

Although not shown, the gate line and the data line cross each other to define the pixel, and the switching TFT is formed to be connected to the gate and data lines. The switching TFT is connected to the TFT Tr as the driving element.

In addition, the power line, which may be formed to be parallel to and spaced apart from one of the gate and data lines, and the storage capacitor for maintaining the voltage of the gate electrode of the TFT Tr in one frame may be further formed.

A planarization layer 350, which includes a drain contact hole 352 exposing the drain electrode 342 of the TFT Tr, is formed to cover the TFT Tr.

A first electrode 360, which is connected to the drain electrode 342 of the TFT Tr through the drain contact hole 352, is separately formed in each pixel and on the planarization layer 350. The first electrode 360 may be an anode and may be formed of a conductive material, e.g., a transparent conductive oxide (TCO), having a relatively high work function. The first electrode 360 may further include a reflection electrode or a reflection layer. For example, the reflection electrode or the reflection layer may be formed of silver (Ag) or aluminum-palladium-copper (APC) alloy. In the top-emission type organic light emitting display device 300, the first electrode 360 may have a triple-layered structure of ITO/Ag/ITO or ITO/APC/ITO.

A bank layer 366 is formed on the planarization layer 350 to cover an edge of the first electrode 360. Namely, the bank layer 366 is positioned at a boundary of the pixel and exposes a center of the first electrode 360 in the pixel. Since the OLED D emits the white light in the red, green and blue pixels RP, GP and BP, the organic emitting layer 362 may be formed as a common layer in the red, green and blue pixels RP, GP and BP without separation. The bank layer 366 may be formed to prevent a current leakage at an edge of the first electrode 360 and may be omitted.

An organic emitting layer 362 is formed on the first electrode 360.

Referring to FIG. 5, the OLED D includes the first and second electrodes 360 and 364 facing each other and the organic emitting layer 362 between the first and second electrodes 360 and 364. The organic emitting layer 362 includes a first emitting part 410 including a first EML 416 and an HIL 420, a second emitting part 430 including a second EML 434 and a charge generation layer (CGL) 450 between the first and second emitting parts 410 and 430.

The CGL 450 is positioned between the first and second emitting parts 410 and 430, and the first emitting part 410, the CGL 450 and the second emitting part 430 are sequentially stacked on the first electrode 360. Namely, the first emitting part 410 is positioned between the first electrode 360 and the CGL 450, and the second emitting part 420 is positioned between the second electrode 364 and the CGL 450.

In the first emitting part 410, the HIL 420 is positioned under the first EML 416. Namely, the HIL 420 is positioned between the first electrode 360 and the first EML 416.

The first emitting part 410 may further include at least one of a first HTL 414 positioned between the HIL 420 and the first EML 416 and a first ETL 418 over the first EML 416.

Although not shown, the first emitting part 410 may further include at least one of an EBL between the first HTL 414 and the first EML 416 and an HBL between the first EML 416 and the first ETL 418.

The second emitting part 430 may further include EIL 436 over the second EML 434. In addition, the second emitting part 430 may further include at least one of a second HTL 432 under the second EML 434 and a second ETL 440 between the second EML 434 and the EIL 436.

Although not shown, the second emitting part 430 may further include at least one of an EBL between the second HTL 432 and the second EML 434 and an HBL between the second EML 434 and the second ETL 440.

One of the first and second EMLs 416 and 434 provides a light having a wavelength range of about 440 to 480 nm, and the other one of the first and second EMLs 416 and 434 provides a light having a wavelength range of about 500 to 550 nm. For example, the first EML 416 may provide the light having a wavelength range of about 440 to 480 nm, and the second EML 434 may provide the light having a wavelength range of about 500 to 550 nm.

Alternatively, the second EML 434 may have a double-layered structure of a first layer emitting red light and a second layer emitting green light. In this instance, the first layer emitting the red light may include a host and a red dopant, and the second layer emitting the green light may include a host and a green dopant.

In the first EML 416 having the wavelength range of 440 to 480 nm, a host may be an anthracene derivative, and a dopant may be a pyrene derivative. For example, in the first EML 416, the host may be 9,10-di(naphtha-2-yl)anthracene, and the dopant may be 1,6-bis(diphenylamino)pyrene. In the second EML 434 having the wavelength range of 500 to 550 nm, a host may be carbazole derivative, and the dopant may be iridium derivative (complex). For example, in the second EML 434, the host may be 4,4'-bis(N-Carbazolyl)-1,1'-biphenyl (CBP), and the dopant may be tris(2-phenylpyridine) Iridium(III) ($Ir(ppy)_3$).

The CGL 450 includes an n-type CGL 452 and a p-type CGL 454. The n-type CGL 452 is positioned between the first ETL 418 and the second HTL 432, and the p-type CGL 454 is positioned between the n-type CGL 452 and the second HTL 432.

The n-type CGL 452 provides the electron toward the first ETL 418, and the electron is transferred into the first EML 416 through the first ETL 418. The p-type CGL 454 provides the hole toward the second HTL 432, and the hole is transferred into the second EML 434 through the second HTL 432. As a result, in the OLED D having a two-stack (double-stack) structure, the driving voltage is reduced, and the emitting efficiency is improved.

The n-type CGL 452 includes an n-type charge generation material and may have a thickness of 100 to 200 Å. For example, the n-type charge generation material may be selected from the group consisting of tris-(8-hydroxyquinoline aluminum (Alq3), 2-biphenyl-4-yl-5-(4-t-butylphenyl)-1,3,4-oxadiazole (PBD), spiro-PBD, lithium quinolate (Liq), 1,3,5-tris(N-phenylbenzimidazol-2-yl)benzene (TPBi), bis(2-methyl-8-quinolinolato-N1,O8)-(1,1'-biphenyl-4-olato) aluminum (BAlq), 4,7-diphenyl-1,10-phenanthroline (Bphen), 2,9-bis(naphthalene-2-yl)4,7-diphenyl-1,10-phenanthroline (NBphen), 2,9-dimethyl-4,7-diphenyl-1,10-phenathroline (BCP), 3-(4-biphenyl)-4-phenyl-5-tert-butylphenyl-1,2,4-triazole (TAZ), 4-(naphthalen-1-yl)-3,5-diphenyl-4H-1,2,4-triazole (NTAZ), 1,3,5-tri(p-pyrid-3-yl-phenyl)benzene (TpPyPB), 2,4,6-tris(3'-(pyridin-3-yl)biphenyl-3-yl)1,3,5-triazine (TmPPPyTz), poly[9,9-bis(3'-((N,N-dimethyl)-N-ethylammonium)-propyl)-2,7-fluorene]-alt-2,7-(9,9-dioctylfluorene)] (PFNBr), tris(phenylquinoxaline (TPQ), and diphenyl-4-triphenylsilyl-phenylphosphine oxide (TSPO1). In one embodiment of the present disclosure, the n-type charge generation material may be phenanthroline derivative, e.g., bathophenanthroline (Bphene).

In addition, the n-type CGL 452 may further include an auxiliary n-type charge generation material. For example, the auxiliary n-type charge generation material may be alkali metal, e.g., Li, Cs, K, Rb, Na or Fr, or alkali earth metal, e.g., Be, Mg, Ca, Sr, Ba or Ra. In the n-type CGL 452, the auxiliary n-type charge generation material may have a weight % of about 0.1 to 20 wt %, preferably about 1 to 10 wt %.

At least one of the HIL 420 and the p-type CGL 454 include the organic compound of the present disclosure in Formula 1-1. For example, the HIL 420 may include the organic compound of the present disclosure as a hole injection material 422, and the p-type CGL 454 may include the organic compound of the present disclosure as a p-type charge generation material 456.

The hole injection material 422 in the HIL 420 and the p-type charge generation material 456 in the p-type CGL 454 may be same or different.

The HIL 420 may have a thickness of about 50 to 200 Å. When the HIL 420 includes the organic compound of the present disclosure as the hole injection material 422, the HIL 420 may further include a hole injection host material (not shown). Namely, the HIL 420 may include only the organic compound of the present disclosure as the hole injection material 422 or may include a mixture of the hole injection material 422 and the hole injection host material.

For example, the hole injection host material may be NPD. In this instance, in the HIL 420, the hole injection material 422 being the organic compound of the present disclosure may have a weight % of about 1 to 40 wt %, preferably about 5 to 20 wt %.

The p-type CGL 454 may have a thickness of about 100 to 200 Å. When the p-type CGL 454 includes the organic compound of the present disclosure as the p-type charge generation material 456, the p-type CGL 454 may further include a p-type charge generation host material (not shown). Namely, the p-type CGL 454 may include only the organic compound of the present disclosure as the p-type charge generation material 456 or may include a mixture of the p-type charge generation material 456 and the p-type charge generation host material.

For example, the p-type charge generation host material may be selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPD), 1,4,5,8,9,11-hexaazatriphenylenehexacarbonitrile (dipyrazino[2,3-f:2'3'-h]quinoxaline-2,3,6,7,10,11-hexacarbonitrile (HAT-CN), 1,3,5-tris[4-(diphenylamino)phenyl]benzene (TDAPB), poly(3,4-ethylenedioxythiphene) polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine, but it is not limited thereto. For example, the p-type charge generation host material may be NPD. In this instance, in the p-type CGL 454, the p-type charge generation material 456 being the organic compound of the present disclosure may have a weight % of about 1 to 40 wt %, preferably about 10 to 30 wt %.

For example, when the HIL 420 includes the hole injection host material and the hole injection material 422 being the organic compound of the present disclosure and the p-type CGL 454 includes the p-type charge generation host material and the p-type charge generation material 456 being the organic compound of the present disclosure, the weight % of the p-type charge generation material 456 in the p-type CGL 454 may be equal to or greater than that of the hole injection material 422 in the HIL 420.

The OLED D including the first emitting part 410 having the wavelength range of 440 to 480 nm and the second emitting part 430 having the wavelength range of 500 to 550 nm provides the white emission, and the CGL 450 including the organic compound of the present disclosure is provided between the first and second emitting parts 410 and 430. As a result, the OLED D has advantages in the driving voltage, the emitting efficiency and the lifespan.

Referring to FIG. 6, the organic emitting layer 362 includes a first emitting part 510 including a first EML 516 and an HIL 520, a second emitting part 530 including a second EML 534, a third emitting part 550 including a third EML 554, a first CGL 570 between the first and second emitting parts 510 and 530 and a second CGL 580 between the second and third emitting parts 530 and 550.

The first CGL 570 is positioned between the first and second emitting parts 510 and 530, and the second CGL 580 is positioned between the second and third emitting parts 530 and 550. Namely, the first emitting part 510, the first CGL 570, the second emitting part 530, the second CGL 580 and the third emitting part 550 are sequentially stacked on the first electrode 360. In other words, the first emitting part 510 is positioned between the first electrode 360 and the first CGL 570, the second emitting part 530 is positioned between the first and second CGLs 570 and 580, and the third emitting part 550 is positioned between the second electrode 360 and the second CGL 580.

In the first emitting part 510, the HIL 520 is positioned under the first EML 516. Namely, the HIL 520 is positioned between the first electrode 360 and the first EML 516.

The first emitting part 510 may further include at least one of a first HTL 514 positioned between the HIL 520 and the first EML 516 and a first ETL 518 over the first EML 516.

Although not shown, the first emitting part 510 may further include at least one of an EBL between the first HTL 514 and the first EML 516 and an HBL between the first EML 516 and the first ETL 518.

The second emitting part 530 may further include at least one of a second HTL 532 under the second EML 534 and a second ETL 540 over the second EML 534.

Although not shown, the second emitting part 530 may further include at least one of an EBL between the second HTL 532 and the second EML 534 and an HBL between the second EML 534 and the second ETL 540.

The third emitting part 550 may further include an EIL 556. In addition, the third emitting part 550 may further include at least one of a third HTL 552 under the third EML 554 and a third ETL 560 between the third EML 554 and the EIL 556.

Although not shown, the third emitting part 550 may further include at least one of an EBL between the third HTL 552 and the third EML 554 and an HBL between the third EML 554 and the third ETL 560.

Each of the first and third EMLs 516 and 554 provides a light having a wavelength range of about 440 to 480 nm, and the second EML 534 provides a light having a wavelength range of about 500 to 550 nm.

Alternatively, the second EML 534 may have a double-layered structure of a first layer emitting red light and a second layer emitting green light. In addition, the second EML 534 may have a triple-layered structure of a first layer including a host and a red dopant, a second layer including a host and a yellow-green dopant and a third layer including a host and a green dopant.

In each of the first and third EMLs 516 and 554 having the wavelength range of 440 to 480 nm, a host may be an anthracene derivative, and a dopant may be a pyrene derivative. For example, in each of the first and third EMLs 516 and 554, the host may be 9,10-di(naphtha-2-yl)anthracene, and the dopant may be 1,6-bis(diphenylamino)pyrene.

In the second EML 534 having the wavelength range of 500 to 550 nm, a host may be carbazole derivative, and the dopant may be iridium derivative (complex). For example, in the second EML 534, the host may be 4,4'-bis(N-Carbazolyl)-1,1'-biphenyl (CBP), and the dopant may be tris(2-phenylpyridine) Iridium(III) ($Ir(ppy)_3$).

The first CGL 570 includes a first n-type CGL 572 and a first p-type CGL 574. The first n-type CGL 572 is positioned between the first ETL 518 and the second HTL 532, and the first p-type CGL 574 is positioned between the first n-type CGL 572 and the second HTL 532.

The second CGL 580 includes a second n-type CGL 582 and a second p-type CGL 584. The second n-type CGL 582 is positioned between the second ETL 540 and the third HTL 552, and the second p-type CGL 584 is positioned between the second n-type CGL 582 and the third HTL 552.

The first n-type CGL 572 provides the electron toward the first ETL 518, and the electron is transferred into the first EML 516 through the first ETL 518. The first p-type CGL 574 provides the hole toward the second HTL 532, and the hole is transferred into the second EML 534 through the second HTL 532.

The second n-type CGL 582 provides the electron toward the second ETL 540, and the electron is transferred into the second EML 534 through the second ETL 540. The second p-type CGL 584 provides the hole toward the third HTL 552, and the hole is transferred into the third EML 554 through the third HTL 552.

As a result, in the OLED D having a three-stack (triple-stack) structure, the driving voltage is reduced, and the emitting efficiency is improved.

Each of the first and second n-type CGLs 572 and 582 includes an n-type charge generation material and may have a thickness of 100 to 200 Å. For example, the n-type charge generation material may be Bphene. In addition, each of the first and second n-type CGLs 572 and 582 may further include an auxiliary n-type charge generation material. For example, the auxiliary n-type charge generation material may be alkali metal or alkali earth metal.

At least one of the HIL 520, the first p-type CGL 574 and the second p-type CGL 584 include the organic compound of the present disclosure in Formula 1-1. For example, the HIL 520 may include the organic compound of the present disclosure as a hole injection material 522. The first p-type CGL 574 may include the organic compound of the present disclosure as a first p-type charge generation material 576, and the second p-type CGL 584 may include the organic compound of the present disclosure as a second p-type charge generation material 586.

The hole injection material 522 in the HIL 520, the first p-type charge generation material 576 in the first p-type CGL 574 and the second p-type charge generation material 586 in the second p-type CGL 584 may be same or different.

The HIL 520 may have a thickness of about 50 to 200 Å. When the HIL 520 includes the organic compound of the present disclosure as the hole injection material 522, the HIL 520 may further include a hole injection host material (not shown). Namely, the HIL 520 may include only the organic compound of the present disclosure as the hole injection material 522 or may include a mixture of the hole injection material 522 and the hole injection host material.

For example, the hole injection host material may be NPD. In this instance, in the HIL 520, the hole injection material 522 being the organic compound of the present disclosure may have a weight % of about 1 to 40 wt %, preferably about 5 to 20 wt %.

Each of the first and second p-type CGLs 574 and 584 may have a thickness of about 100 to 200 Å. When each of the first and second p-type CGLs 574 and 584 includes the organic compound of the present disclosure as the first and second p-type charge generation materials 576 and 586, respectively, each of the first and second p-type CGLs 574 and 584 may further include a p-type charge generation host material (not shown). Namely, each of the first and second p-type CGLs 574 and 584 may include only the organic compound of the present disclosure as the first and second p-type charge generation materials 576 and 586, respectively, or may include a mixture of respective one of the first and second p-type charge generation materials 576 and 586 and the p-type charge generation host material.

For example, the p-type charge generation host material may be NPD. In this instance, in each of the first and second p-type CGLs 574 and 584, each of the first and second p-type charge generation materials 576 and 586 being the organic compound of the present disclosure may have a weight % of about 1 to 40 wt %, preferably about 10 to 30 wt %.

For example, when the HIL 520 includes the hole injection host material and the hole injection material 522 being the organic compound of the present disclosure and the first and second p-type CGLs 574 and 584 respectively include the p-type charge generation host material and respective one of the first and second p-type charge generation materials 576 and 586 being the organic compound of the present disclosure, the weight % of each of the first and second p-type charge generation materials 576 and 586 in the first and second p-type CGLs 574 and 584 may be equal to or greater than that of the hole injection material 522 in the HIL 520.

The OLED D including the first and third emitting parts 510 and 550 each having the wavelength range of 440 to 480 nm and the second emitting part 530 having the wavelength range of 500 to 550 nm provides the white emission, and the first and second CGLs 570 and 580 including the organic compound of the present disclosure is provided between the first and second emitting parts 510 and 530 and between the second and third emitting parts 530 and 550, respectively. As a result, the OLED D has advantages in the driving voltage, the emitting efficiency and the lifespan.

Referring to FIG. 4 again, a second electrode 364 is formed over the substrate 310 where the organic emitting layer 362 is formed.

In the organic light emitting display device 300, since the light emitted from the organic emitting layer 362 is incident to the color filter layer 380 through the second electrode 364, the second electrode 364 has a thin profile for transmitting the light.

The first electrode 360, the organic emitting layer 362 and the second electrode 364 constitute the OLED D.

The color filter layer 380 is positioned over the OLED D and includes a red color filter 382, a green color filter 384 and a blue color filter 386 respectively corresponding to the red, green and blue pixels RP, GP and BP. The red color filter 382 may include at least one of red dye and red pigment, the green color filter 384 may include at least one of green dye and green pigment, and the blue color filter 386 may include at least one of blue dye and blue pigment.

Although not shown, the color filter layer 380 may be attached to the OLED D by using an adhesive layer. Alternatively, the color filter layer 380 may be formed directly on the OLED D.

An encapsulation film (not shown) may be formed to prevent penetration of moisture into the OLED D. For example, the encapsulation film may include a first inorganic insulating layer, an organic insulating layer and a second inorganic insulating layer sequentially stacked, but it is not limited thereto. The encapsulation film may be omitted.

A polarization plate (not shown) for reducing an ambient light reflection may be disposed over the top-emission type OLED D. For example, the polarization plate may be a circular polarization plate.

In the OLED of FIG. 4, the first and second electrodes 360 and 364 are a reflection electrode and a transparent (or semi-transparent) electrode, respectively, and the color filter layer 380 is disposed over the OLED D. Alternatively, when the first and second electrodes 360 and 364 are a transparent (or semi-transparent) electrode and a reflection electrode, respectively, the color filter layer 380 may be disposed between the OLED D and the first substrate 310.

A color conversion layer (not shown) may be formed between the OLED D and the color filter layer 380. The color conversion layer may include a red color conversion layer, a green color conversion layer and a blue color conversion layer respectively corresponding to the red, green and blue pixels RP, GP and BP. The white light from the OLED D is converted into the red light, the green light and the blue light by the red, green and blue color conversion layer, respectively. For example, the color conversion layer may include a quantum dot. Accordingly, the color purity of the organic light emitting display device 300 may be further improved.

The color conversion layer may be included instead of the color filter layer 380.

As described above, in the organic light emitting display device 300, the OLED D in the red, green and blue pixels RP, GP and BP emits the white light, and the white light from the organic light emitting diode D passes through the red color filter 382, the green color filter 384 and the blue color filter 386. As a result, the red light, the green light and the blue light are provided from the red pixel RP, the green pixel GP and the blue pixel BP, respectively.

In FIG. 4, the OLED D emitting the white light is used for a display device. Alternatively, the OLED D may be formed on an entire surface of a substrate without at least one of the driving element and the color filter layer to be used for a lightening device. The display device and the lightening device each including the OLED D of the present disclosure may be referred to as an organic light emitting device.

In the OLED D and the organic light emitting display device 300, at least one of the HIL and the p-type CGL includes the organic compound of the present disclosure such that the hole is efficiently provided into the EML. Accordingly, in the OLED and the display device 300, the driving voltage is decreased, and the emitting efficiency and the lifespan are increased.

[OLED1]

On the anode (ITO), the HIL (100 Å), the HTL (1000 Å, NPD), the EML (200 Å, the host (9,10-di(naphtha-2-yl) anthracene) and the dopant (1,6-bis(diphenylamino)pyrene, 3 wt %), the ETL (200 Å, 1,3,5-tri(m-pyridin-3-ylphenyl) benzene(TmPyPB)), the EIL (LiF, 10 Å) and the cathode (Al, 1500 Å) was sequentially deposited to form the OLED.

1. COMPARATIVE EXAMPLES (1) Comparative Example 1 (Ref1)

NPD and HATCN (10 wt %) are used to form the HIL.

(2) Comparative Example 2 (Ref2)

NPD and the compound OA1 in Formula 3 (10 wt %) are used to form the HIL.

(3) Comparative Example 3 (Ref3)

NPD and the compound OA2 in Formula 3 (10 wt %) are used to form the HIL.

(4) Comparative Example 4 (Ref4)

NPD and the compound OA3 in Formula 3 (10 wt %) are used to form the HIL.

(5) Comparative Example 5 (Ref5)

NPD and the compound OA4 in Formula 3 (10 wt %) are used to form the HIL.

(6) Comparative Example 6 (Ref6)

NPD and the compound OA5 in Formula 3 (10 wt %) are used to form the HIL.

(7) Comparative Example 7 (Ref7)

NPD and the compound OA6 in Formula 3 (10 wt %) are used to form the HIL.

2. EXAMPLES (1) Example 1 (Ex1)

NPD and the compound 4 in Formula 2 (10 wt %) are used to form the HIL.

(2) Example 2 (Ex2)

NPD and the compound 13 in Formula 2 (10 wt %) are used to form the HIL.

(3) Example 3 (Ex3)

NPD and the compound 37 in Formula 2 (10 wt %) are used to form the HIL.

[Formula 3]

OA1

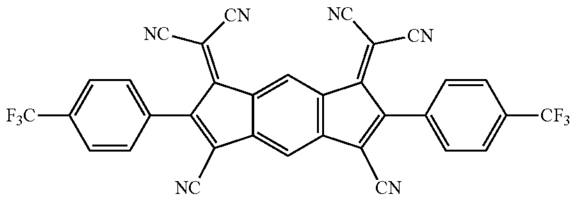

OA2

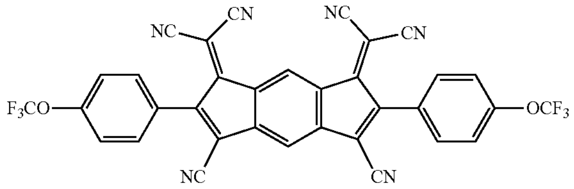

OA3

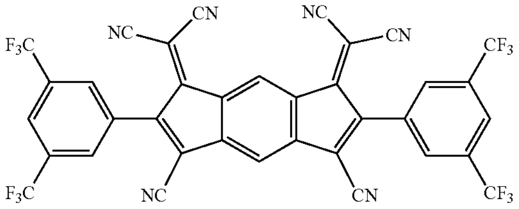

OA4

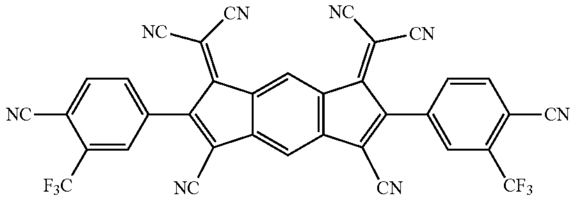

-continued

OA5

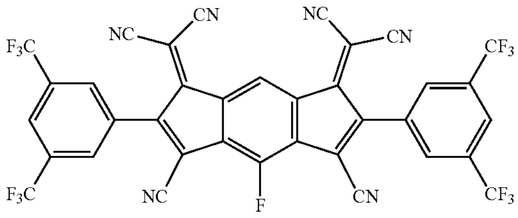

OA6

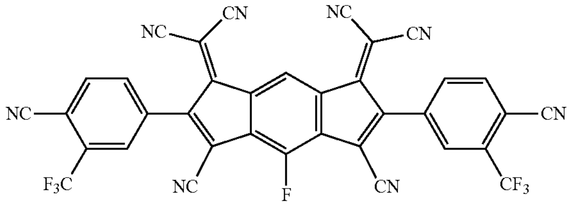

The properties, i.e., voltage (V), efficiency (Cd/A), and lifespan (hr), of the OLEDs manufactured in Comparative Examples 1 to 7 and Examples 1 to 3 are measured and listed in Table 1.

TABLE 1

| | HIL | | V | Cd/A | lifespan [hr] |
|---|---|---|---|---|---|
| Ref1 | NPD | HATCN | 6.23 | 2.28 | 25 |
| Ref2 | NPD | OA1 | 4.56 | 4.04 | 36 |
| Ref3 | NPD | OA2 | 4.63 | 3.89 | 35 |
| Ex1 | NPD | 4 | 4.34 | 4.22 | 40 |
| Ref4 | NPD | OA3 | 4.45 | 4.15 | 46 |
| Ref5 | NPD | OA4 | 4.13 | 4.40 | 48 |
| Ex2 | NPD | 13 | 3.96 | 4.57 | 62 |
| Ref6 | NPD | OA5 | 4.01 | 4.58 | 54 |
| Ref7 | NPD | OA6 | 3.92 | 4.62 | 58 |
| Ex3 | NPD | 37 | 3.77 | 4.85 | 73 |

As shown in Table 1, in the OLED of Ref1, a difference between the dipole moment of NPD and the dipole moment of HAYCN is very small or zero, the hole injection property is degraded. In addition, the compounds OA1 to OA6 in Formula 3 used in the OLED of Ref2 to Ref7 have a symmetric structure and have a relatively low dipole moment. As a result, the hole injection property of the OLED of Ref2 to Ref7 is degraded. On the other hand, the organic compound of the present disclosure is an indacene compound having an asymmetric structure and has a relatively high dipole moment. Accordingly, in comparison to the OLED of Ref1 to Ref7, the driving voltage of the OLED of Ex1 to Ex3 is decreased, and the emitting efficiency and the lifespan of the OLED of Ex1 to Ex3 are improved.

[OLED2]

On the anode (ITO), the HIL (100 Å, NPD+HATCN (10 wt %)), the first HTL (1000 Å, NPD), the first EML (200 Å, the host (9,10-di(naphtha-2-yl)anthracene) and the dopant (1,6-bis(diphenylamino)pyrene, 3 wt %), 200 Å), the first ETL (180 Å, TmPyPB), the n-type CGL (150 Å, Bphen+Li (2 wt %)), the p-type CGL (150 Å), the second HTL (300 Å, NPD), the second EML (250 Å, the host (CBP) and the dopant ($Ir(ppy)_3$, 8 wt %)), the second ETL (200 Å, 2,2',2"-(1,3,5-benzinetriyl)-tris(1-phenyl-1-H benzimidazole) (TPBi)), the EIL (LiF, 10 Å) and the cathode (Al, 1500 Å) was sequentially deposited to form the OLED.

3. COMPARATIVE EXAMPLES (1) Comparative Example 8 (Ref8)

NPD and HATCN (20 wt %) are used to form the p-CGL.

(2) Comparative Example 9 (Ref9)

NPD and the compound OA1 in Formula 3 (20 wt %) are used to form the p-CGL.

(3) Comparative Example 10 (Ref10)

NPD and the compound OA2 in Formula 3 (20 wt %) are used to form the p-CGL.

(4) Comparative Example 11 (Ref11)

NPD and the compound OA3 in Formula 3 (20 wt %) are used to form the p-CGL.

(5) Comparative Example 12 (Ref12)

NPD and the compound OA4 in Formula 3 (20 wt %) are used to form the p-CGL.

(6) Comparative Example 13 (Ref13)

NPD and the compound OA5 in Formula 3 (20 wt %) are used to form the p-CGL.

(7) Comparative Example 14 (Ref14)

NPD and the compound OA6 in Formula 3 (20 wt %) are used to form the p-CGL.

4. EXAMPLES (1) Example 4 (Ex4)

NPD and the compound 4 in Formula 2 (20 wt %) are used to form the p-CGL.

(2) Example 5 (Ex5)

NPD and the compound 13 in Formula 2 (20 wt %) are used to form the p-CGL.

(3) Example 6 (Ex6)

NPD and the compound 37 in Formula 2 (20 wt %) are used to form the p-CGL.

The properties, i.e., voltage (V), efficiency (Cd/A), and lifespan (hr), of the OLEDs manufactured in Comparative Examples 8 to 14 and Examples 4 to 6 are measured and listed in Table 2.

TABLE 2

| | P-CGL | | V | Cd/A | lifespan [hr] |
|---|---|---|---|---|---|
| Ref8 | NPD | HATCN | 12.19 | 39.64 | 63 |
| Ref9 | NPD | OA1 | 9.18 | 4824 | 148 |
| Ref10 | NPD | OA2 | 9.22 | 47.18 | 136 |
| Ex4 | NPD | 4 | 9.00 | 49.65 | 159 |
| Ref11 | NPD | OA3 | 9.05 | 49.96 | 157 |
| Ref12 | NPD | OA4 | 8.76 | 51.66 | 166 |
| Ex5 | NPD | 13 | 8.54 | 52.28 | 187 |
| Ref13 | NPD | OA5 | 8.58 | 52.91 | 168 |

TABLE 2-continued

| | P-CGL | | V | Cd/A | lifespan [hr] |
|---|---|---|---|---|---|
| Ref14 | NPD | OA6 | 8.46 | 53.26 | 174 |
| Ex6 | NPD | 37 | 8.39 | 55.34 | 193 |

As shown in Table 2, in the OLED of Ref8, a difference between the dipole moment of NPD and the dipole moment of HAYCN is very small or zero, the hole injection property is degraded. In addition, the compounds OA1 to OA6 in Formula 3 used in the OLED of Ref9 to Ref14 have a symmetric structure and have a relatively low dipole moment. As a result, the hole injection property of the OLED of Ref9 to Ref14 is degraded. On the other hand, the organic compound of the present disclosure is an indacene compound having an asymmetric structure and has a relatively high dipole moment. Accordingly, in comparison to the OLED of Ref8 to Ref14, the driving voltage of the OLED of Ex4 to Ex6 is decreased, and the emitting efficiency and the lifespan of the OLED of Ex1 to Ex3 are improved.

It will be apparent to those skilled in the art that various modifications and variations can be made in the embodiments of the present disclosure without departing from the spirit or scope of the present disclosure. Thus, it is intended that the modifications and variations are covered by this disclosure provided they come within the scope of the appended claims and their equivalents.

What is claimed is:

1. An organic light emitting diode, comprising:

a first electrode;

a second electrode facing the first electrode;

a first emitting material layer positioned between the first and second electrodes; and a hole injection layer positioned between the first electrode and the first emitting material layer and including a hole injection material;

a second emitting material layer between the first emitting material layer and the second electrode; and a first p-type charge generation layer including a first p-type charge generation material and positioned between the first and second emitting material layers, wherein each of the hole injection material and the first p-type charge generation material is an organic compound in Formula 1-4:

[Formula 1-4]

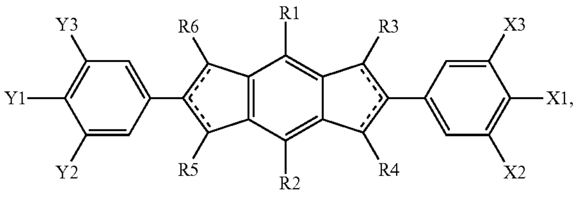

wherein each of R1 and R2 is independently selected from the group consisting of hydrogen, deuterium, halogen and cyano, wherein each of R3 to R6 is independently selected from the group consisting of halogen, cyano, malononitrile, C1 to C10 haloalkyl group and C1 to C10 haloalkoxy group, and at least one of R3 and R4 and at least one of R5 and R6 are malononitrile, wherein each of X1 to X3 and each of Y1 to Y3 are independently selected from the group consisting of H, C1 to C10 alkyl group, halogen, cyano, malononitrile, C1 to C10 haloalkyl group, and C1 to C10 haloalkoxy group, and satisfy at least one selected from i) X1 and Y1 are different and ii) X2 is different from Y2 and Y3, or X3 is different from Y2 and Y3, and wherein a weight % of the first p-type charge generation material in the first p-type charge generation layer is greater than a weight % of the hole injection material in the hole injection layer.

2. The organic light emitting diode according to claim 1, wherein the hole injection layer further includes a hole injection host material, and wherein the hole injection host material is selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), N,N'-diphenyl-N,N'-bis(1-naphthyl)-1,1'-biphenyl-4,4"-diamine (NPD), 1,4,5,8,9,11-hexaazatriphenylenehexacarbonitrile (dipyrazino[2,3-f:2'3'-h]quinoxaline-2,3,6,7,10,11-hexacarbonitrile (HAT-CN), 1,3,5-tris[4-(diphenylamino)phenyl]benzene (TDAPB), poly(3,4-ethylenedioxythiophene)polystyrene sulfonate (PEDOT/PSS), and N-(biphenyl-4-yl)-9,9-dimethyl-N-(4-(9-phenyl-9H-carbazol-3-yl)phenyl)-9H-fluoren-2-amine.

3. The organic light emitting diode according to claim 1, wherein the hole injection layer further includes a hole injection host material, and the first p-type charge generation layer further includes a p-type charge generation host material.

4. The organic light emitting diode according to claim 1, wherein the first emitting material layer has an emission wavelength range of 440 to 480 nm, and the second emitting material layer has an emission wavelength range of 500 to 550 nm.

5. The organic light emitting diode according to claim 1, further comprising:

a third emitting material layer between the second emitting material layer and the second electrode; and a second p-type charge generation layer including a second p-type charge generation material and positioned between the second and third emitting material layers.

6. The organic light emitting diode according to claim 5, wherein the second p-type charge generation material is the organic compound in Formula 1-4.

7. The organic light emitting diode according to claim 6, wherein the hole injection layer further includes a hole injection host material, and the first and second p-type charge generation layers further includes first and second p-type charge generation host materials, respectively, and wherein a weight % of the second charge generation material in the second p-type charge generation layer is greater than a weight % of the hole injection material in the hole injection layer.

8. An organic light emitting device, comprising:

a substrate; and an organic light emitting diode positioned on the substrate and including a first electrode; a second electrode facing the first electrode; a first emitting material layer positioned between the first and second electrodes; a hole injection layer positioned between the first electrode and the first emitting material layer and including a hole injection material; a second emitting material layer between the first emitting material layer and the second electrode; and a first p-type charge generation layer including a first p-type charge generation material and positioned between the first and second emitting material layers; and an encapsulation film covering the organic light emitting diode, wherein each of the hole injection material and the first p-type charge generation material is an organic compound in Formula 1-4:

[Formula 1-4]

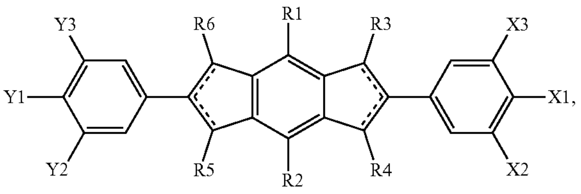

wherein each of R1 and R2 is independently selected from the group consisting of hydrogen, deuterium, halogen and cyano, wherein each of R3 to R6 is independently selected from the group consisting of halogen, cyano, malononitrile, C1 to C10 haloalkyl group and C1 to C10 haloalkoxy group, and at least one of R3 and R4 and at least one of R5 and R6 are malononitrile, wherein each of X1 to X3 and each of Y1 to Y3 are independently selected from the group consisting of H, C1 to C10 alkyl group, halogen, cyano, malononitrile, C1 to C10 haloalkyl group, and C1 to C10 haloalkoxy group, and satisfy at least one selected from i) X1 and Y1 are different and ii) X2 is different from Y2 and Y3, or X3 is different from Y2 and Y3, and wherein a weight % of the first p-type charge generation material in the first p-type charge generation layer is greater than a weight % of the hole injection material in the hole injection layer.

9. The organic light emitting diode according to claim 1, wherein the hole injection layer further includes a hole injection host material, and wherein the hole injection host material includes a compound selected from the group consisting of 4,4',4"-tris(3-methylphenylamino)triphenylamine (MTDATA), 4,4',4"-tris(N,N-diphenyl-amino)triphenylamine (NATA), 4,4',4"-tris(N-(naphthalene-1-yl)-N-phenyl-amino)triphenylamine (1T-NATA), 4,4',4"-tris(N-(naphthalene-2-yl)-N-phenyl-amino)triphenylamine (2T-NATA), copper phthalocyanine (CuPc), tris(4-carbazoyl-9-yl-phenyl)amine (TCTA), 1,4,5,8,9,11-hexaazatriphenylenehexacarbonitrile (dipyrazino[2,3-f:2'3'-h]quinoxaline-2,3,6,7,10,11-hexacarbonitrile (HAT-CN), 1,3,5-tris[4-(diphenylamino)phenyl]benzene (TDAPB), and poly(3,4-ethylenedioxythiophene)polystyrene sulfonate (PEDOT/PSS).

10. The organic light emitting diode according to claim 1, wherein the organic compound includes compounds in Formula 2, and each of the hole injection material and the first p-type charge generation material includes a compound in Formula 2:

[Formula 2]
1
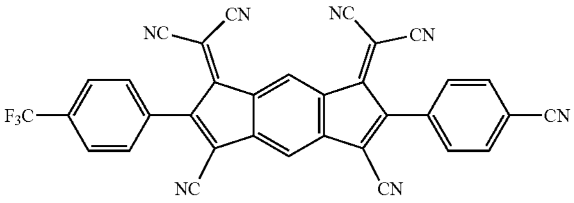
2
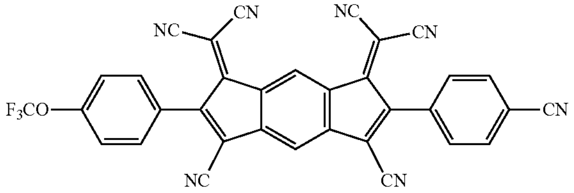
3
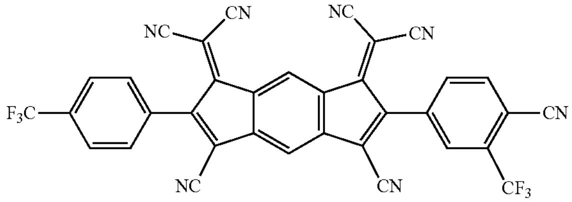
4
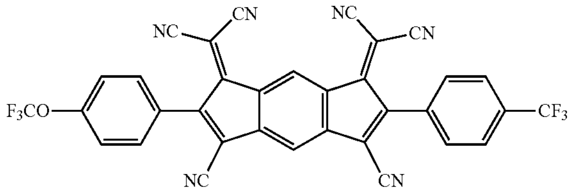
5
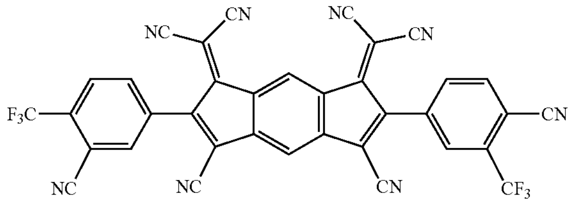
6
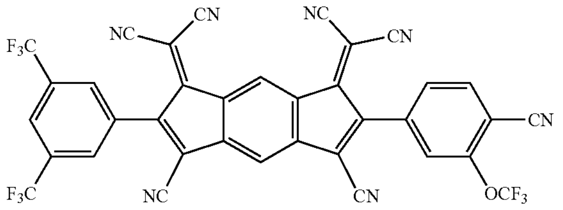
7
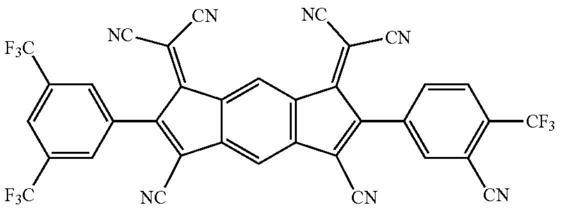
-continued
8
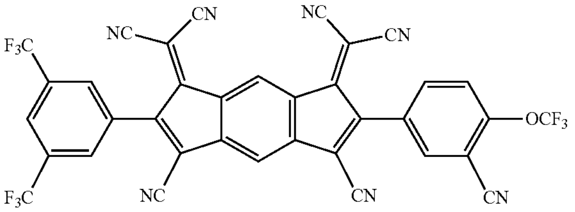
9
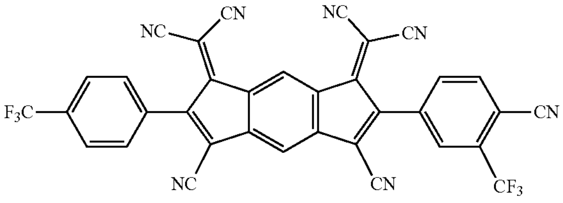
10
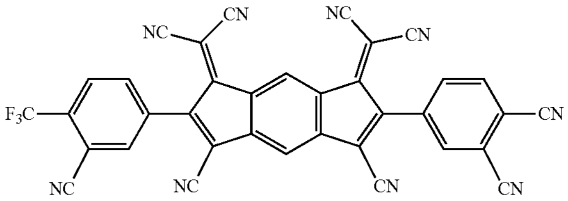
11
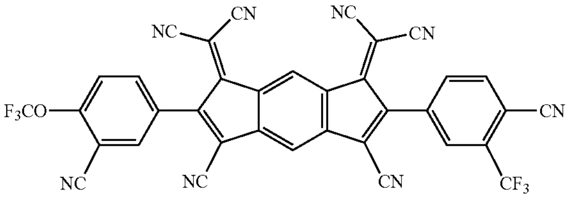
12
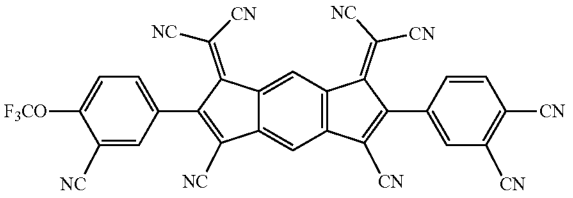
13
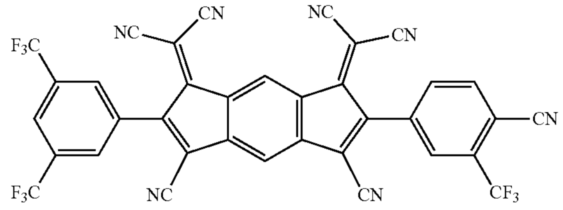
14
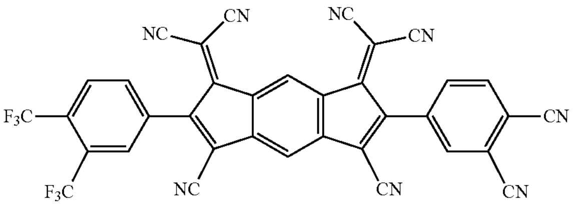

-continued
15
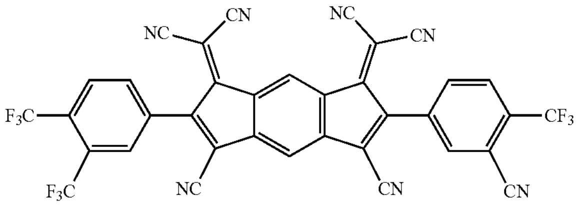
16
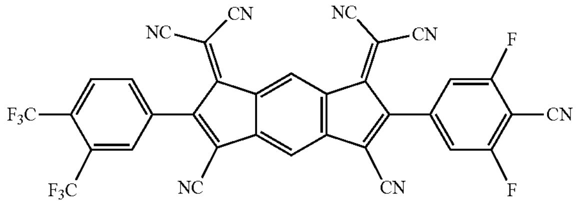
17
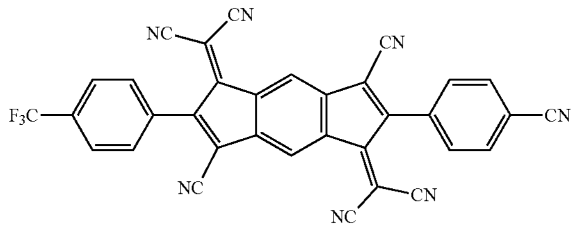
18
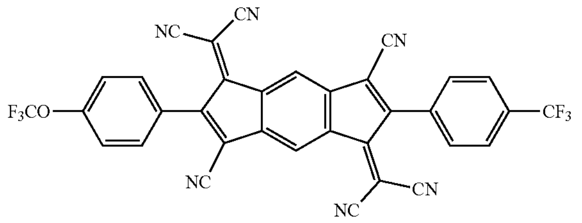
19
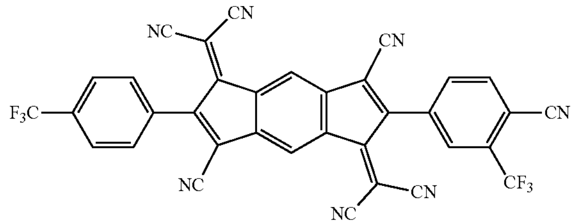
20
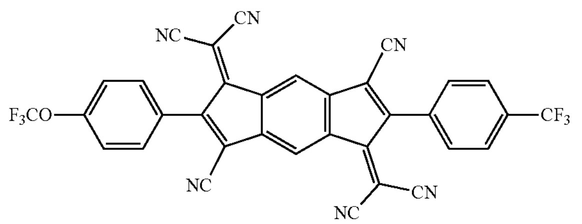
-continued
21
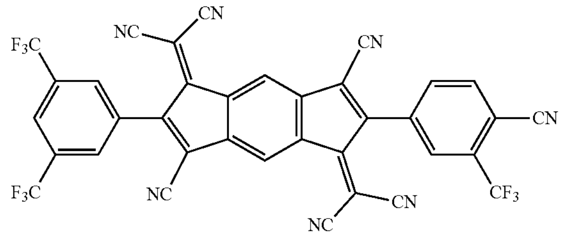
22
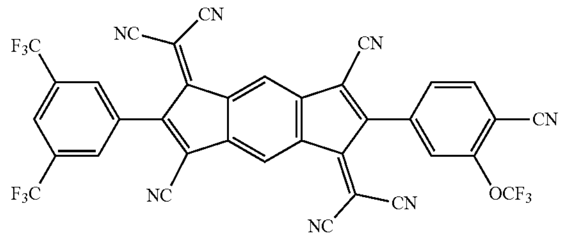
23
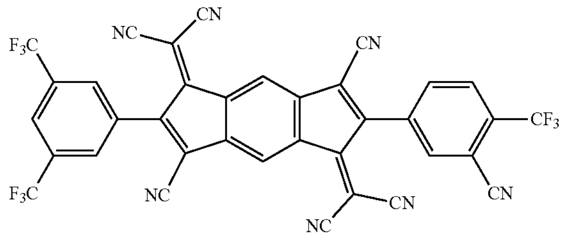
24
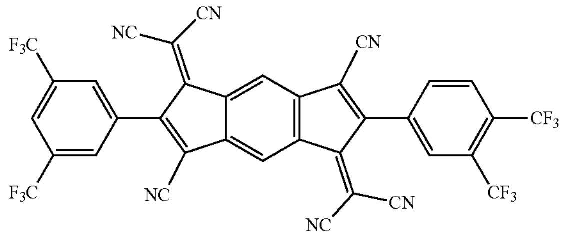
25
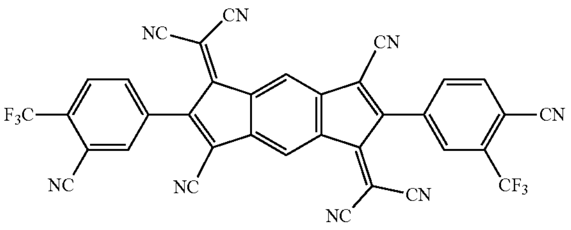
26
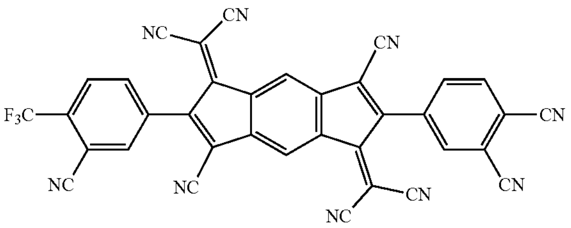

-continued
27
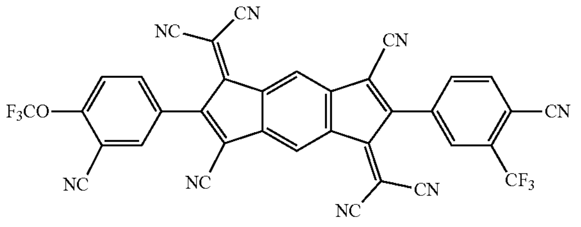
31
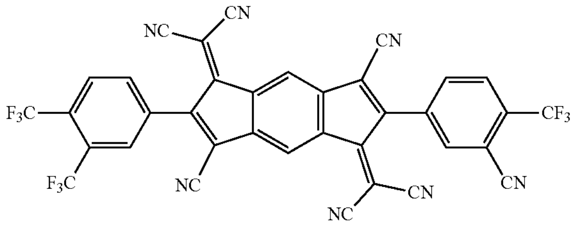
32
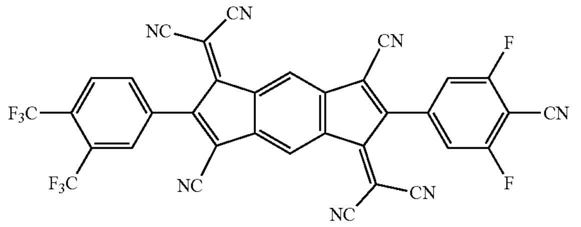
33
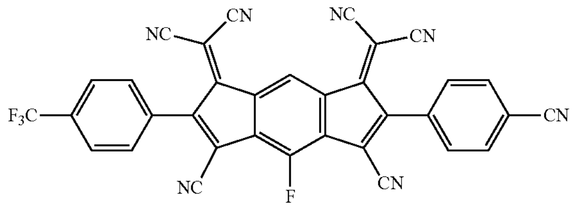
34
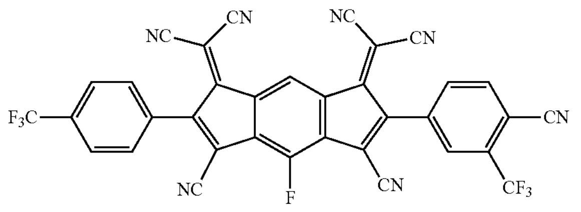
35
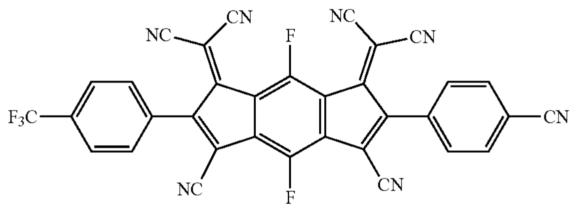
-continued
36
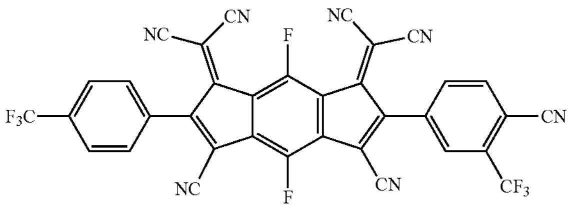
37
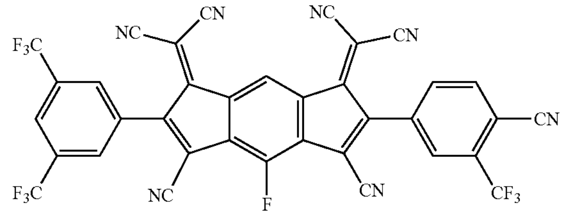
38
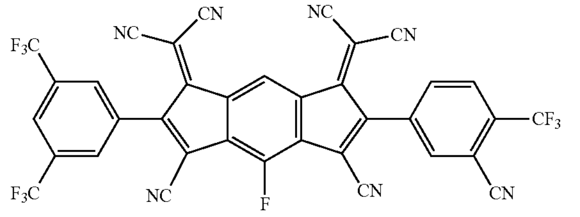
39
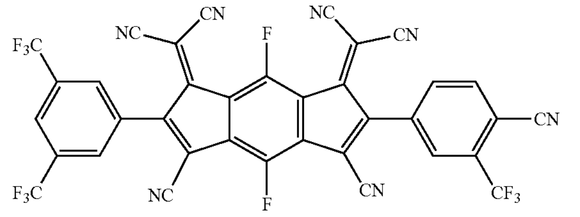
40
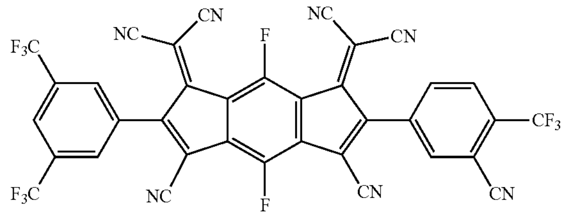
41
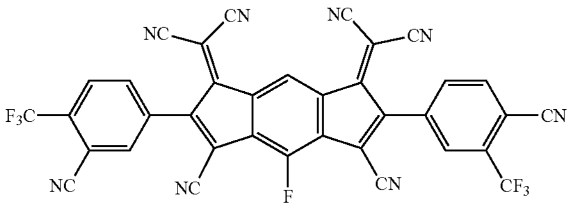

-continued
42
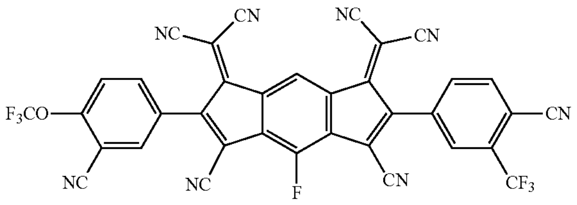
43
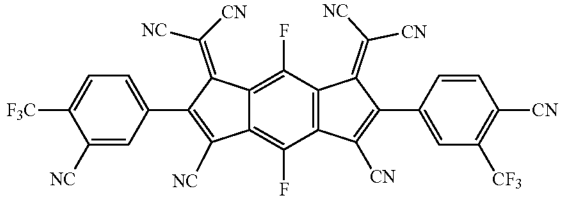
44
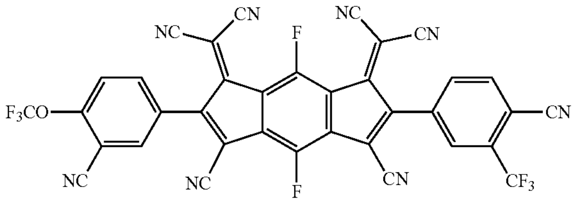
45
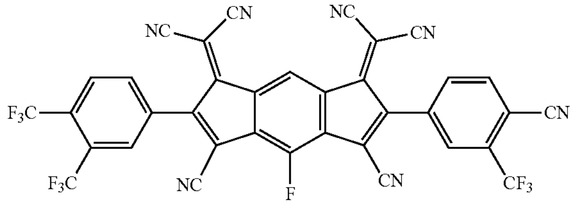
46
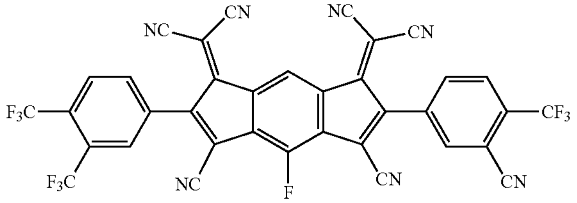
47
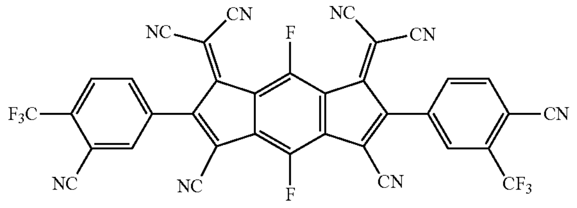
48
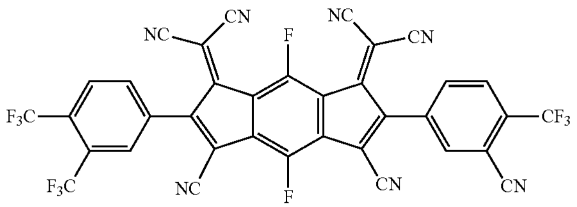
-continued
49
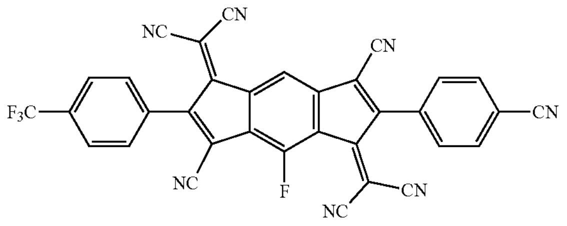
50
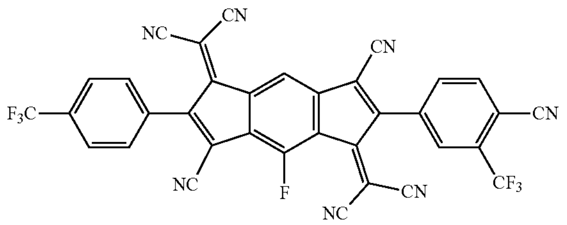
51
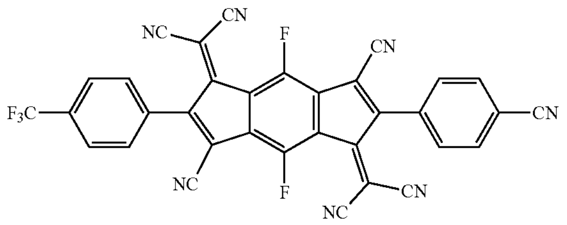
52
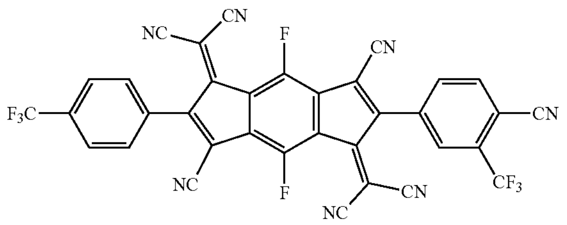
53
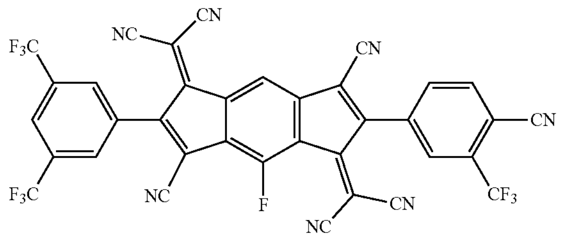
54
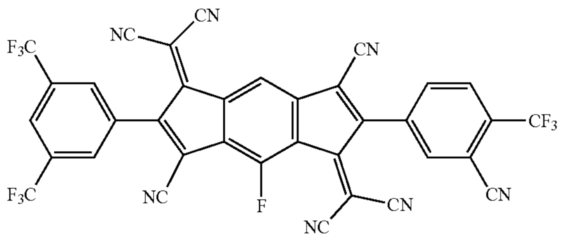

-continued
55
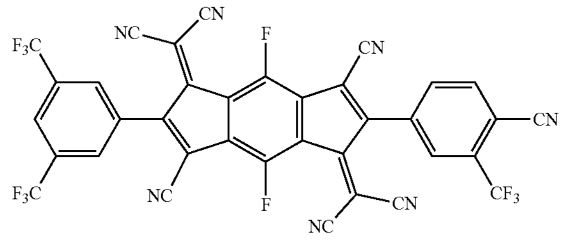
56
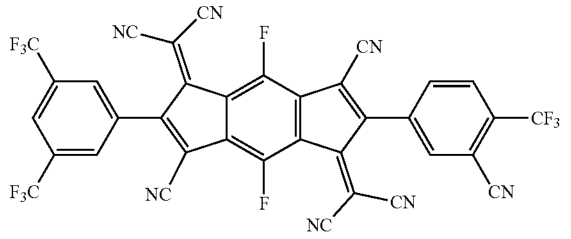
57
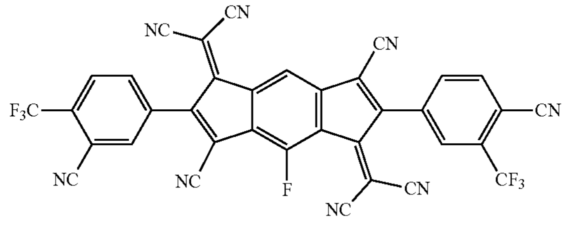
58
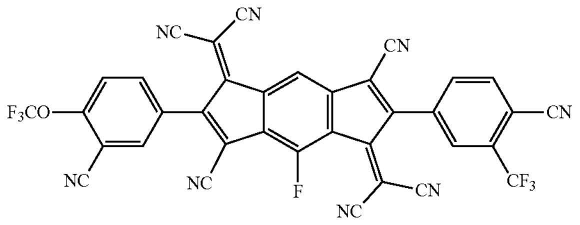
59
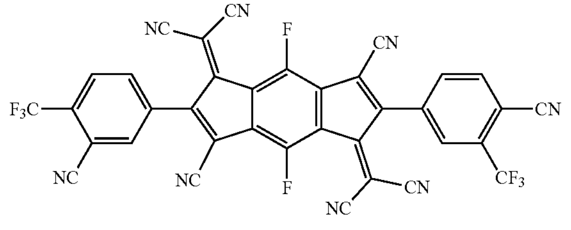
60
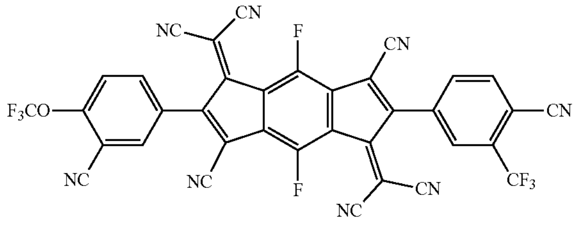
-continued
61
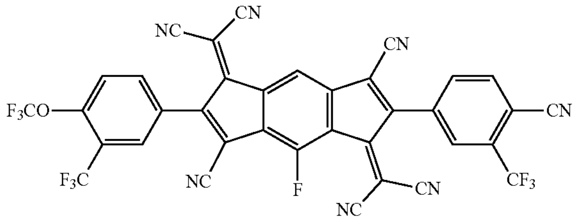
62
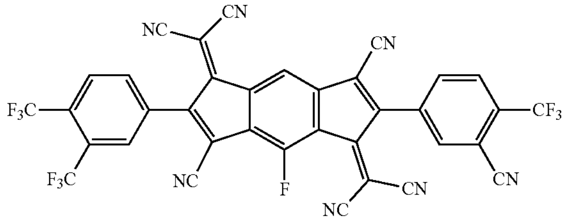
63
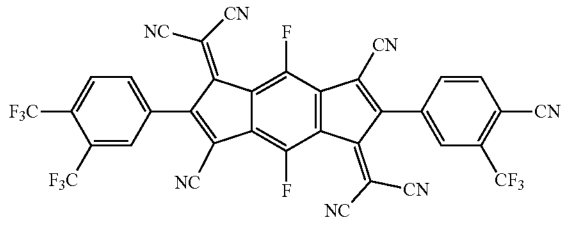
64
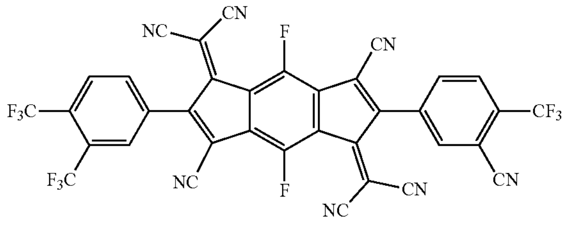
65
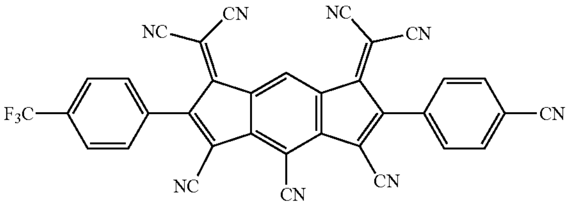
66
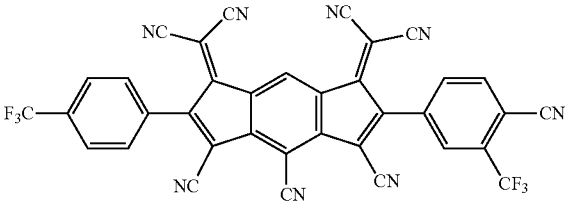

-continued
67
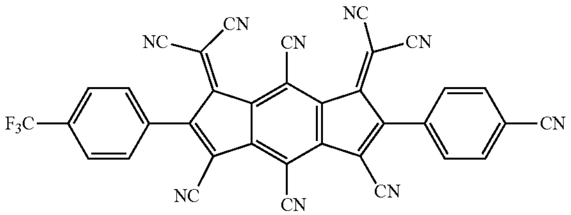
68
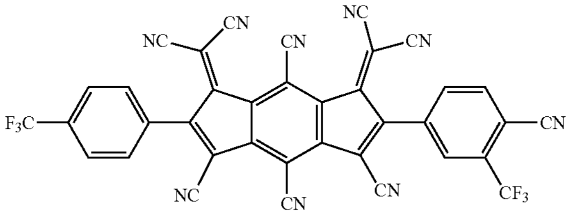
69
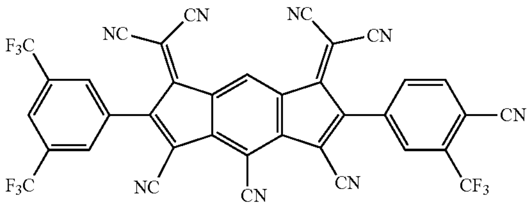
70
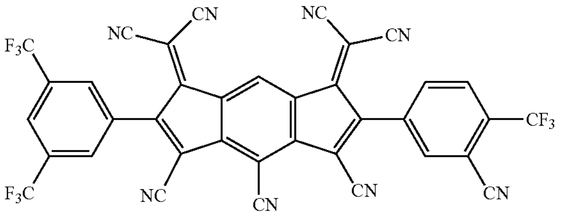
71
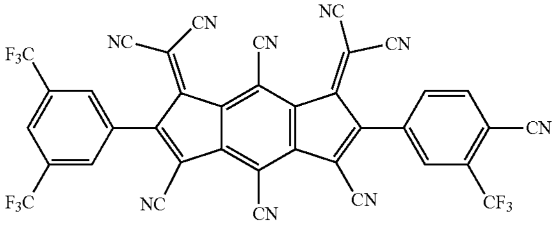
72
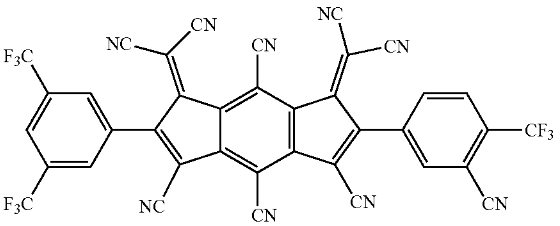
-continued
73
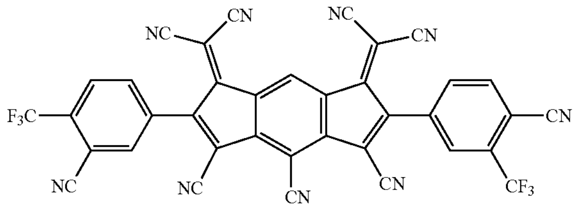
74
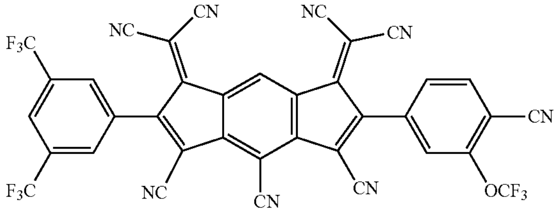
75
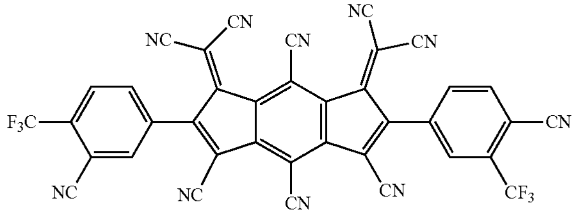
76
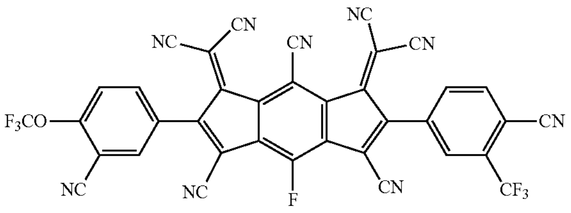
77
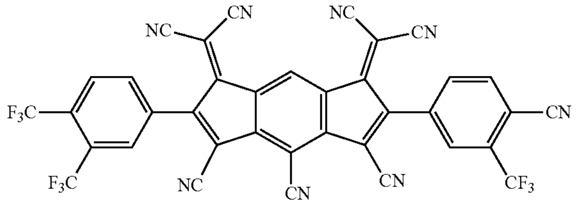
78
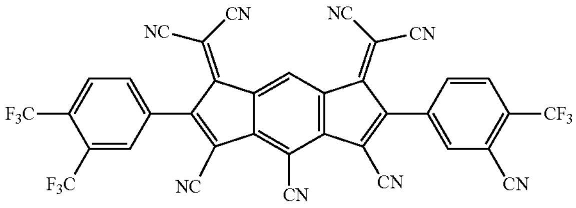

-continued
79
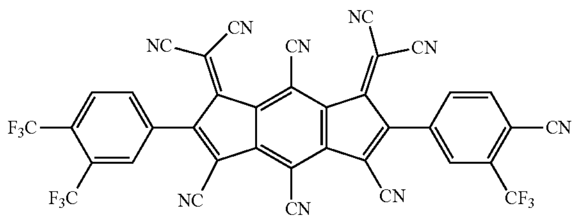
80
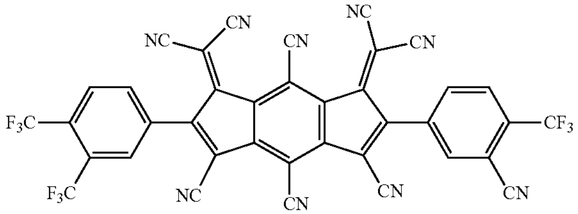
81
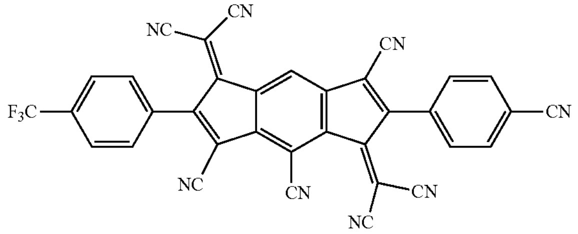
82
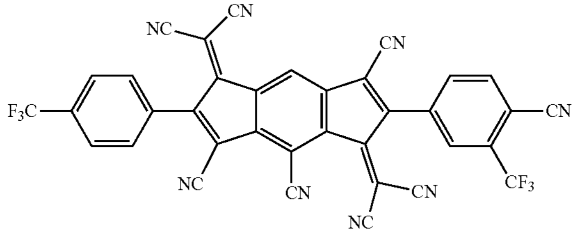
83
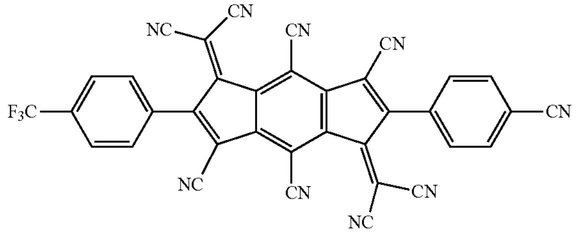
84
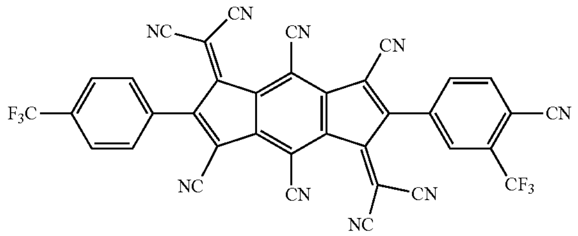
-continued
85
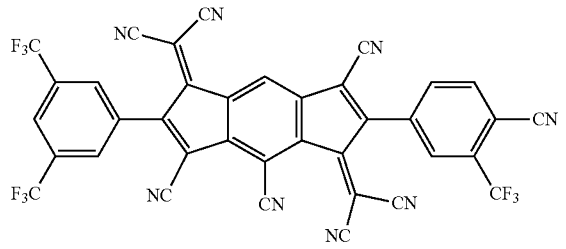
86
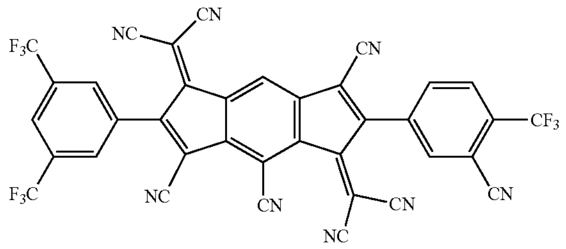
87
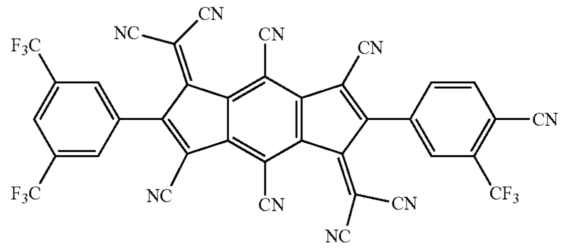
88
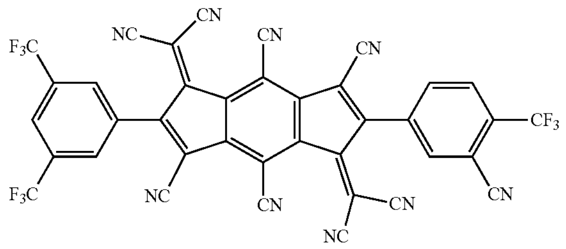
89
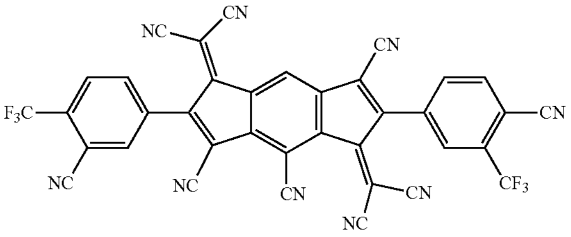
90
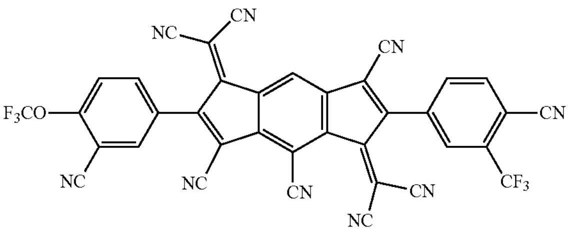

-continued

91

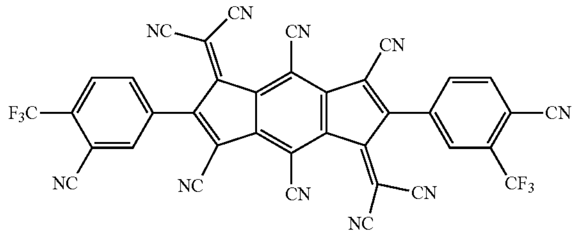

92

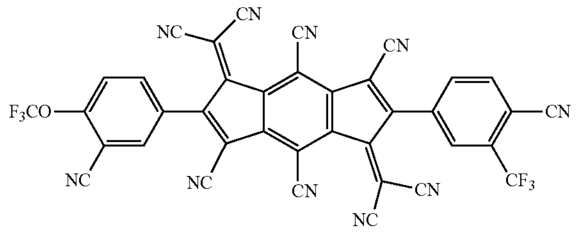

93

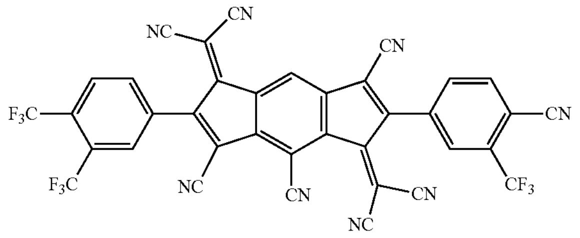

94

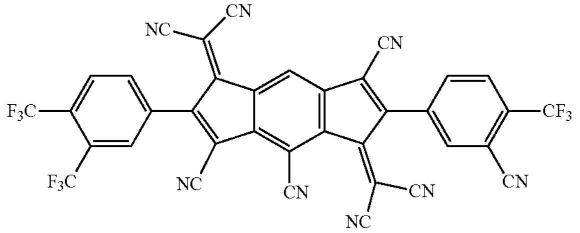

95

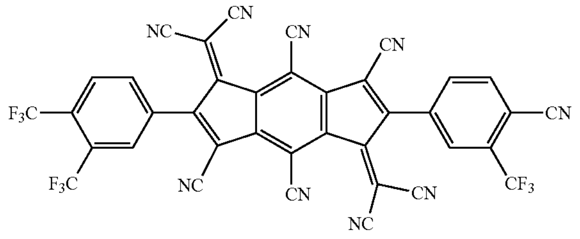

96

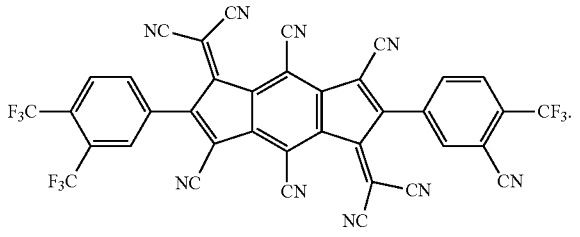

11. The organic light emitting diode according to claim 1, wherein the organic compound includes compounds in Formula 2-1, and each of the hole injection material and the first p-type charge generation material includes a compound in Formula 2-1:

[Formula 2-1]

4

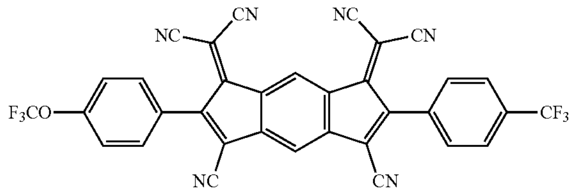

13

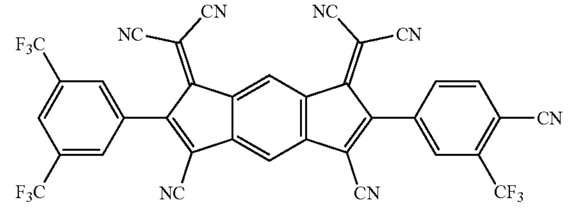

37

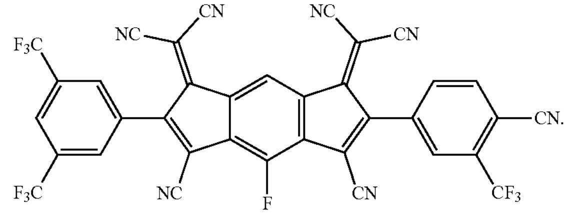

12. The organic light emitting device according to claim 8, wherein the organic compound includes compounds in Formula 2, and each of the hole injection material and the first p-type charge generation material includes a compound in Formula 2:

[Formula 2]

1

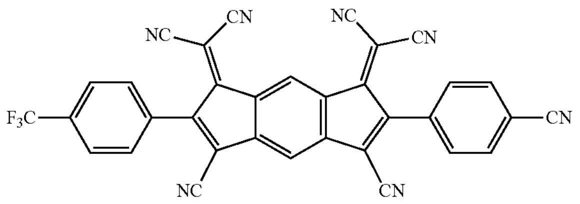

2

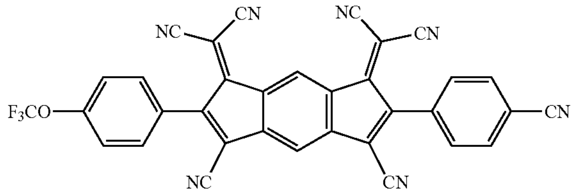

-continued
3
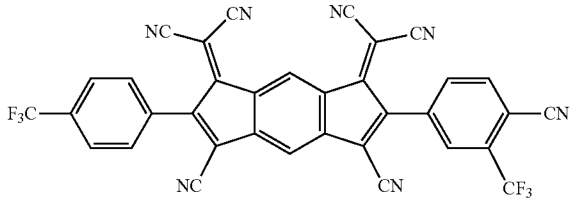
4
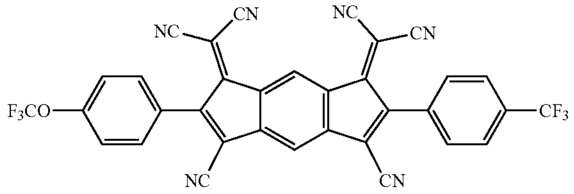
5
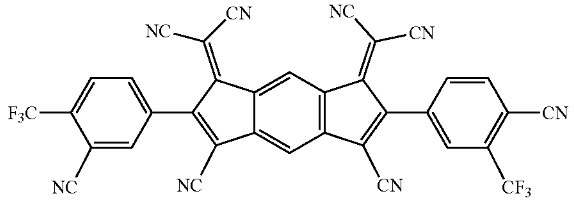
6
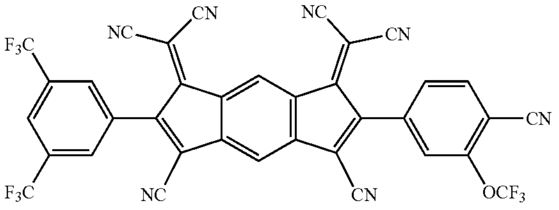
7
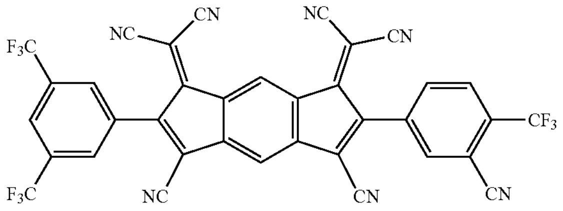
8
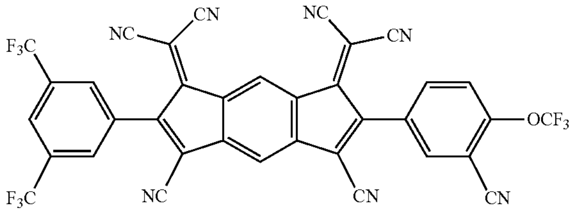
9
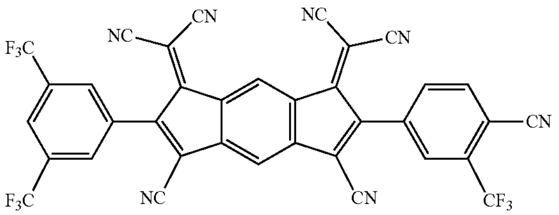
-continued
10
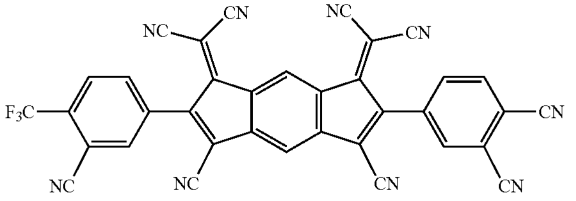
11
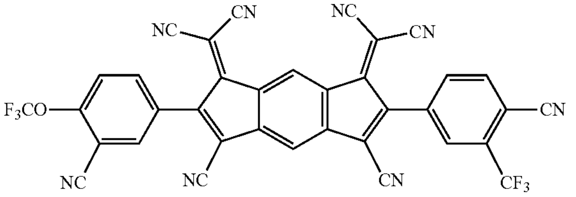
12
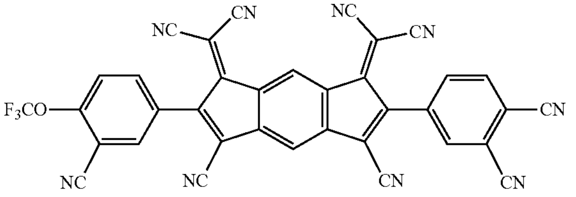
13
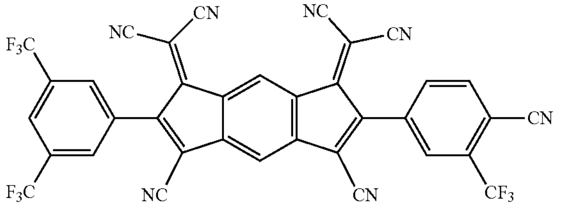
14
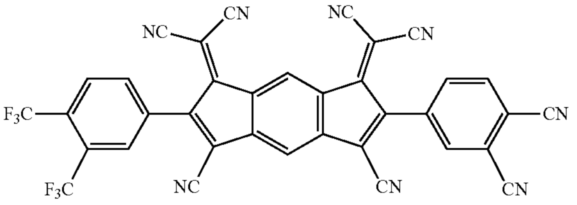
15
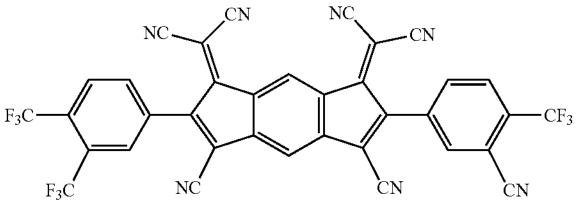
16
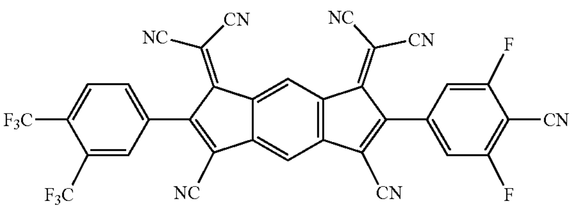

-continued
17
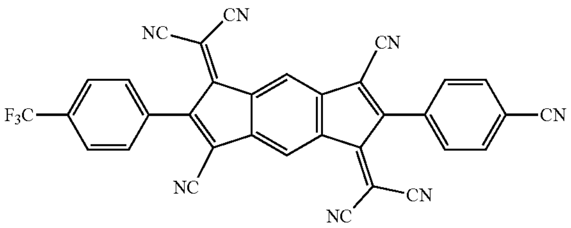
18
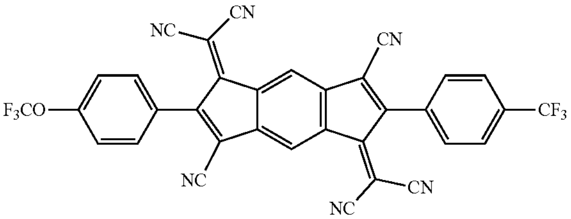
19
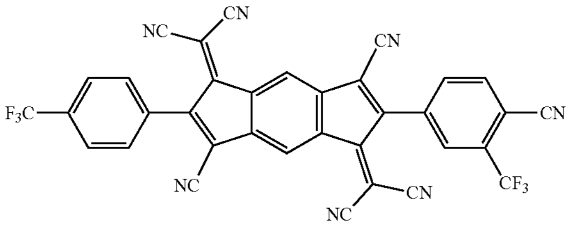
20
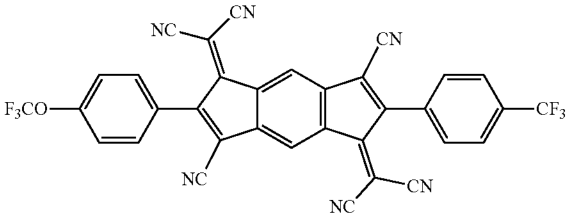
21
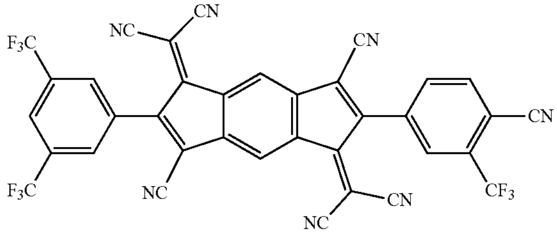
22
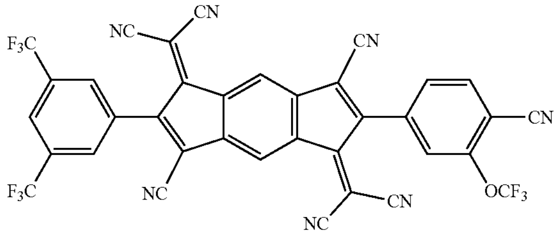
-continued
23
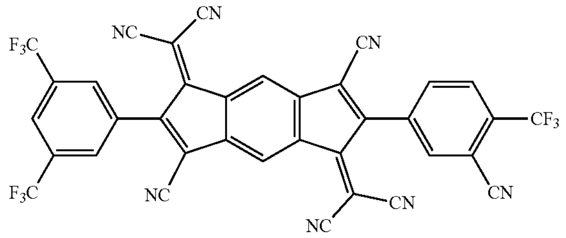
24
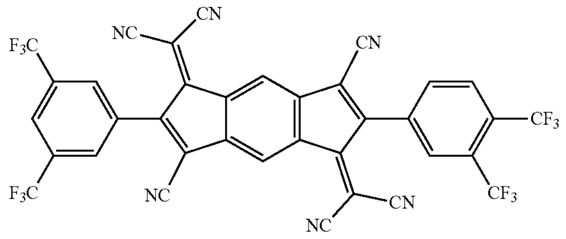
25
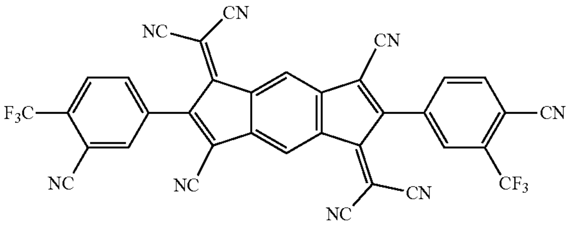
26
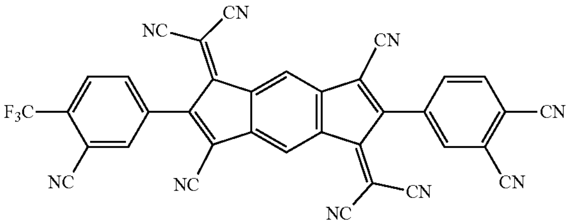
27
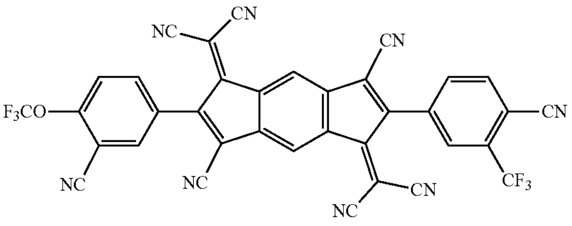
31
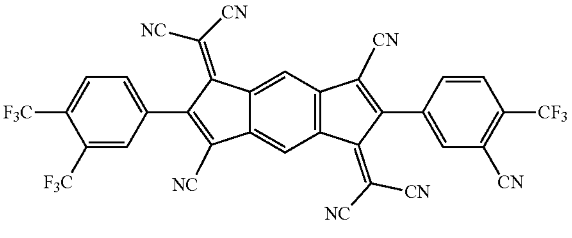

32
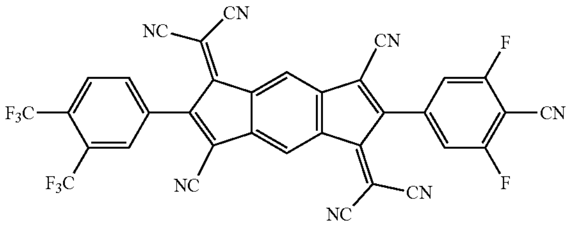
33
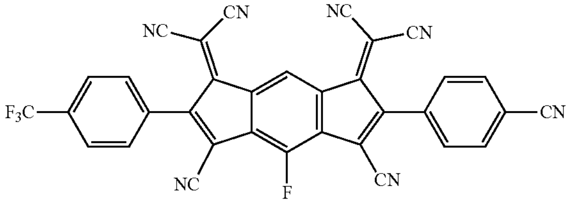
34
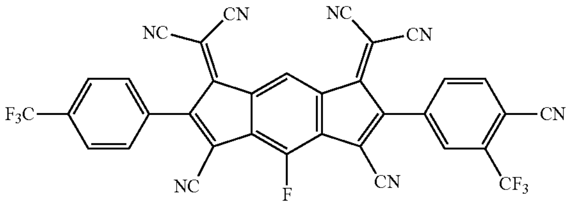
35
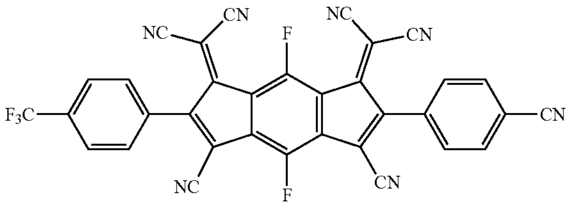
36
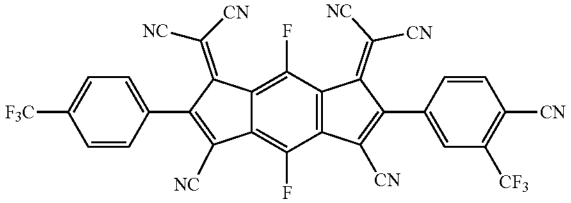
37
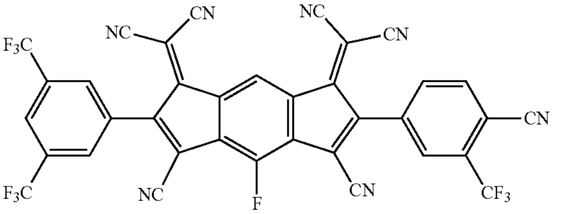
38
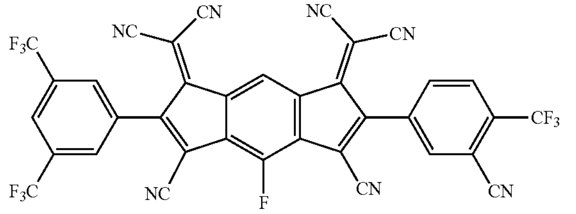
39
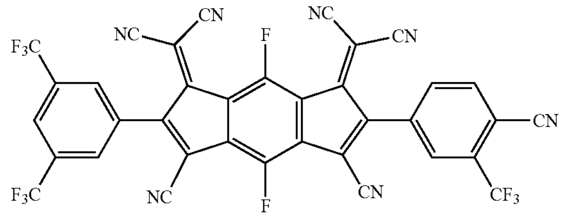
40
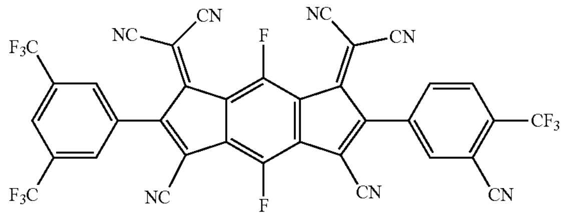
41
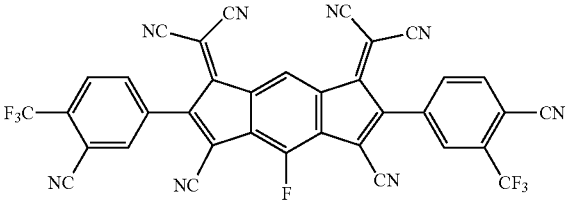
42
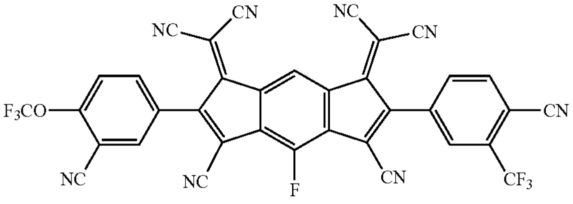
43
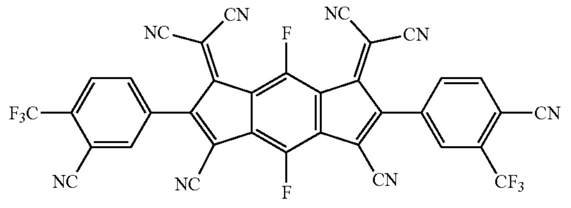
44
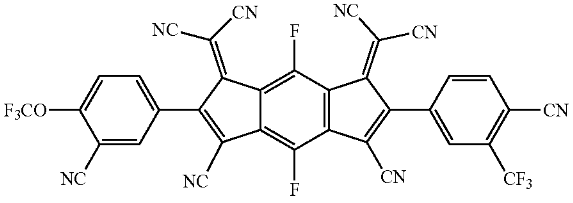

-continued
45
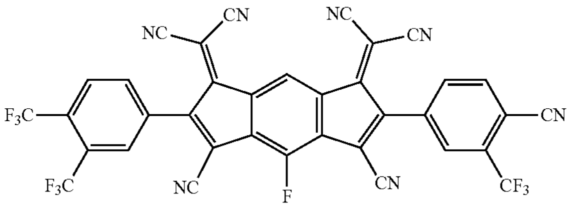
46
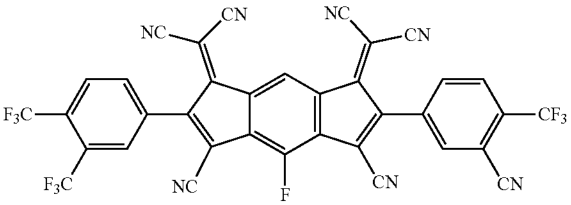
47
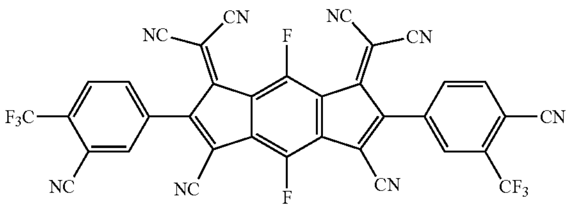
48
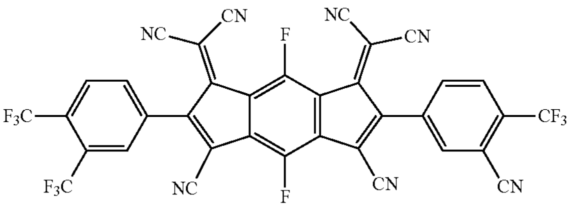
49
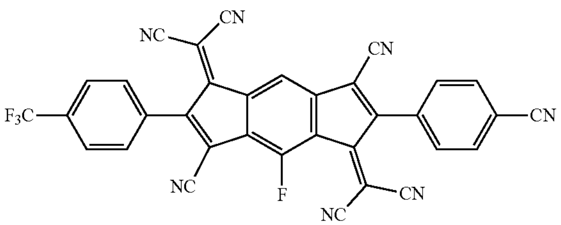
50
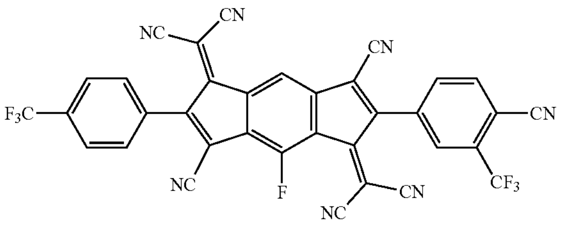
-continued
51
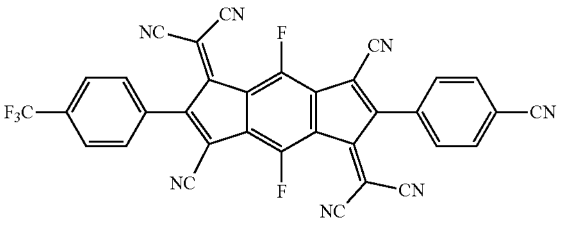
52
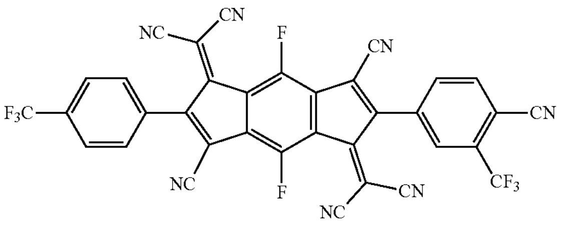
53
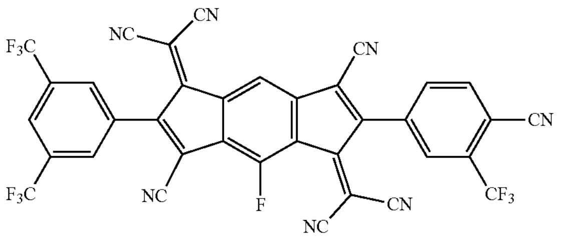
54
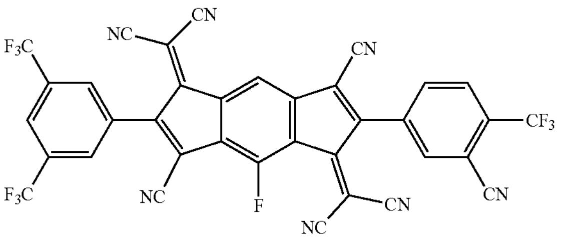
55
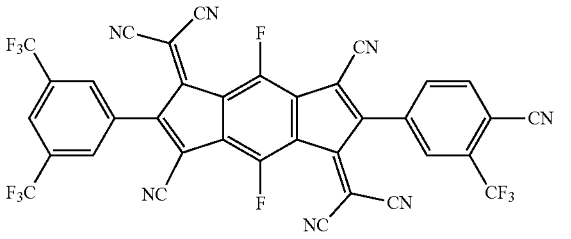
56
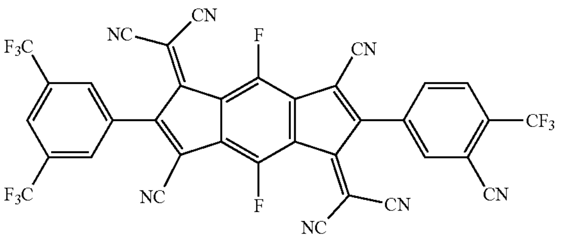

-continued
57
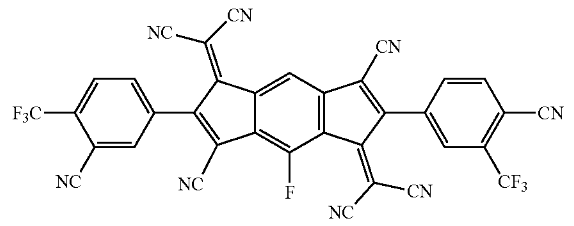
58
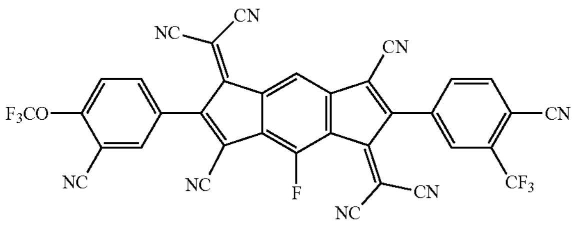
59
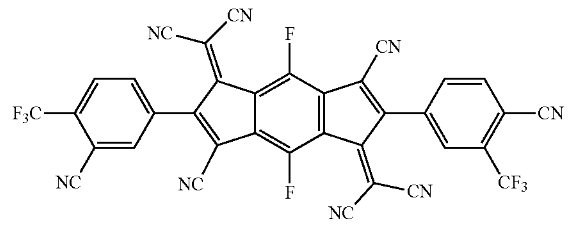
60
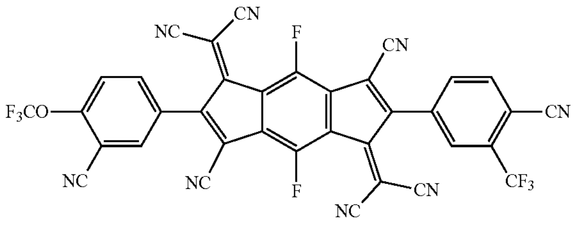
61
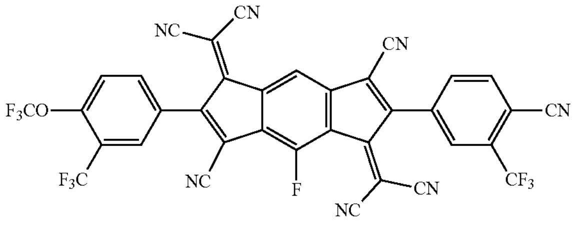
62
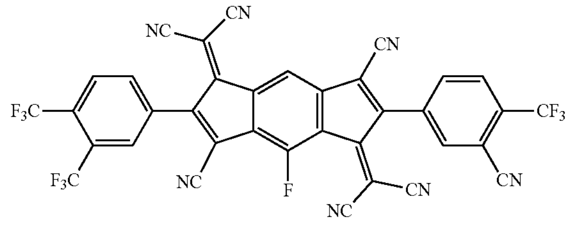
-continued
63
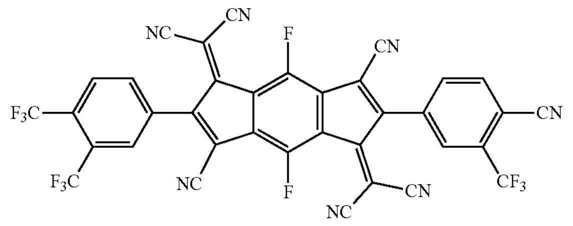
64
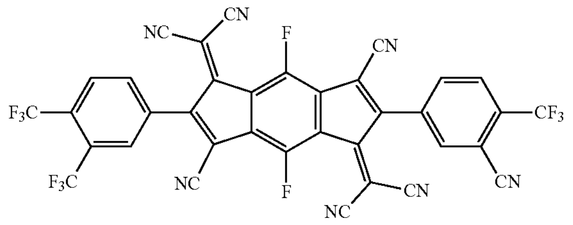
65
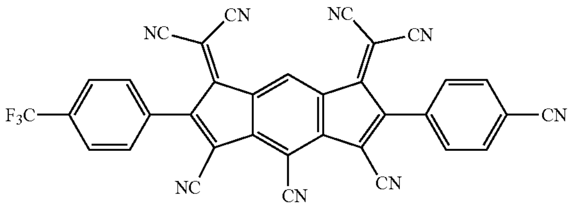
66
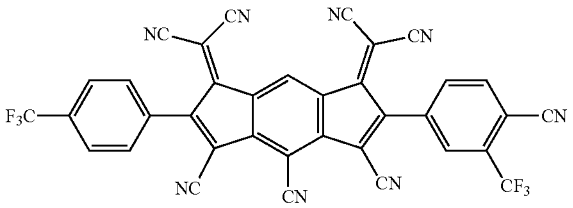
67
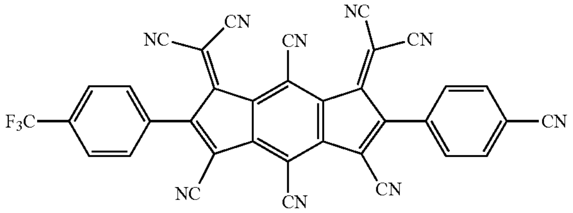
68
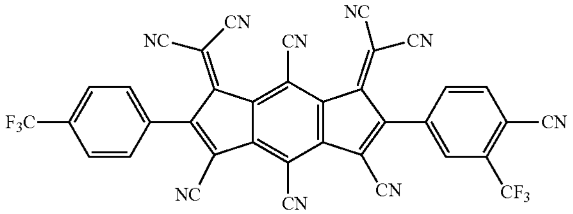

-continued
69
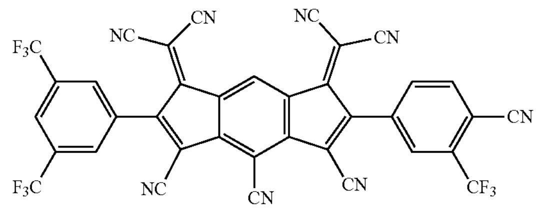
70
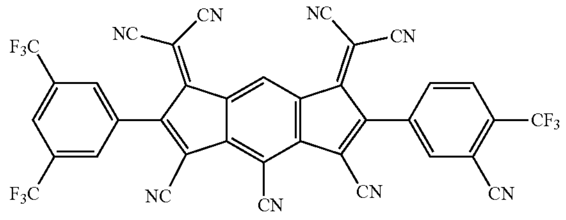
71
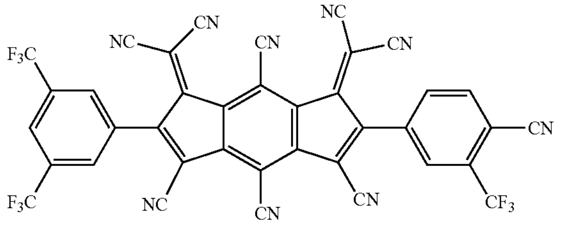
72
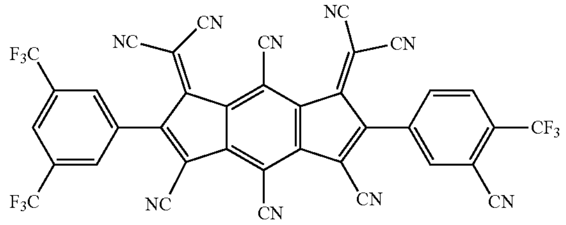
73
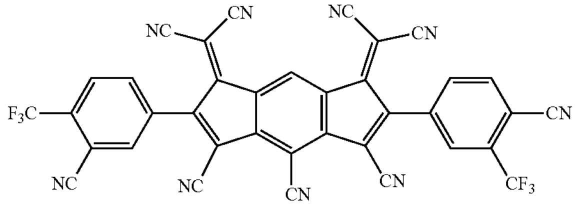
74
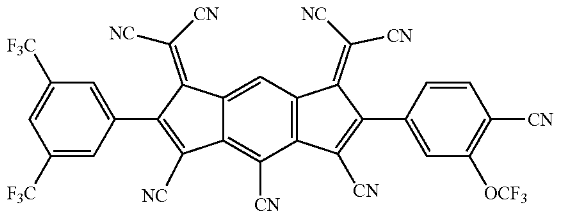
-continued
75
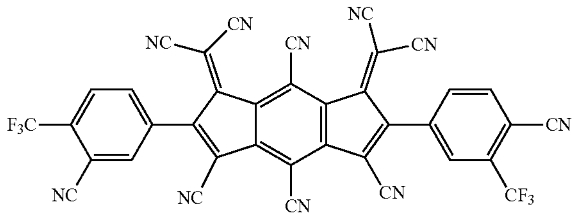
76
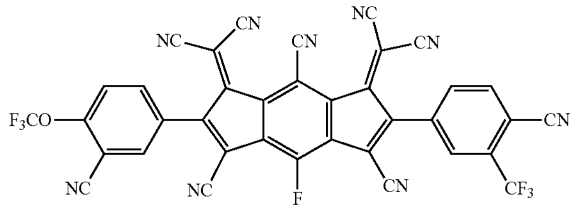
77
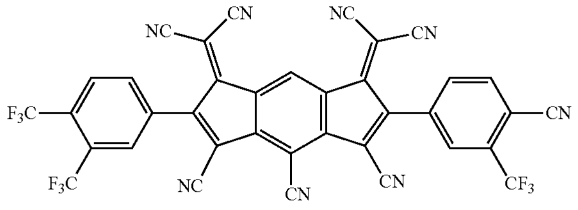
78
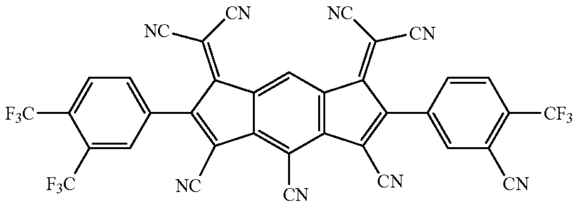
79
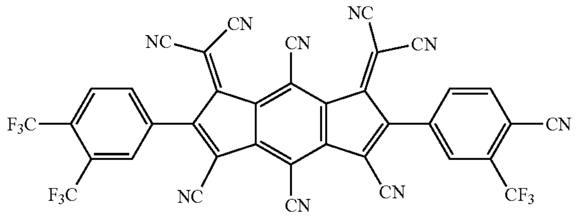
80
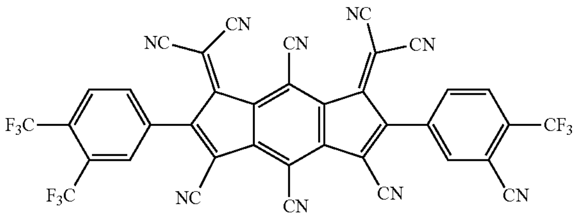

-continued
81
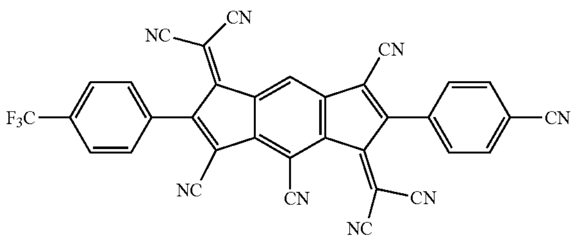
82
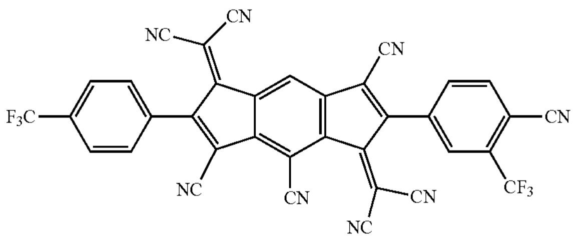
83
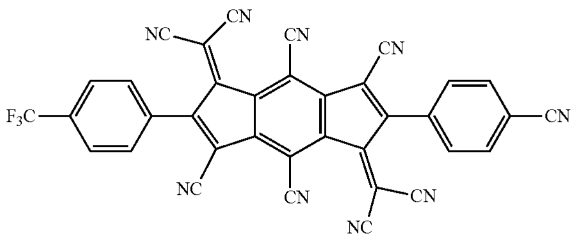
84
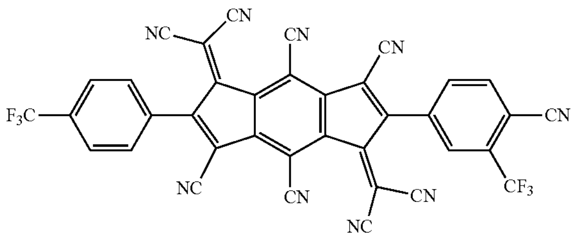
85
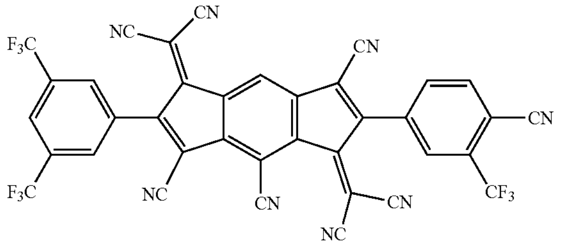
86
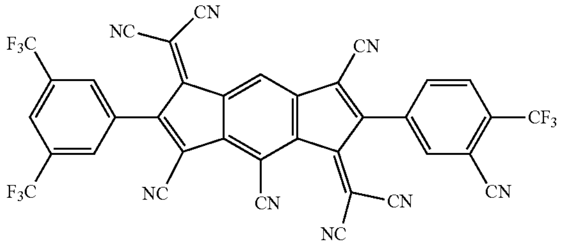
-continued
87
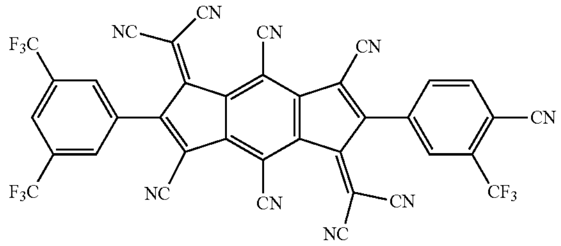
88
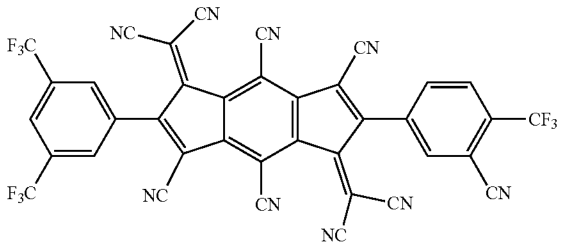
89
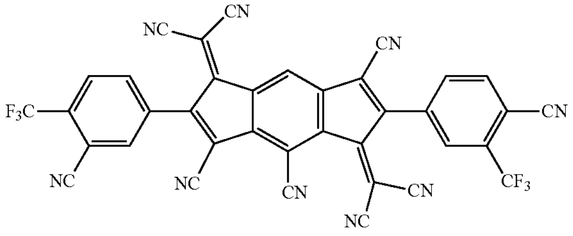
90
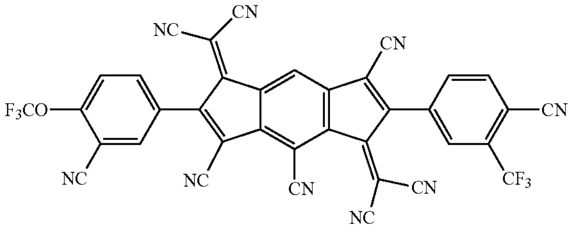
91
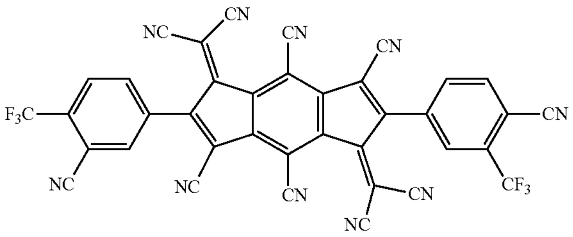
92
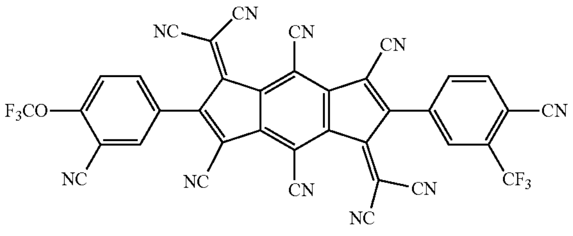

-continued
93
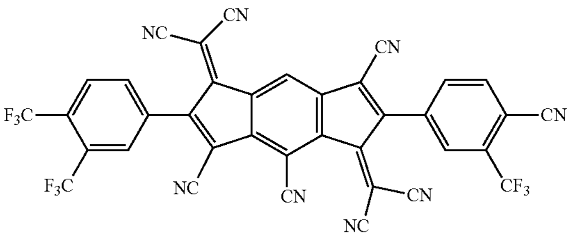
94
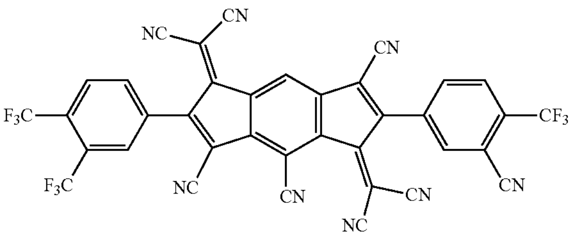
-continued
95
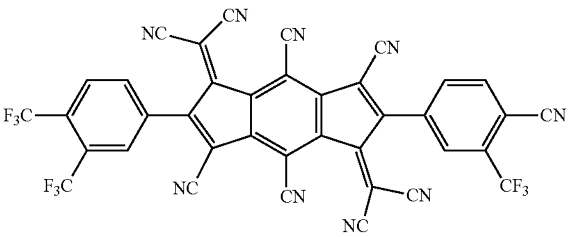
96
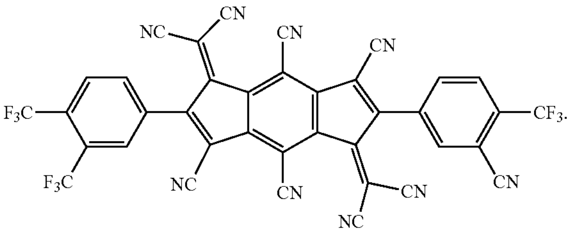
* * * * *